US012773155B2

(12) United States Patent
Tsukada

(10) Patent No.: US 12,773,155 B2
(45) Date of Patent: Oct. 27, 2026

(54) LEARNING APPARATUS, INFORMATION PROVIDING APPARATUS, LEARNING METHOD, INFORMATION PROVIDING METHOD AND PROGRAM

(71) Applicant: NTT, Inc., Tokyo (JP)

(72) Inventor: Shingo Tsukada, Musashino-shi (JP)

(73) Assignee: NTT, Inc., Tokyo (JP)

( * ) Notice: Subject to any disclaimer, the term of this patent is extended or adjusted under 35 U.S.C. 154(b) by 12 days.

(21) Appl. No.: 18/869,213

(22) PCT Filed: Jun. 20, 2022

(86) PCT No.: PCT/JP2022/024587
§ 371 (c)(1),
(2) Date: Nov. 25, 2024

(87) PCT Pub. No.: WO2023/248308
PCT Pub. Date: Dec. 28, 2023

(65) Prior Publication Data
US 2026/0013776 A1 Jan. 15, 2026

(51) Int. Cl.
*A61B 5/349* (2021.01)
*A61B 5/00* (2006.01)

(52) U.S. Cl.
CPC ............ *A61B 5/349* (2021.01); *A61B 5/7267* (2013.01); *A61B 5/7278* (2013.01)

(58) Field of Classification Search
CPC ....... A61B 5/0245; A61B 5/349; A61B 5/352; A61B 5/72329; A61B 5/7267;
(Continued)

(56) References Cited

U.S. PATENT DOCUMENTS

2002/0072682 A1 6/2002 Hopman et al.
2004/0030257 A1 2/2004 Tabbara et al.
(Continued)

FOREIGN PATENT DOCUMENTS

JP 2018504199 A 2/2018
WO 2016077786 A1 5/2016

OTHER PUBLICATIONS

Hiroshi Tanaka, Methodology in Electrocardiogramverse Problems, Medical Electronics and Biotechnology, 1985, vol. 23, No. 3, p. 147-158.
(Continued)

*Primary Examiner* — Michael T Rozanski

(57) ABSTRACT

A learning device includes a learning unit that sets, as a myocardial activity parameter set, a set of parameters representing an approximate function when a waveform in a time section included in a waveform for one cycle indicating a cardiac cycle of a heart is approximated by an approximate function including a difference or a weighted difference of a cumulative distribution function, and performs learning of an estimation model that obtains heart state information that is information representing a state of a heart corresponding to the myocardial activity parameter with a myocardial activity parameter set as an input, by using a learning data set, in which the learning data set includes a plurality of (Y) pieces of learning data, and each of the plurality of (Y) pieces of learning data includes a myocardial activity parameter set of a heart that is a target of y-th learning data, and heart state information that is information representing a state of the heart that is a target of the y-th learning data, where each of integers greater than or equal to 1 and less than or equal to Y is y.

7 Claims, 59 Drawing Sheets

(58) Field of Classification Search
CPC ... A61B 5/7278; G06F 18/2415; G06F 18/10; G16H 50/20; G16H 50/70
See application file for complete search history.

(56) References Cited

U.S. PATENT DOCUMENTS

| | | | |
|---|---|---|---|
| 2004/0039292 | A1 | 2/2004 | Schlegel et al. |
| 2012/0302903 | A1 | 11/2012 | Zhang et al. |
| 2015/0216426 | A1 | 8/2015 | Burton et al. |
| 2016/0127354 | A1 | 5/2016 | Borchardt et al. |
| 2018/0271453 | A1 | 9/2018 | Pak et al. |
| 2020/0113450 | A1 | 4/2020 | Nishioka et al. |

OTHER PUBLICATIONS

Wataru Shimizu et al., The role of M cells in the origin of T waves, Jpn. J. Electrocardiology, vol. 21, No. 2, 2001, p. 101 to 108.
Yoshifumi Tanaka, Shinji Nodo, Yasuo Yamazaki, Arisa Nakasone, Program for constructing body surface electrocardiogram from cardiac action potential waveform, Anaesthesia/intensive care and technology 2011 (1): p. 91 to 95, 2011.
Yoshifumi Tanaka et al., The ECG Recognition and Treatment of Antiarrhythmic Drugs, The Journal of Japan Society for Clinical Anesthesia, Oct. 28, 2010, vol. 30, No. 4, pp. 506-516.
Mohammad Saad Billah; Tahmida Binte Mahmud ; Farhana Sharmin Snigdha ; Muhammad Abdullah Arafat: A novel method to model ECG beats using Gaussian functions, Biomedical Engineering and Informatics (BMEI), 2011 4th International Conference on, IEEE, Oct. 15, 2011 (Oct. 15, 2011), pp. 612-616, XP032071565, DOI: 10.1109/BMEI.2011.6098409.
Kheirati Roonizi Ebadollah: A New Algorithm for Fitting a Gaussian Function Riding on the Polynomial Background, IEEE Signal Processing Letters, IEEE, USA, vol. 20, No. 11, Nov. 1, 2013 (Nov. 1, 2013), pp. 1062-1065, XP011526432, ISSN: 1070-9908, DOI: 10.1109/LSP.2013.2280577 [retrieved on Sep. 11, 2013].
Mahsa Akhbari et al: ECG denoising and fiducial point extraction using an extended Kalman filtering framework with linear and nonlinear phase observations, Physiological Measurement, Institute of Physics Publishing, Bristol, GB, vol. 37, No. 2, Jan. 15, 2016 (Jan. 15, 2016), pp. 203-226, XP020297441, ISSN: 0967-3334, DOI: 10.1088/0967-3334/37/2/203 [retrieved on Jan. 15, 2016].
International Search Report of the ISA issued in PCT/JP2021/000209, mailed Mar. 16, 2021; ISA/JP.
Team, Editorial. “What is Unimodal Distribution? A Comprehensive Guide [2025].” “Unimodal Distribution: A Comprehensive Guide with Interactive Tools”, SixSigma.Us, Apr. 17, 2025, www.6sigma.US/six-sigma-infocus/unimodal-distribution/.

LEARNING APPARATUS, INFORMATION PROVIDING APPARATUS, LEARNING METHOD, INFORMATION PROVIDING METHOD AND PROGRAM

CROSS-REFERENCE TO RELATED APPLICATIONS

This application is a 371 U.S. National Phase of International Application No. PCT/JP2022/024587 filed on Jun. 20, 2022. The entire disclosure of the above application is incorporated herein by reference.

TECHNICAL FIELD

The present invention relates to a learning apparatus, an information providing apparatus, a learning method, an information providing method and a program.

BACKGROUND ART

An electrocardiogram is useful information for grasping a state of a heart, and for example, if the electrocardiogram is used, whether a target is in a state in which there is a high possibility that heart failure occurs can be determined (Non Patent Document 1).

CITATION LIST

Non Patent Document

Non Patent Document 1: Hiroshi Tanaka, "On the Inverse Solution of Electrocardiology", Medical Electronics and Biological Engineering, 1985, Vol. 23, No. 3, p. 147-158

SUMMARY OF INVENTION

Technical Problem

However, a waveform of an electrocardiogram is not necessarily sufficient for grasping the state of the heart in some cases. For example, even if waveforms of electrocardiograms are similar to each other, manners of the onset of a disease related to the heart may be different from each other. As described above, it may be difficult to grasp the state of the heart depending on the disease only by looking at the waveform itself of the electrocardiogram. For example, in a case of heart failure, for suppression of it, the onset can be suppressed by observing the state of the heart by using the waveform of the electrocardiogram in daily life. In order to further increase accuracy of suppressing the onset, it is conceivable to acquire other information by using another technique such as collecting blood, but it is not realistic to do that in daily life. For that reason, depending on the disease, the state of the heart must be grasped substantially on the basis of only the waveform of the electrocardiogram in some cases.

Furthermore, such circumstances are not limited to a case of grasping the state of the heart on the basis of the waveform of the electrocardiogram. Such circumstances are also common in a case of grasping the state of the heart on the basis of time-series biological information on one channel regarding pulsation of the heart acquired by a sensor in contact with a body surface, a sensor close to the body surface, a sensor inserted into a body, a sensor embedded in the body, or the like. Note that the time-series biological information regarding the pulsation of the heart is, for example, a waveform indicating a change in cardiac potential, a waveform indicating a change in pressure of the heart, a waveform indicating a change in blood flow rate, and a waveform indicating a change in heart sound. Note that the waveform of the electrocardiogram is also an example of the time-series biological information regarding the pulsation of the heart.

In view of the above circumstances, an object of the present invention is to provide a technique for obtaining useful information for grasping a state of a heart from time-series biological information on one channel regarding pulsation of the heart.

Solution to Problem

An aspect of the present invention is a learning device comprising a learning unit that: sets a waveform in a time section of an R wave included in a waveform for one cycle indicating a cardiac cycle of a heart as a first target time waveform; sets a waveform in a time section of a T wave included in the waveform as a second target time waveform; sets a waveform obtained by inverting a time axis of the second target time waveform as a second target inverse time waveform; sets a cumulative distribution function of a first unimodal distribution as a first cumulative distribution function, and sets a cumulative distribution function of a second unimodal distribution as a second cumulative distribution function; sets, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function; sets a cumulative distribution function of a third unimodal distribution as a third cumulative distribution function, sets a cumulative distribution function of a fourth unimodal distribution as a fourth cumulative distribution function, sets a function obtained by subtracting the third cumulative distribution function from 1 as a third inverse cumulative distribution function, and sets a function obtained by subtracting the fourth cumulative distribution function from 1 as a fourth inverse cumulative distribution function; sets, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function; sets, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, sets a cumulative distribution function of a fifth unimodal distribution as a fifth cumulative distribution function, and sets a cumulative distribution function of a sixth unimodal distribution as a sixth cumulative distribution function; sets, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function; sets, as one or more types of myocardial activity parameters included in the fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group; sets, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and performs learning of an estimation model that obtains heart state information that is information representing a state of a heart corresponding to the myocardial activity parameter with a myocardial activity parameter set as an input, by using a learning data set, in which the learning data set includes Y pieces of learning data (Y is a plural number), and each of the Y pieces of learning data includes a myocardial activity parameter set of a heart that is a target of a y-th learning data, and heart state information that is information representing a state of the heart that is the target of the y-th learning data, where each of integers greater than or equal to 1 and less than or equal to Y is y.

An aspect of the present invention is an information provision device including a state information generation unit that: sets a waveform in a time section of an R wave included in a waveform for one cycle indicating a cardiac cycle of a heart as a first target time waveform; sets a waveform in a time section of a T wave included in the waveform as a second target time waveform; sets a waveform obtained by inverting a time axis of the second target time waveform as a second target inverse time waveform; sets a cumulative distribution function of a first unimodal distribution as a first cumulative distribution function, and sets a cumulative distribution function of a second unimodal distribution as a second cumulative distribution function; sets, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function; sets a cumulative distribution function of a third unimodal distribution as a third cumulative distribution function, sets a cumulative distribution function of a fourth unimodal distribution as a fourth cumulative distribution function, sets a function obtained by subtracting the third cumulative distribution function from 1 as a third inverse cumulative distribution function, and sets a function obtained by subtracting the fourth cumulative distribution function from 1 as a fourth inverse cumulative distribution function; sets, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function; sets, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, sets a cumulative distribution function of a fifth unimodal distribution as a fifth cumulative distribution function, and sets a cumulative distribution function of a sixth unimodal distribution as a sixth cumulative distribution function; sets, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function; sets, as one or more types of myocardial activity parameters included in the fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group; sets, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and obtains heart state information on an information provision target heart with a myocardial activity parameter set of the information provision target heart that is a heart to be a target of information provision as an input, by using an estimation model, in which the estimation model that obtains heart state information that is information representing a state of a heart corresponding to a myocardial activity parameter set with the myocardial activity parameter set as an input is stored in advance.

An aspect of the present invention is a learning method executed by a learning device, the learning method including a learning step of: setting a waveform in a time section of an R wave included in a waveform for one cycle indicating a cardiac cycle of a heart as a first target time waveform; setting a waveform in a time section of a T wave included in the waveform as a second target time waveform; setting a waveform obtained by inverting a time axis of the second target time waveform as a second target inverse time waveform; setting a cumulative distribution function of a first unimodal distribution as a first cumulative distribution function, and setting a cumulative distribution function of a second unimodal distribution as a second cumulative distribution function; setting, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function; setting a cumulative distribution function of a third unimodal distribution as a third cumulative distribution function, setting a cumulative distribution function of a fourth unimodal distribution as a fourth cumulative distribution function, setting a function obtained by subtracting the third cumulative distribution function from 1 as a third inverse cumulative distribution function, and setting a function obtained by subtracting the fourth cumulative distribution function from 1 as a fourth inverse cumulative distribution function; setting, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function; setting, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, setting a cumulative distribution function of a fifth unimodal distribution as a fifth cumulative distribution function, and setting a cumulative distribution function of a sixth unimodal distribution as a sixth cumulative distribution function; setting, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function; setting, as one or more types of myocardial activity parameters included in the fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group; setting, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and performing learning of an estimation model that obtains heart state information that is information representing a state of a heart corresponding to the myocardial activity parameter with a myocardial activity parameter set as an input, by using a learning data set, in which the learning data set includes Y pieces of learning data (Y is a plural number), and each of the Y pieces of learning data includes a myocardial activity parameter set of a heart that is a target of a y-th learning data, and heart state information that is information representing a state of the heart that is the target of the y-th learning data, where each of integers greater than or equal to 1 and less than or equal to Y is y.

An aspect of the present invention is an information provision method executed by an information provision device, the information provision method including a state information generation step of: setting a waveform in a time section of an R wave included in a waveform for one cycle indicating a cardiac cycle of a heart as a first target time waveform; setting a waveform in a time section of a T wave included in the waveform as a second target time waveform; setting a waveform obtained by inverting a time axis of the second target time waveform as a second target inverse time waveform; setting a cumulative distribution function of a first unimodal distribution as a first cumulative distribution function, and setting a cumulative distribution function of a second unimodal distribution as a second cumulative distribution function; setting, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function; setting a cumulative distribution function of a third unimodal distribution as a third cumulative distribution function, setting a cumulative distribution function of a fourth unimodal distribution as a fourth cumulative distribution function, setting a function obtained by subtracting the third cumulative distribution function from 1 as a third inverse cumulative distribution function, and setting a function obtained by subtracting the fourth cumulative distribution function from 1 as a fourth inverse cumulative distribution function; setting, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function; setting, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, setting a cumulative distribution function of a fifth unimodal distribution as a fifth cumulative distribution function, and setting a cumulative distribution function of a sixth unimodal distribution as a sixth cumulative distribution function; setting, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function; setting, as one or more types of myocardial activity parameters included in the fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group; setting, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and obtaining heart state information on an information provision target heart with a myocardial activity parameter set of the information provision target heart that is a heart to be a target of information provision as an input, by using an estimation model, in which the estimation model that obtains heart state information that is information representing a state of a heart corresponding to a myocardial activity parameter set with the myocardial activity parameter set as an input is stored in advance.

An aspect of the present invention is a program for causing a computer to function as the learning device described above.

An aspect of the present invention is a program for causing a computer to function as the information provision device.

Advantageous Effects of Invention

According to the present invention, it is possible to provide a technique for obtaining useful information for grasping a state of a heart from time-series biological information on one channel regarding pulsation of the heart.

DESCRIPTION OF EMBODIMENTS

First Embodiment

Figure 1:
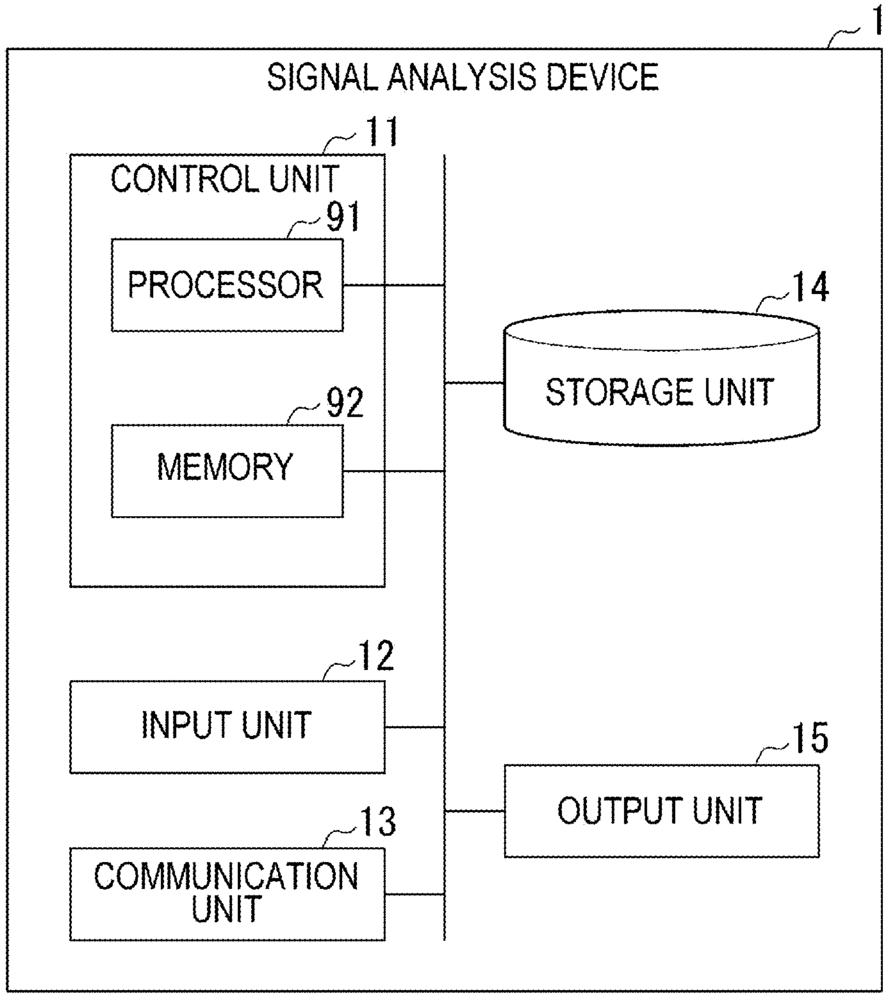
FIG. 1 is a diagram illustrating an example of a hardware configuration of a signal analysis device 1 of a first embodiment.

FIG. 1 is a diagram illustrating an example of a hardware configuration of a signal analysis device 1 of a first embodiment. Hereinafter, for simplicity of description, the signal analysis device 1 will be described with an example of a case where analysis is performed on the basis of a waveform of one channel of an electrocardiogram. However, the signal analysis device 1 can perform similar analysis on the basis of not only a waveform of an electrocardiogram but also time-series biological information regarding pulsation of a heart. Note that the time-series biological information regarding the pulsation of the heart is, for example, a waveform indicating a change in cardiac potential, a waveform indicating a change in pressure of the heart, a waveform indicating a change in blood flow rate, and a waveform indicating a change in heart sound. For that reason, the signal analysis device 1 may use not only a waveform of an electric signal acquired from a body surface but also any waveform as long as the waveform indicates a cardiac cycle acquired from any point regardless of whether the point is on the body surface or in the body, by using a sensor in contact with the body surface, a sensor close to the body surface, a sensor inserted into the body, a sensor embedded in the body, or the like.

That is, the signal analysis device 1 may use the waveform indicating the change in pressure of the heart as the time-series biological information regarding the pulsation of the heart instead of the waveform of the electrocardiogram. Furthermore, the signal analysis device 1 may use the waveform indicating the change in blood flow rate as the time-series biological information regarding the pulsation of the heart instead of the waveform of the electrocardiogram. Furthermore, the signal analysis device 1 may use the waveform indicating the change in heart sound as the time-series biological information regarding the pulsation of the heart instead of the waveform of the electrocardiogram. Note that the waveform of the electrocardiogram is also an example of the time-series biological information regarding the pulsation of the heart. Note that the time-series biological information regarding the pulsation of the heart may be time-series biological information regarding cyclical pulsation of the heart.

The signal analysis device 1 acquires a waveform of an electrocardiogram of a heart that is an analysis target (hereinafter, referred to as a "target heart"). On the basis of the acquired waveform of the electrocardiogram, the signal analysis device 1 acquires a parameter indicating activity of a myocardium of the target heart (hereinafter referred to as a "myocardial activity parameter") including at least one of a parameter indicating activity of an outer layer of the myocardium (hereinafter, referred to as a "myocardial outer layer") of the target heart (hereinafter, the parameter is referred to as a "myocardial outer layer parameter") or a parameter indicating activity of an inner layer of the myocardium (hereinafter, referred to as a "myocardial inner layer") of the target heart (hereinafter, the parameter is referred to as a "myocardial inner layer parameter").

Here, a relationship between activity of a myocardium and a waveform of an electrocardiogram will be described. In the medical field, a model for describing a relationship between movement of a myocardium and an electrocardiogram called an electromotive force dipole model (Reference Document 1) is known. According to the electromotive force dipole model, a myocardium is modeled using two layers of a myocardial outer layer and a myocardial inner layer.

Reference Document 1: Yoshifumi Tanaka, "Understanding electrocardiogram waveforms from their origins, Interpreting myocardial action potentials", Gakken Medical Shujunsha Co., Ltd. (2012)

In the electromotive force dipole model, the myocardial outer layer and the myocardial inner layer are modeled as different electromotive force generation sources. According to the electromotive force dipole model, a synthesized wave of an epicardial myocardial action potential and an endocardial myocardial action potential substantially corresponds to a temporal change in potential of a body surface observed on the body surface. A graph representing the temporal change in potential of the body surface is the waveform of the electrocardiogram. The epicardial myocardial action potential is a result of directly measuring a change in electromotive force generated by pulsation of the myocardial outer layer by inserting a catheter electrode. The endocardial myocardial action potential is a result of directly measuring a change in electromotive force generated by pulsation of the myocardial inner layer by inserting the catheter electrode. The above is a schematic description of the electromotive force dipole model.

Meanwhile, the myocardial outer layer in the electromotive force dipole model is a population of cells. For that reason, pulsation timings of cells in the myocardial outer layer in one-time pulsation of the myocardial outer layer are not necessarily the same in all the cells, and there is a possibility that there is a distribution in the pulsation timings. The same applies to the myocardial inner layer. That is, pulsation timings of cells in the myocardial inner layer in one-time pulsation of the myocardial inner layer are not necessarily the same in all the cells, and there is a possibility that there is a distribution in the pulsation timings. However, such a possibility that there is a distribution in pulsation timings of cells is not assumed in the electromotive force dipole model.

Furthermore, there is also a distribution in distances between each cell and an electrode on the body surface, and configurations of body tissue between each cell and the electrode on the body surface are not the same. For that reason, pieces of conversion efficiency at which excitation of a cell in the myocardial outer layer is reflected in the waveform of the electrocardiogram are not necessarily the same in all the cells, and there is a possibility that there is a distribution in pieces of conversion efficiency at which pulsation is reflected in the waveform of the electrocardiogram. Similarly, pieces of conversion efficiency at which excitation of a cell in the myocardial inner layer is reflected in the waveform of the electrocardiogram are not necessarily the same in all the cells, and there is a possibility that there is a distribution in pieces of conversion efficiency at which pulsation is reflected in the waveform of the electrocardiogram. However, such a possibility that there is a distribution in pieces of conversion efficiency at which pulsation of a cell is reflected in the waveform of the electrocardiogram is not assumed in the electromotive force dipole model.

In the signal analysis device 1, in consideration of the possibility that there is the distribution in the pulsation timings of cells and the possibility that there is the distribution in the pieces of conversion efficiency at which the pulsation of the cell is reflected in the waveform of the electrocardiogram, analysis is performed in which it is assumed that each of a distribution of timings at which the start of pulsation of each cell of the myocardial outer layer appears in the waveform of the electrocardiogram, a distribution of timings at which the start of pulsation of each cell of the myocardial inner layer appears in the waveform of the electrocardiogram, a distribution of timings at which the end of the pulsation of each cell of the myocardial outer layer appears in the waveform of the electrocardiogram, and a distribution of timings at which the end of the pulsation of each cell of the myocardial inner layer appears in the waveform of the electrocardiogram is a Gaussian distribution. That is, in the signal analysis device 1, analysis is performed in which it is assumed that the start of activity of the myocardial inner layer by all cells of the myocardial inner layer is included in the waveform of the electrocardiogram as a cumulative Gaussian distribution, the start of activity of the myocardial outer layer by all cells of the myocardial outer layer is included in the waveform of the electrocardiogram as a cumulative Gaussian distribution, the end of the activity of the myocardial inner layer by all the cells of the myocardial inner layer is included in the waveform of the electrocardiogram as a cumulative Gaussian distribution, and the end of the activity of the myocardial outer layer by all the cells of the myocardial outer layer is included in the waveform of the electrocardiogram as a cumulative Gaussian distribution.

Note that, although a cumulative Gaussian distribution function is preferably used in the signal analysis device 1, a sigmoid function, a Gompertz function, a logistic function, or the like may be used instead of the cumulative Gaussian distribution function. That is, the signal analysis device 1 may use, instead of the cumulative Gaussian distribution function, a cumulative distribution function of a unimodal distribution, that is, a cumulative distribution function corresponding to a distribution in which a value monotonically increases until time at which the value is a maximum value and monotonically decreases after the time at which the value is the maximum value. However, the cumulative distribution function used by the signal analysis device 1 needs to be a cumulative distribution function having a shape that can be specified by a parameter representing a shape of the cumulative distribution function or a parameter representing a shape of a unimodal distribution that is a cumulative source of the cumulative distribution function. Hereinafter, the parameter representing the shape of the cumulative distribution function (that is, a parameter specifying the cumulative distribution function) is referred to as a shape parameter of the cumulative distribution function, and the parameter representing the shape of the unimodal distribution (that is, a parameter specifying the unimodal distribution) is referred to as a shape parameter of the unimodal distribution. However, as a matter of course, the shape parameter of the cumulative distribution function and the shape parameter of the unimodal distribution are substantially the same. For example, in a case where the cumulative distribution function used by the signal analysis device 1 is a cumulative Gaussian distribution function, a standard deviation (or variance) and an average value of a Gaussian distribution that is a cumulative source of the cumulative Gaussian distribution function are shape parameters of the unimodal distribution and also shape parameters of the cumulative distribution function.

The signal analysis device 1 sets a waveform in a time section of any of an R wave and a T wave included in a waveform for one cycle of an acquired electrocardiogram of the target heart as a target time waveform, and acquires, as parameters representing characteristics of the target time waveform, that is, acquires, as myocardial activity parameters, a parameter specifying a first unimodal distribution or a parameter specifying a first cumulative distribution function, and a parameter specifying a second unimodal distribution or a parameter specifying a second cumulative distribution function when the target time waveform is approximated by a time waveform represented by a difference or a weighted difference between the first cumulative distribution function that is a cumulative distribution function of the first unimodal distribution and the second cumulative distribution function that is a cumulative distribution function of the second unimodal distribution (hereinafter, the time waveform is referred to as an "approximate time waveform"). Hereinafter, approximating the target time waveform represented by the approximate time waveform, that is, specifying the approximate time waveform is referred to as "fitting", and the first cumulative distribution function and the second cumulative distribution function included in the approximate time waveform are referred to as "fitting results". Note that, in a case where approximation is performed by the weighted difference, the signal analysis device 1 may also acquire, as parameters representing the characteristics of the target time waveform (that is, myocardial activity parameters), weight given to the first cumulative distribution function and weight given to the second cumulative distribution function, or may also acquire, as a parameter representing the characteristics of the target time waveform (that is, a myocardial activity parameter), a ratio between the weight given to the first cumulative distribution function and the weight given to the second cumulative distribution function.

In a case where the target time waveform is approximated by an approximate time waveform represented by a difference between the first cumulative distribution function and the second cumulative distribution function, for example, the signal analysis device 1 uses each of combinations (M×N) of parameters specifying cumulative distribution functions for a respective plurality of (M) candidates for the first cumulative distribution function and parameters specifying cumulative distribution functions for a respective plurality of (N) candidates for the second cumulative distribution function, to generate a time waveform (hereinafter referred to as a "candidate time waveform") represented by the difference between the first cumulative distribution function and the second cumulative distribution function, specifies, as the approximate time waveform, a candidate time waveform closest to the target time waveform among generated M×N candidate time waveforms, and acquires, as parameters representing the characteristics of the target time waveform, a parameter specifying a candidate for the first cumulative distribution function and a parameter specifying a candidate for the second cumulative distribution function used for generation of the specified approximate time waveform. Processing of specifying the candidate time waveform closest to the target time waveform as the approximate time waveform only needs to be performed by, for example, processing of specifying the candidate time waveform having a smallest square error between the candidate time waveform and the target time waveform.

Alternatively, for example, the signal analysis device 1 repeats obtaining a candidate time waveform that is a time waveform represented by a difference between the candidate for the first cumulative distribution function and the candidate for the second cumulative distribution function and that approximates the target time waveform, and updating at least any of parameters specifying respective cumulative distribution functions in a direction in which the square error between the candidate time waveform and the target time waveform decreases, until the square error is less than or equal to a predetermined standard, or a predetermined number of times, to specify a finally obtained candidate time waveform as the approximate time waveform, and acquires, as parameters representing the characteristics of the target time waveform, a parameter specifying a candidate for the first cumulative distribution function and a parameter specifying a candidate for the second cumulative distribution function used for generation of the specified approximate time waveform.

In a case where the target time waveform is approximated by an approximate time waveform represented by a weighted difference between the first cumulative distribution function and the second cumulative distribution function, for example, the signal analysis device 1 uses each of combinations (K×L×M×N) of parameters specifying cumulative distribution functions for a respective plurality of (M) candidates for the first cumulative distribution function, parameters specifying cumulative distribution functions for a respective plurality of (N) candidates for the second cumulative distribution function, a plurality of (K) candidates for the weight given to the first cumulative distribution function, and a plurality of (L) candidates for the weight given to the second cumulative distribution function, to generate a candidate time waveform that is a time waveform represented by the weighted difference between the first cumulative distribution function and the second cumulative distribution function, specifies, as the approximate time waveform, a candidate time waveform closest to the target time waveform among generated K×L×M×N candidate time waveforms, and acquires, as parameters representing the characteristics of the target time waveform, a parameter specifying a candidate for the first cumulative distribution function, a parameter specifying a candidate for the second cumulative distribution function, weight given to the first cumulative distribution function, and weight given to the second cumulative distribution function used for generation of the specified approximate time waveform.

Alternatively, for example, the signal analysis device 1 repeats obtaining a candidate time waveform that is a time waveform represented by a weighted difference between the candidate for the first cumulative distribution function and the candidate for the second cumulative distribution function and that approximates the target time waveform, and updating at least any of parameters specifying respective cumulative distribution functions and pieces of weight given to respective cumulative distribution functions in a direction in which the square error between the candidate time waveform and the target time waveform decreases, until the square error is less than or equal to a predetermined standard, or a predetermined number of times, to specify a finally obtained candidate time waveform as the approximate time waveform, and acquires, as parameters representing the characteristics of the target time waveform, a parameter specifying a candidate for the first cumulative distribution function, a parameter specifying a candidate for the second cumulative distribution function, weight given to the first cumulative distribution function, and weight given to the second cumulative distribution function used for generation of the specified approximate time waveform.

Hereinafter, processing of acquiring the parameters representing the characteristics of the target time waveform included in the waveform for one cycle of the acquired electrocardiogram of the target heart is referred to as myocardial activity information parameter acquisition processing.

When information representing time is x, in a case where Gaussian distributions are used as the first unimodal distribution and the second unimodal distribution, the first unimodal distribution is represented by following Formula (1), a first cumulative distribution function $f_1(x)$ is represented by Formula (2), the second unimodal distribution is represented by Formula (3), and a second cumulative distribution function $f_2(x)$ is represented by Formula (4).

[Math. 1]

$$\frac{1}{\sqrt{2\pi\sigma_1^2}}\exp\left(-\frac{(x-\mu_1)^2}{2\sigma_1^2}\right) \tag{1}$$

[Math. 2]

$$f_1(x) = \frac{1}{2}\left(1 + \operatorname{erf}\left(\frac{x-\mu_1}{\sqrt{2\sigma_1^2}}\right)\right) \tag{2}$$

[Math. 3]

$$\frac{1}{\sqrt{2\pi\sigma_2^2}}\exp\left(-\frac{(x-\mu_2)^2}{2\sigma_2^2}\right) \tag{3}$$

[Math. 4]

$$f_2(x) = \frac{1}{2}\left(1 + \operatorname{erf}\left(\frac{x-\mu_2}{\sqrt{2\sigma_2^2}}\right)\right) \tag{4}$$

Formula (1) is a Gaussian distribution (normal distribution) having an average of u and a standard deviation of $\sigma_1$ (variance of $\sigma_1^2$). Formula (3) is a Gaussian distribution (normal distribution) having an average of $\mu_2$ and a standard deviation of $\sigma_2$ (variance of $\sigma_2^2$). Formula (2) is a cumulative distribution function of Formula (1). Formula (4) is a cumulative distribution function of Formula (3). A function "erf" is a sigmoid function (error function). The unit of the information x representing time is arbitrary, and for example, it is sufficient to use, as the information x representing time, a sample number or relative time with a waveform of one cycle of an electrocardiogram as the start edge.

The difference between the first cumulative distribution function and the second cumulative distribution function is expressed by, for example, following Formula (5). The function expressed by following Formula (5) is a function obtained by subtracting the second cumulative distribution function from the first cumulative distribution function.

[Math. 5]

$$f_1(x) - f_2(x) = \frac{1}{2}\left(1 + \operatorname{erf}\left(\frac{x-\mu_1}{\sqrt{2\sigma_1^2}}\right)\right) - \frac{1}{2}\left(1 + \operatorname{erf}\left(\frac{x-\mu_2}{\sqrt{2\sigma_2^2}}\right)\right) \tag{5}$$

That is, when the target time waveform is approximated by the approximate time waveform that is the difference between the first cumulative distribution function and the second cumulative distribution function, the average $\mu_1$ and the standard deviation $\sigma_1$ that are parameters specifying the first unimodal distribution or parameters specifying the first cumulative distribution function, and the average $\mu_2$ and the standard deviation $\sigma_2$ that are parameters specifying the second unimodal distribution or the second cumulative distribution function are acquired as parameters representing the characteristics of the target time waveform. Note that instead of acquiring a standard deviation as a parameter, a variance may be acquired as a parameter. The same applies to the following description of acquiring a standard deviation as a parameter.

The weighted difference between the first cumulative distribution function and the second cumulative distribution function is expressed by, for example, following Formula (6) with weight of the first cumulative distribution function as $k_1$ and weight of the second cumulative distribution function as $k_2$. The function expressed by following Formula (6) is a function obtained by subtracting, from a function obtained by multiplying the first cumulative distribution function by the weight $k_1$, a function obtained by multiplying the second cumulative distribution function by the weight $k_2$.

[Math. 6]

$$k_1 f_1(x) - k_2 f_2(x) = k_1\frac{1}{2}\left(1 + \operatorname{erf}\left(\frac{x-\mu_1}{\sqrt{2\sigma_1^2}}\right)\right) - k_2\frac{1}{2}\left(1 + \operatorname{erf}\left(\frac{x-\mu_2}{\sqrt{2\sigma_2^2}}\right)\right) \tag{6}$$

That is, when the target time waveform is approximated by the approximate time waveform that is the weighted difference between the first cumulative distribution function and the second cumulative distribution function, the average $\mu_1$ and the standard deviation $\sigma_1$ that are the parameters specifying the first unimodal distribution or the parameters specifying the first cumulative distribution function, and the average $\mu_2$ and the standard deviation $\sigma_2$ that are the parameters specifying the second unimodal distribution or the parameters specifying the second cumulative distribution function are at least acquired as parameters representing the characteristics of the target time waveform. Note that the weight $k_1$ of the first cumulative distribution function and the weight $k_2$ of the second cumulative distribution function or a ratio between the weight $k_1$ of the first cumulative distribution function and the weight $k_2$ of the second cumulative distribution function ($k_1/k_2$ or $k_2/k_1$) may also be acquired as parameters representing the characteristics of the target time waveform.

In consideration that the function of Formula (6) is the function obtained by subtracting, from the function obtained by multiplying the first cumulative distribution function by the weight $k_1$, the function obtained by multiplying the second cumulative distribution function by the weight $k_2$, both the weight $k_1$ and the weight $k_2$ are positive values. However, in a case where the target heart is in a peculiar state, a possibility cannot be denied that at least one of the weight $k_1$ or the weight $k_2$ obtained by fitting is not a positive value. Thus, the signal analysis device 1 may perform fitting such that both the weight $k_1$ and the weight $k_2$ have positive values, but it is not essential to perform the fitting such that both the weight $k_1$ and the weight $k_2$ have positive values.

Note that, the signal analysis device 1 preferably sets the R wave as the first target time waveform and the T wave as the second target time waveform among the R wave and the T wave included in the waveform for one cycle of the acquired electrocardiogram of the target heart, and acquires the parameters representing the characteristics of the target time waveform described above for each of the first target time waveform and the second target time waveform.

For example, in a case where the first target time waveform (that is, the R wave) is approximated by the difference between the first cumulative distribution function and the second cumulative distribution function, the first target time waveform is approximated by an approximate time waveform of Formula (9) that is a function obtained by subtracting, from a first cumulative distribution function $f_a(x)$ expressed by Formula (7), a second cumulative distribution function $f_b(x)$ expressed by Formula (8), and an average $\mu_a$ and a standard deviation $\sigma_a$ that are parameters specifying the first cumulative distribution function, and an average $\mu_b$ and a standard deviation $\sigma_b$ that are parameters specifying the second cumulative distribution function are acquired as parameters representing the characteristics of the first target time waveform (that is, the R wave).

[Math. 7]

$$f_a(x) = \frac{1}{2}\left(1 + \mathrm{erf}\left(\frac{x - \mu_a}{\sqrt{2\sigma_a^2}}\right)\right) \tag{7}$$

[Math. 8]

$$f_b(x) = \frac{1}{2}\left(1 + \mathrm{erf}\left(\frac{x - \mu_b}{\sqrt{2\sigma_b^2}}\right)\right) \tag{8}$$

[Math. 9]

$$f_a(x) - f_b(x) = \frac{1}{2}\left(1 + \mathrm{erf}\left(\frac{x - \mu_a}{\sqrt{2\sigma_a^2}}\right)\right) - \frac{1}{2}\left(1 + \mathrm{erf}\left(\frac{x - \mu_b}{\sqrt{2\sigma_b^2}}\right)\right) \tag{9}$$

For example, in a case where the first target time waveform (that is, the R wave) is approximated by the weighted difference between the first cumulative distribution function and the second cumulative distribution function, the first target time waveform is approximated by an approximate time waveform of Formula (10) that is a function obtained by subtracting, from a function obtained by multiplying the first cumulative distribution function $f_a(x)$ expressed by Formula (7) by weight $k_a$, a function obtained by multiplying the second cumulative distribution function $f_b(x)$ expressed by Formula (8) by weight $k_b$, and the average $\mu_a$ and the standard deviation $\sigma_a$ that are the parameters specifying the first cumulative distribution function, and the average $\mu_b$ and the standard deviation $\sigma_b$ that are the parameters specifying the second cumulative distribution function are at least acquired as parameters representing the characteristics of the first target time waveform (that is, the R wave). Note that the weight $k_a$ of the first cumulative distribution function and the weight $k_b$ of the second cumulative distribution function or a ratio between the weight $k_a$ of the first cumulative distribution function and the weight $k_b$ of the second cumulative distribution function ($k_a/k_b$ or $k_b/k_a$) may also be acquired as parameters representing the characteristics of the first target time waveform (that is, the R wave).

[Math. 10]

$$k_a f_a(x) - k_b f_b(x) = k_a\frac{1}{2}\left(1 + \mathrm{erf}\left(\frac{x - \mu_a}{\sqrt{2\sigma_a^2}}\right)\right) - k_b\frac{1}{2}\left(1 + \mathrm{erf}\left(\frac{x - \mu_b}{\sqrt{2\sigma_b^2}}\right)\right) \tag{10}$$

In consideration that the function of Formula (10) is the function obtained by subtracting, from the function obtained by multiplying the first cumulative distribution function by the weight $k_a$, the function obtained by multiplying the second cumulative distribution function by the weight $k_b$, both the weight $k_a$ and the weight $k_b$ are positive values. However, in a case where the target heart is in a peculiar state, a possibility cannot be denied that at least one of the weight $k_a$ or the weight $k_c$ obtained by fitting is not a positive value. Thus, the signal analysis device 1 may perform fitting such that both the weight $k_a$ and the weight $k_b$ have positive values, but it is not essential to perform the fitting such that both the weight $k_a$ and the weight $k_b$ have positive values.

Since the R wave corresponds to a fact that excitation of all cells of the myocardium starts sequentially in accordance with a Gaussian distribution, as for the R wave, the target time waveform in the forward direction of time only needs to be approximated by an approximate time waveform of a difference or a weighted difference between two cumulative Gaussian distributions as described above. On the other hand, in consideration that the T wave corresponds to a fact that the excitation of all the cells of the myocardium sequentially fades in accordance with a Gaussian distribution, the T wave can be interpreted as a phenomenon in a reverse direction to the R wave in the time axis. That is, as for the T wave, a waveform obtained by inverting the time axis of the target time waveform only needs to be approximated by a difference or a weighted difference of cumulative Gaussian distributions. Hereinafter, this is referred to as a first method. Furthermore, in consideration that the T wave corresponds to a fact that all the cells of the myocardium fade out a state of excitation in accordance with the Gaussian distribution, it can also be said that, as for the T wave, the target time waveform in the forward direction of time only needs to be approximated by a difference or a weighted difference between two functions (functions each obtained by subtracting a cumulative Gaussian distribution from 1). Hereinafter, this is referred to as a second method. Specific examples of the first method and the second method will be described below, but in order to avoid confusion between cumulative distribution functions for the R wave described above and cumulative distribution functions for the T wave described below, in the following, the description will be given by referring to the first cumulative distribution function described above as a third cumulative distribution function, and the second cumulative distribution function described above as a fourth cumulative distribution function, as for the T wave.

In a case where the second target time waveform (that is, the T wave) is approximated by a difference between the third cumulative distribution function and the fourth cumulative distribution function by using the first method, information representing time in the reverse direction is set as x' and a waveform obtained by inverting the time axis of the second target time waveform is referred to as a second target inverse time waveform, the second target inverse time waveform is approximated by an approximate inverse time waveform of Formula (13) that is a function obtained by subtracting, from a third cumulative distribution function $f_e(x')$ expressed by Formula (11), a fourth cumulative distribution function $f_g(x')$ expressed by Formula (12), and an average $\mu_e$ and a standard deviation $\sigma_e$ that are parameters specifying the third cumulative distribution function, and an average $\mu_g$ and a standard deviation $\sigma_g$ that are parameters specifying the fourth cumulative distribution function are acquired as parameters representing the characteristics of the second target time waveform (that is, the T wave).

[Math. 11]

$$f_e(x') = \frac{1}{2}\left(1 + \mathrm{erf}\left(\frac{x' - \mu_e}{\sqrt{2\sigma_e^2}}\right)\right) \tag{11}$$

[Math. 12]

$$f_g(x') = \frac{1}{2}\left(1 + \mathrm{erf}\left(\frac{x' - \mu_g}{\sqrt{2\sigma_g^2}}\right)\right) \tag{12}$$

[Math. 13]

$$f_e(x') - f_g(x') = \frac{1}{2}\left(1 + \mathrm{erf}\left(\frac{x' - \mu_e}{\sqrt{2\sigma_e^2}}\right)\right) - \frac{1}{2}\left(1 + \mathrm{erf}\left(\frac{x' - \mu_g}{\sqrt{2\sigma_g^2}}\right)\right) \tag{13}$$

For example, in a case where the second target time waveform (that is, the T wave) is approximated by a weighted difference between the third cumulative distribution function and the fourth cumulative distribution function by using the first method, the second target inverse time waveform is approximated by an approximate inverse time waveform of Formula (14) that is a function obtained by subtracting, from a function obtained by multiplying the third cumulative distribution function $f_e(x')$ expressed by Formula (11) by weight $k_e$, a function obtained by multiplying the fourth cumulative distribution function $f_g(x')$ expressed by Formula (12) by weight $k_g$, and the average $\mu_e$ and the standard deviation de that are the parameters specifying the third cumulative distribution function, and the average $\mu_g$ and the standard deviation $\sigma_g$ that are the parameters specifying the fourth cumulative distribution function are at least acquired as parameters representing the characteristics of the second target time waveform (that is, the T wave). Note that the weight $k_e$ of the third cumulative distribution function and the weight $k_g$ of the fourth cumulative distribution function or a ratio between the weight $k_e$ of the third cumulative distribution function and the weight $k_g$ of the fourth cumulative distribution function ($k_e/k_g$ or $k_g/k_e$) may also be acquired as parameters representing the characteristics of the second target time waveform (that is, the T wave).

[Math. 14]

$$k_e f_e(x') - k_g f_g(x') = k_e\frac{1}{2}\left(1 + \mathrm{erf}\left(\frac{x' - \mu_e}{\sqrt{2\sigma_e^2}}\right)\right) - k_g\frac{1}{2}\left(1 + \mathrm{erf}\left(\frac{x' - \mu_g}{\sqrt{2\sigma_g^2}}\right)\right) \tag{14}$$

In consideration that the function of Formula (14) is the function obtained by subtracting, from the function obtained by multiplying the third cumulative distribution function by the weight $k_e$, the function obtained by multiplying the fourth cumulative distribution function by the weight $k_g$, both the weight $k_e$ and the weight $k_g$ are positive values. However, in a case where the target heart is in a peculiar state, a possibility cannot be denied that at least one of the weight $k_e$ or the weight $k_g$ obtained by fitting is not a positive value. Thus, the signal analysis device 1 may perform fitting such that both the weight $k_e$ and the weight $k_g$ have positive values, but it is not essential to perform the fitting such that both the weight $k_e$ and the weight $k_g$ have positive values.

For example, in a case where the second target time waveform (that is, the T wave) is approximated by a difference between a function $f'_c(x)$ (hereinafter, referred to as a "third inverse cumulative distribution function") obtained by subtracting, from 1, a third cumulative distribution function $f_c(x)$ expressed by Formula (15), and a function $f'_d(x)$ (hereinafter, the function is referred to as a "fourth inverse cumulative distribution function") obtained by subtracting, from 1, a fourth cumulative distribution function $f_d(x)$ expressed by Formula (16), by using the second method, the second target time waveform is approximated by an approximate time waveform of Formula (17) that is a function obtained by subtracting, from the third inverse cumulative distribution function $f'_c(x)$, the fourth inverse cumulative distribution function $f'_d(x)$, and an average $\mu_c$ and a standard deviation $\sigma_c$ that are parameters specifying the third cumulative distribution function, and an average $\mu_d$ and a standard deviation od that are parameters specifying the fourth cumulative distribution function are acquired as parameters representing the characteristics of the second target time waveform (that is, the T wave).

[Math. 15]

$$f_c(x) = \frac{1}{2}\left(1 + \mathrm{erf}\left(\frac{x - \mu_c}{\sqrt{2\sigma_c^2}}\right)\right) \tag{15}$$

[Math. 16]

$$f_d(x) = \frac{1}{2}\left(1 + \mathrm{erf}\left(\frac{x - \mu_d}{\sqrt{2\sigma_d^2}}\right)\right) \tag{16}$$

[Math. 17]

$$\begin{aligned} f'_c(x) - f'_d(x) &= (1 - f_c(x)) - (1 - f_d(x)) \\ &= f_d(x) - f_c(x) \\ &= \frac{1}{2}\left(1 + \mathrm{erf}\left(\frac{x - \mu_d}{\sqrt{2\sigma_d^2}}\right)\right) - \\ &\quad \frac{1}{2}\left(1 + \mathrm{erf}\left(\frac{x - \mu_c}{\sqrt{2\sigma_c^2}}\right)\right) \end{aligned} \tag{17}$$

For example, in a case where the second target time waveform (that is, the T wave) is approximated by a weighted difference between the third inverse cumulative distribution function and the fourth inverse cumulative distribution function by using the second method, the second target time waveform is approximated by an approximate time waveform of Formula (18) that is a function obtained by subtracting, from a function obtained by multiplying the third inverse cumulative distribution function $f'_c(x)$ by weight $k_c$, a function obtained by multiplying the fourth inverse cumulative distribution function $f'_d(x)$ by weight $k_d$, and the average uc and the standard deviation $\sigma_f$ that are the parameters specifying the third cumulative distribution function, and the average $\mu_d$ and the standard deviation od that are the parameters specifying the fourth cumulative distribution function are acquired as parameters representing the characteristics of the second target time waveform (that is, the T wave). Note that the weight $k_c$ of the third inverse cumulative distribution function and the weight $k_d$ of the fourth inverse cumulative distribution function or a ratio between the weight $k_c$ of the third inverse cumulative distribution function and the weight $k_d$ of the fourth inverse cumulative distribution function ($k_c/k_d$ or $k_d/k_c$) may also be acquired as parameters representing the characteristics of the second target time waveform (that is, the T wave).

[Math. 18]

$$\begin{aligned} k_c f_c'(x) - k_d f_d'(x) &= k_c(1 - f_c(x)) - k_d(1 - f_d(x)) \\ &= k_d f_d(x) - k_c f_c(x) + k_c - k_d \\ &= k_d \frac{1}{2}\left(1 + \mathrm{erf}\left(\frac{x - \mu_d}{\sqrt{2\sigma_d^2}}\right)\right) - \\ &\quad k_c \frac{1}{2}\left(1 + \mathrm{erf}\left(\frac{x - \mu_c}{\sqrt{2\sigma_c^2}}\right)\right) + k_c - k_d \end{aligned} \tag{18}$$

In consideration that the function of Formula (18) is the function obtained by subtracting, from the function obtained by multiplying the third inverse cumulative distribution function by the weight $k_c$, the function obtained by multiplying the fourth inverse cumulative distribution function by the weight $k_d$, both the weight $k_c$ and the weight $k_d$ are positive values. However, in a case where the target heart is in a peculiar state, a possibility cannot be denied that at least one of the weight $k_c$ or the weight $k_d$ obtained by fitting is not a positive value. Thus, the signal analysis device 1 may perform fitting such that both the weight $k_c$ and the weight $k_d$ have positive values, but it is not essential to perform the fitting such that both the weight $k_c$ and the weight $k_d$ have positive values.

Note that the approximate time waveform of Formula (17) is a function obtained by subtracting, from the fourth cumulative distribution function $f_d(x)$, the third cumulative distribution function $f_c(x)$, and thus, is a difference between the third cumulative distribution function $f_c(x)$ and the fourth cumulative distribution function $f_d(x)$. Furthermore, the approximate time waveform of Formula (18) is obtained by adding a constant term to a weighted difference between the third cumulative distribution function $f_c(x)$ and the fourth cumulative distribution function $f_d(x)$, and a shape of a curved portion is the same as the weighted difference between the third cumulative distribution function $f_c(x)$ and the fourth cumulative distribution function $f_d(x)$. Furthermore, as described above, the T wave can be interpreted as a phenomenon in the reverse direction to the R wave in the time axis, and as for the T wave, the waveform obtained by inverting the time axis of the target time waveform can be approximated by a difference or a weighted difference between a third cumulative distribution function $f_e(x)$ and a fourth cumulative distribution function $f_g(x)$. For these reasons, in the following description of the T wave, a cumulative distribution function and an inverse cumulative distribution function are not described together, and only the cumulative distribution function may be simply used.

Figure 2:
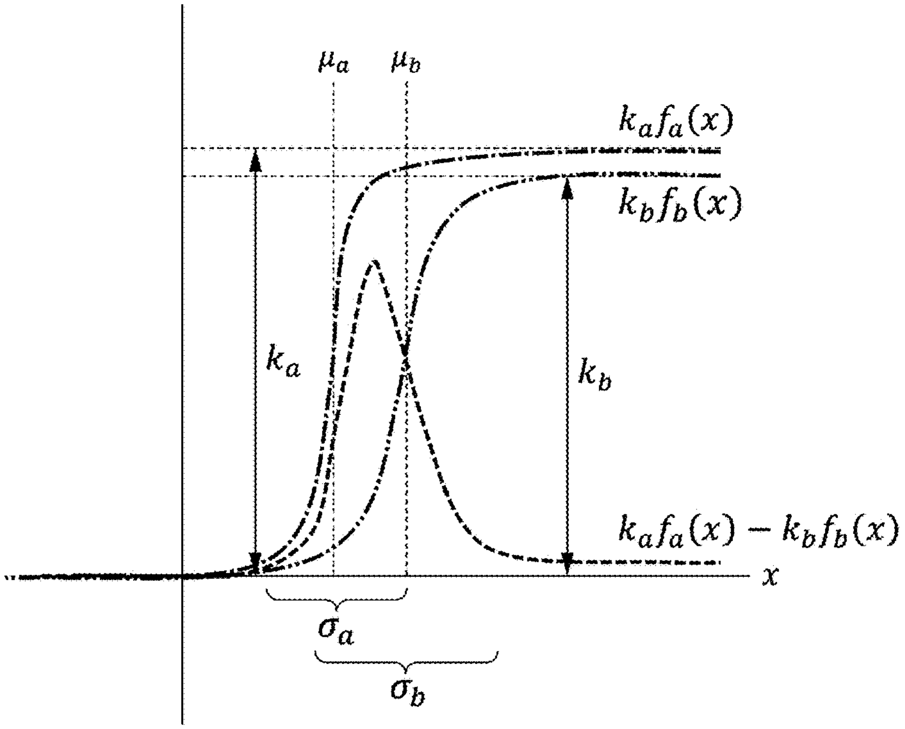
FIG. 2 is a diagram schematically illustrating a function obtained by multiplying a first cumulative distribution function by weight, a function obtained by multiplying a second cumulative distribution function by weight, and an approximate time waveform that is a weighted difference between the first cumulative distribution function and the second cumulative distribution function, for a first target time waveform.

FIG. 2 is a diagram schematically illustrating a function $k_a f_a(x)$ obtained by multiplying the first cumulative distribution function $f_a(x)$ by the weight $k_a$, a function $k_b f_b(x)$ obtained by multiplying the second cumulative distribution function $f_b(x)$ by the weight $k_b$, and an approximate time waveform $k_a f_a(x) - k_b f_b(x)$ that is the weighted difference between the first cumulative distribution function and the second cumulative distribution function, for the first target time waveform (that is, the R wave). A one-dot chain line is the function $k_a f_a(x)$ obtained by multiplying the first cumulative distribution function $f_a(x)$ by the weight $k_a$, a two-dot chain line is the function $k_b f_b(x)$ obtained by multiplying the second cumulative distribution function $f_b(x)$ by the weight $k_b$, and a broken line is the approximate time waveform $k_a f_a(x) - k_b f_b(x)$. The approximate time waveform $k_a f_a(x) - k_b f_b(x)$ is a waveform approximating the first target time waveform (that is, the R wave).

Figure 3:
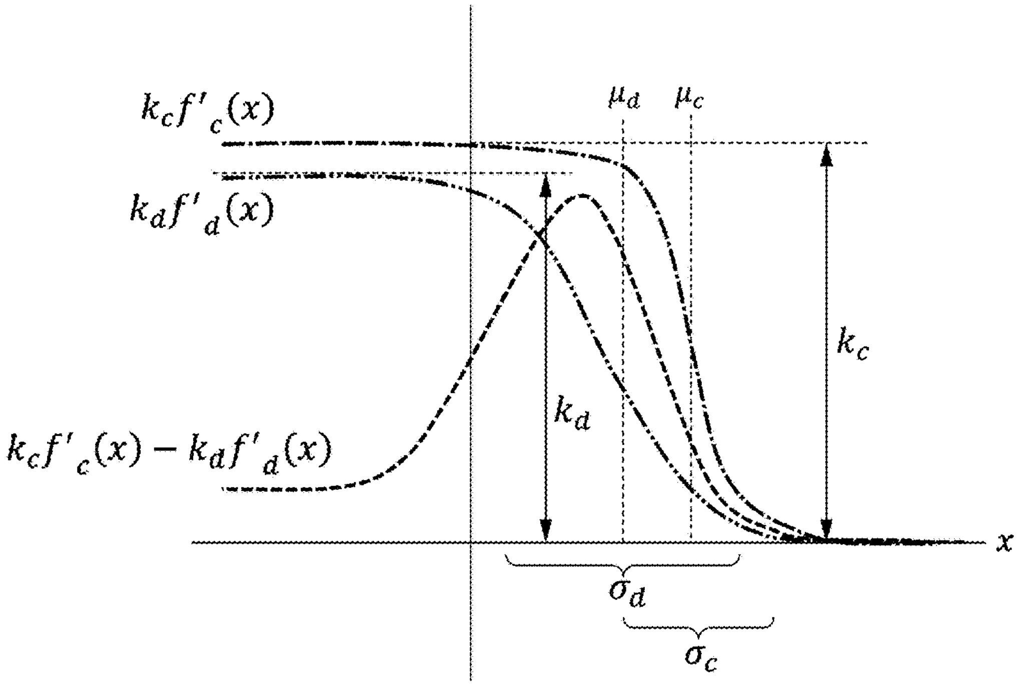
FIG. 3 is a diagram schematically illustrating a function obtained by multiplying a third inverse cumulative distribution function by weight, a function obtained by multiplying a fourth inverse cumulative distribution function by weight, and an approximate time waveform that is a weighted difference between the third inverse cumulative distribution function and the fourth inverse cumulative distribution function, for a second target time waveform.

FIG. 3 is a diagram schematically illustrating a function $k_c f'_c(x)$ obtained by multiplying the third inverse cumulative distribution function $f'_c(x) = 1 - f_c(x)$ by the weight $k_c$, a function $k_d f'_d(x)$ obtained by multiplying the fourth inverse cumulative distribution function $f'_d(x) = 1 - f_d(x)$ by the weight $k_d$, and an approximate time waveform $k_c f'_c(x) - k_d f'_d(x)$ that is the weighted difference between the third inverse cumulative distribution function and the fourth inverse cumulative distribution function, for the second target time waveform (that is, the T wave). A one-dot chain line is the function $k_c f'_c(x)$ obtained by multiplying the third inverse cumulative distribution function $f'_c(x) = 1 - f_c(x)$ by the weight $k_c$, a two-dot chain line is the function $k_d f'_d(x)$ obtained by multiplying the fourth inverse cumulative distribution function $f'_d(x) = 1 - f_d(x)$ by the weight $k_d$, and a broken line is the approximate time waveform $k_c f'_c(x) - k_d f'_d(x)$. The approximate time waveform $k_c f'_c(x) - k_d f'_d(x)$ is a waveform approximating the second target time waveform (that is, the T wave).

Figure 4:
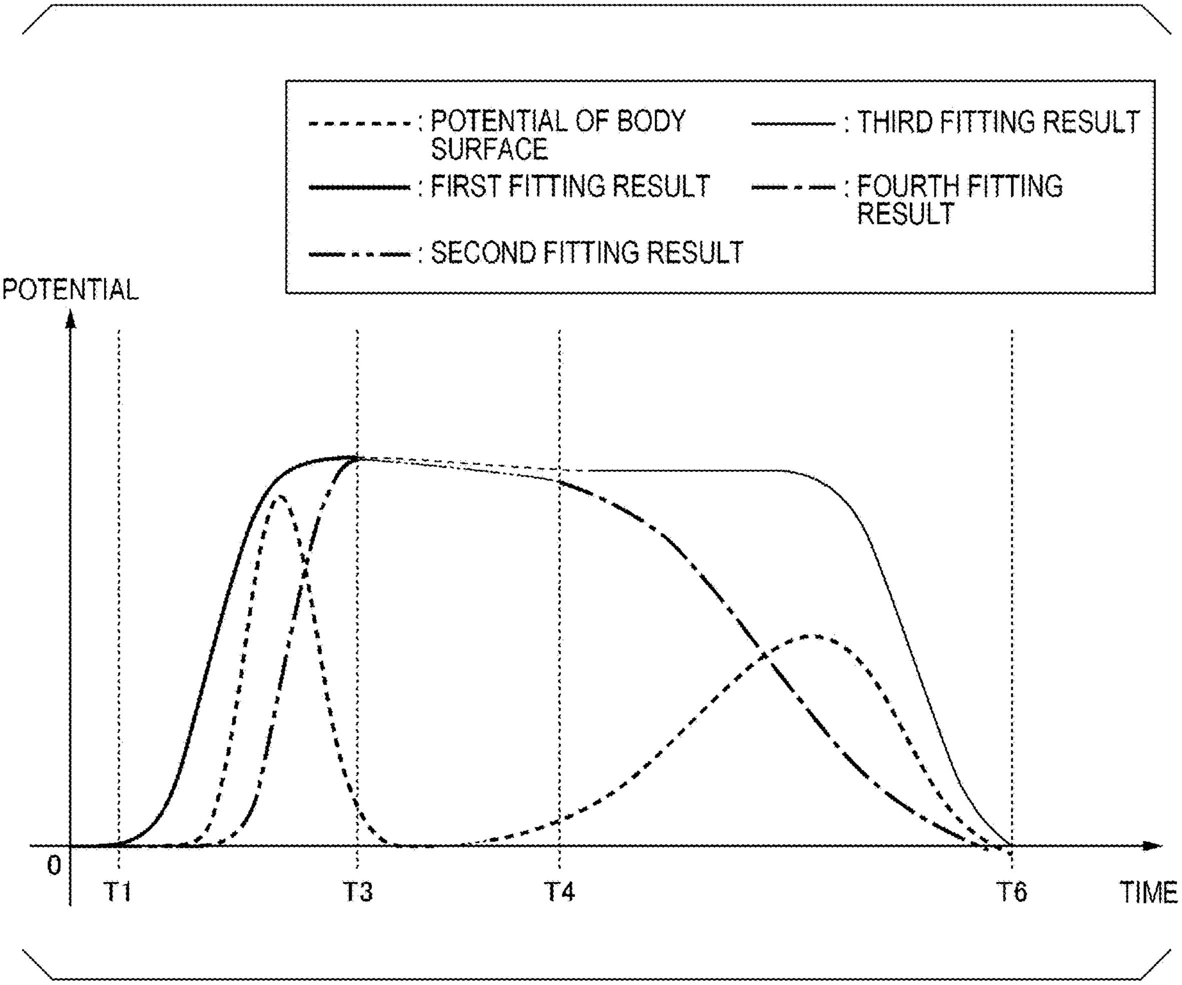
FIG. 4 is a diagram illustrating an example of results of fitting a waveform of an electrocardiogram of a target heart by four cumulative distribution functions in the first embodiment.

FIG. 4 is a diagram schematically illustrating results of fitting each of the first target time waveform and the second target time waveform represented by a difference between two cumulative distribution functions, with the R wave included in the waveform for one cycle of the electrocardiogram of the target heart in the first embodiment as the first target time waveform and the T wave as the second target time waveform. In FIG. 4, the horizontal axis represents time and the vertical axis represents a potential. Units of both the horizontal axis and the vertical axis are all arbitrary units.

Specifically, FIG. 4 illustrates an example in which the first target time waveform (that is, the R wave) is fitted by the difference between the first cumulative distribution function and the second cumulative distribution function, and the second target time waveform (that is, the T wave) is fitted by the difference between the third cumulative distribution function and the fourth cumulative distribution function. A domain of the first cumulative distribution function and a domain of the second cumulative distribution function are the same, and are from time T1 to time T3, which is the time section of the first target time waveform (that is, the R wave). A domain of the third cumulative distribution function and a domain of the fourth cumulative distribution function are the same, and are from time T4 to time T6.

A “first fitting result” and a “second fitting result” in FIG. 4 are results of fitting to the R wave. A “third fitting result” and a “fourth fitting result” in FIG. 4 are results of fitting to the T wave.

In FIG. 4, the “first fitting result” indicates the first cumulative distribution function among the results of fitting to the first target time waveform (that is, the R wave) of the electrocardiogram. In FIG. 4, the “second fitting result” indicates the second cumulative distribution function among the results of fitting to the first target time waveform (that is, the R wave) of the electrocardiogram. In FIG. 4, the “third fitting result” indicates the third cumulative distribution function among the results of fitting to the second target time waveform (that is, the T wave) of the electrocardiogram. In FIG. 4, the "fourth fitting result" indicates the fourth cumulative distribution function among the results of fitting to the second target time waveform (that is, the T wave) of the electrocardiogram. In FIG. 4, "potential of body surface" represents a waveform of the electrocardiogram to be fitted.

Note that the signal analysis device 1 does not perform fitting for a period from the time T3 to the time T4 that does not belong to the time section of the first target time waveform (that is, the R wave) or the time section of the second target time waveform (that is, the T wave). Note that, for the period in which fitting is not performed in the signal analysis device 1, in FIG. 4, expression is performed by a line connecting the first fitting result at the time T3 to the third fitting result at the time T4, and a line connecting the second fitting result at the time T3 to the fourth fitting result at the time T4. That is, in a case where the signal analysis device 1 displays the fitting results, as illustrated in FIG. 4, the signal analysis device 1 only needs to display lines respectively connecting the first fitting result at the time T3 and the third fitting result at the time T4 together and the second fitting result at the time T3 and the fourth fitting result at the time T4 together by predetermined functions such as constant functions or linear functions.

Note that in a case where the signal analysis device 1 displays the fitting results, a value of the weight may be corrected so that the first fitting result at the time T3 and the third fitting result at the time T4 can be displayed using the same value. That is, although the actual first fitting result at the time T3 is $k_a f_a$ (T3) and the actual third fitting result at the time T4 is $k_c f'_c$ (T4), $\alpha_1$ that satisfies $k_a f_a (T3)=\alpha_1 k_c f'_c (T4)$ may be obtained and the fitting results may be displayed using $\alpha_1 k_c$ instead of the weight $k_c$, or the fitting results may be displayed using $k_a/\alpha_1$ instead of the weight $k_a$. Similarly, in a case where the signal analysis device 1 displays the fitting results, a value of the weight may be corrected so that the second fitting result at the time T3 and the fourth fitting result at the time T4 can be displayed using the same value. That is, although the second fitting result at the time T3 is $k_b f_b$ (T3) and the fourth fitting result at the time T4 is $k_d f'_d$ (T4), $\alpha_2$ that satisfies $k_b f_b (T3)=\alpha_2 k_d f'_d (T4)$ is obtained and the fitting results may be displayed using $\alpha_2 k_d$ instead of the weight $k_d$, or the fitting results may be displayed using $k_b/\alpha_2$ instead of the weight $k_b$.

Note that fitting to the first target time waveform and fitting to the second target time waveform may not be executed individually. That is, fitting to the first target time waveform and the second target time waveform may be collectively executed as fitting to both the first target time waveform and the second target time waveform. For example, in a case where the fitting to the first target time waveform and the second target time waveform is collectively performed, the signal analysis device 1 preferably executes fitting in consideration of reducing a difference between the first fitting result at the time T3 and the third fitting result at the time T4 and reducing a difference between the second fitting result at the time T3 and the fourth fitting result at the time T4.

Figure 5:
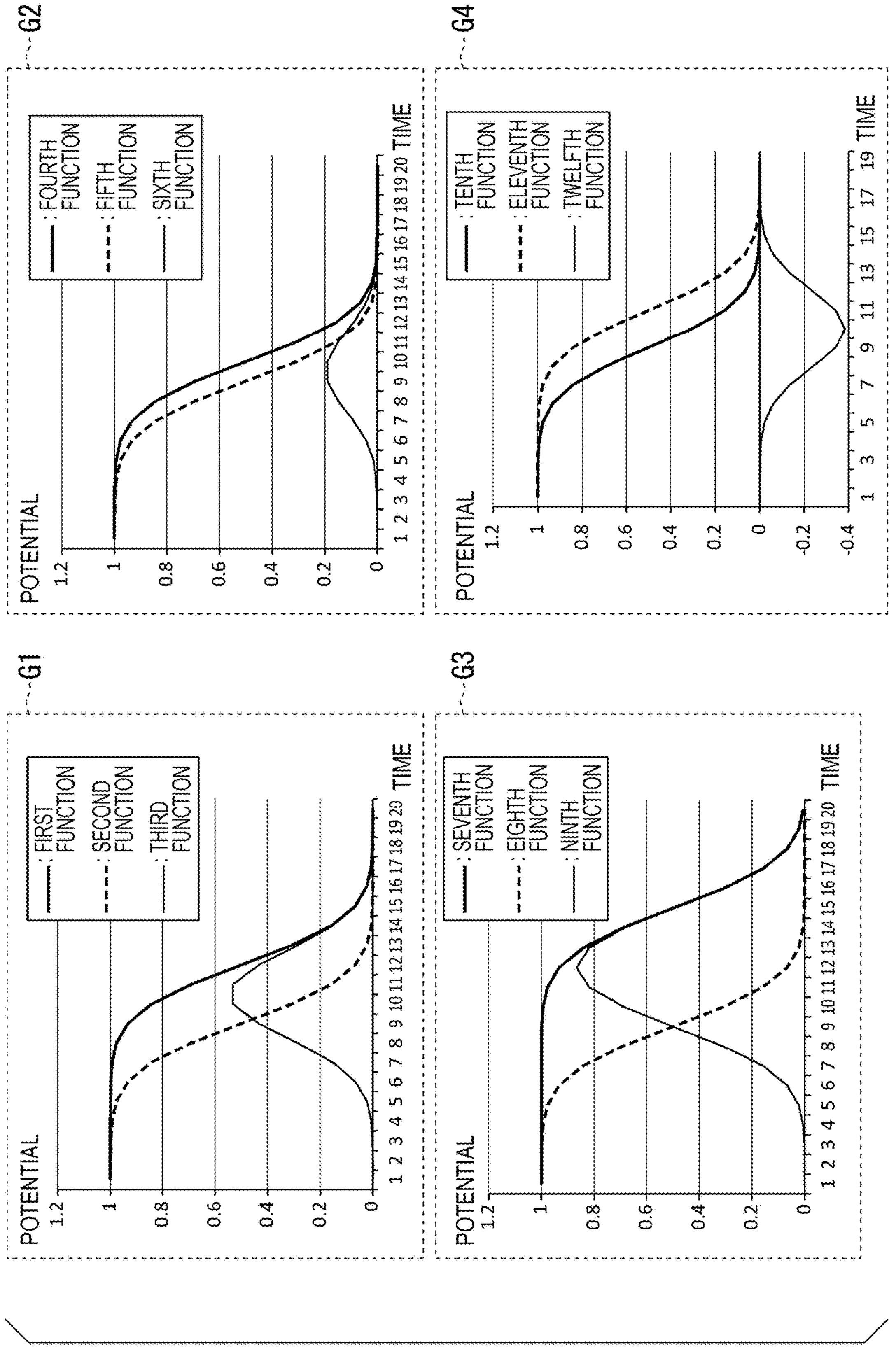
FIG. 5 is an explanatory diagram describing that a difference between two cumulative distribution functions in the first embodiment can be fitted to substantially the same waveform as a falling waveform of a T wave.

FIG. 5 is an explanatory diagram describing that it is possible to visualize typical characteristics of the T wave by approximating the T wave by a function obtained by subtracting the fourth inverse cumulative distribution function from the third inverse cumulative distribution function, and displaying the third inverse cumulative distribution function and the fourth inverse cumulative distribution function or displaying the parameters specifying the respective cumulative distribution functions. FIG. 5 illustrates four images of an image G1, an image G2, an image G3, and an image G4. Each of the images G1 to G4 illustrates a graph in which the horizontal axis represents time and the vertical axis represents a potential. Units of the horizontal axis and the vertical axis of each of the images G1 to G4 in FIG. 5 are all arbitrary units.

A "first function" in FIG. 5 is an example of the third inverse cumulative distribution function. A "second function" in FIG. 5 is an example of the fourth inverse cumulative distribution function. A "third function" in FIG. 5 represents a function obtained by subtracting the "second function" from the "first function", that is, a function obtained by subtracting the fourth inverse cumulative distribution function from the third inverse cumulative distribution function. The "third function" in FIG. 5 has substantially the same shape as a shape of the T wave of a normal heart.

A "fourth function" in FIG. 5 is an example of the third inverse cumulative distribution function. A "fifth function" in FIG. 5 is an example of the fourth inverse cumulative distribution function. A "sixth function" in FIG. 5 represents a function obtained by subtracting the "fifth function" from the "fourth function", that is, a function obtained by subtracting the fourth inverse cumulative distribution function from the third inverse cumulative distribution function. The "sixth function" in FIG. 5 has substantially the same shape as a shape of decrease in height of the T wave of one of three typical abnormal patterns of the T wave. An interval between a falling portion of the third inverse cumulative distribution function and a falling portion of the fourth inverse cumulative distribution function in the image G2 in FIG. 5 is narrower than an interval between a falling portion of the third inverse cumulative distribution function and a falling portion of the fourth inverse cumulative distribution function in the image G1 of the normal heart, whereby it is visualized that delay of the activity of the myocardial outer layer from the activity of the myocardial inner layer is small in the decrease in height of the T wave.

A "seventh function" in FIG. 5 is an example of the third inverse cumulative distribution function. An "eighth function" in FIG. 5 is an example of the fourth inverse cumulative distribution function. A "ninth function" in FIG. 5 represents a function obtained by subtracting the "eighth function" from the "seventh function", that is, a function obtained by subtracting the fourth inverse cumulative distribution function from the third inverse cumulative distribution function. The "ninth function" in FIG. 5 has substantially the same shape as a shape of increase in height of the T wave of one of the three typical abnormal patterns of the T wave. An interval between a falling portion of the third inverse cumulative distribution function and a falling portion of the fourth inverse cumulative distribution function in the image G3 in FIG. 5 is wider than the interval between the falling portion of the third inverse cumulative distribution function and the falling portion of the fourth inverse cumulative distribution function in the image G1 of the normal heart, whereby it is visualized that delay of activity of the myocardial outer layer from activity of the myocardial inner layer is large in the increase in height of the T wave.

A "tenth function" in FIG. 5 is an example of the third inverse cumulative distribution function. An "eleventh function" in FIG. 5 is an example of the fourth inverse cumulative distribution function. A "twelfth function" in FIG. 5 represents a function obtained by subtracting the "eleventh function" from the "tenth function", that is, a function obtained by subtracting the fourth inverse cumulative distribution function from the third inverse cumulative distribution function. The "twelfth function" in FIG. 5 has substantially the same shape as a shape of a negative T wave of one of the three typical abnormal patterns of the T wave. The order of a falling portion of the third inverse cumulative distribution function and a falling portion of the fourth inverse cumulative distribution function in the image G4 in FIG. 5 is opposite to the order of the falling portion of the third inverse cumulative distribution function and the falling portion of the fourth inverse cumulative distribution function in the image G1 of the normal heart, whereby it is visualized that the myocardial outer layer ends activity earlier than the myocardial inner layer in the negative T wave.

The function obtained by subtracting the fourth inverse cumulative distribution function from the third inverse cumulative distribution function can express waves having different widths in the vertical axis direction and in the horizontal axis direction, such as the "third function", the "sixth function", and the "ninth function". Furthermore, the function obtained by subtracting the fourth inverse cumulative distribution function from the third inverse cumulative distribution function can express a negative wave such as the "twelfth function". That is, the T wave is approximated by the function obtained by subtracting the fourth inverse cumulative distribution function from the third inverse cumulative distribution function, or the T wave is approximated by a function obtained by inverting the time axis and subtracting the fourth cumulative distribution function from the third cumulative distribution function, whereby it is possible to express activity of each of the myocardial inner layer and the myocardial outer layer included in the T wave and a relationship between the activity of the myocardial inner layer and the activity of the myocardial outer layer. The same applies to a case where the R wave is approximated by the function obtained by subtracting the second cumulative distribution function from the first cumulative distribution function.

As described above, the signal analysis device 1 performs fitting for a waveform of the R wave or the T wave of the electrocardiogram of the target heart by a difference or a weighted difference between two cumulative distribution functions. Then, the signal analysis device 1 acquires a parameter specifying the approximate time waveform specified by fitting as the parameter indicating the activity of the myocardium.

[Approximation by Addition of Value and Difference or Weighted Difference Between Two Cumulative Distribution Functions]

The signal analysis device 1 may set, as the target time waveform, the waveform in the time section of any of the R wave or the T wave included in the waveform for one cycle of the acquired electrocardiogram of the target heart, and set, as the approximate time waveform, a time waveform represented by addition of a value (hereinafter, the value is referred to as a "level value") and the difference or the weighted difference between the first cumulative distribution function that is a cumulative distribution function of the first unimodal distribution and the second cumulative distribution function that is a cumulative distribution function of the second unimodal distribution. In this case, in addition to the parameter specifying the first unimodal distribution or the parameter specifying the first cumulative distribution function and the parameter specifying the second unimodal distribution or the parameter specifying the second cumulative distribution function when the target time waveform is approximated by the approximate time waveform, the level value is also acquired as a parameter representing the characteristics of the target time waveform. Of course, in a case where approximation is performed by the weighted difference, the weight given to the first cumulative distribution function and the weight given to the second cumulative distribution function may also be acquired as parameters representing the characteristics of the target time waveform, or the ratio between the weight given to the first cumulative distribution function and the weight given to the second cumulative distribution function may also be acquired as the parameter representing the characteristics of the target time waveform.

In a case where the weighted difference is used, for example, the signal analysis device 1 uses each of combinations (J×K×L×M×N) of parameters specifying cumulative distribution functions for a respective plurality of (M) candidates for the first cumulative distribution function, parameters specifying cumulative distribution functions for a respective plurality of (N) candidates for the second cumulative distribution function, a plurality of (K) candidates for the weight given to the first cumulative distribution function, a plurality of (L) candidates for the weight given to the second cumulative distribution function, and a plurality of (J) candidates for the level value, to generate a candidate time waveform that is a time waveform represented by addition of the level value and the weighted difference between the first cumulative distribution function and the second cumulative distribution function, specifies, as the approximate time waveform, a candidate time waveform closest to the target time waveform among generated J×K×L×M×N candidate time waveforms, and acquires, as parameters representing the characteristics of the target time waveform, a parameter specifying a candidate for the first cumulative distribution function, a parameter specifying a candidate for the second cumulative distribution function, weight given to the first cumulative distribution function, weight given to the second cumulative distribution function, and a level value used for generation of the specified approximate time waveform.

Alternatively, for example, the signal analysis device 1 repeats obtaining a candidate time waveform that is a time waveform represented by addition of a level value and a weighted difference between the candidate for the first cumulative distribution function and the candidate for the second cumulative distribution function and that approximates the target time waveform, and updating at least any of parameters specifying respective cumulative distribution functions, pieces of weight given to respective cumulative distribution functions, and the level value in a direction in which the square error between the candidate time waveform and the target time waveform decreases, until the square error is less than or equal to a predetermined standard, or a predetermined number of times, to specify a finally obtained candidate time waveform as the approximate time waveform, and acquires, as parameters representing the characteristics of the target time waveform, a parameter specifying a candidate for the first cumulative distribution function, a parameter specifying a candidate for the second cumulative distribution function, weight given to the first cumulative distribution function, weight given to the second cumulative distribution function, and a level value used for generation of the specified approximate time waveform.

Note that the level value may be determined before fitting. In this case, the signal analysis device 1 first acquires a potential at the start edge (corresponding to the time T1 in FIG. 4) of the target time waveform as the level value in a case where the target time waveform is the R wave, and acquires a potential at the end edge (corresponding to the time T6 in FIG. 4) of the target time waveform as the level value in a case where the target time waveform is the T wave. Then, the signal analysis device 1 uses each of combinations (K×L×M×N) of parameters specifying cumulative distribution functions for a respective plurality of (M) candidates for the first cumulative distribution function, parameters specifying cumulative distribution functions for a respective plurality of (N) candidates for the second cumulative distribution function, a plurality of (K) candidates for the weight given to the first cumulative distribution function, and a plurality of (L) candidates for the weight given to the second cumulative distribution function, to generate a candidate time waveform that is a time waveform represented by addition of the level value and the weighted difference between the first cumulative distribution function and the second cumulative distribution function, specifies, as the approximate time waveform, a candidate time waveform closest to the target time waveform among generated K×L×M×N candidate time waveforms, and acquires, as parameters representing the characteristics of the target time waveform, a parameter specifying a candidate for the first cumulative distribution function, a parameter specifying a candidate for the second cumulative distribution function, weight given to the first cumulative distribution function, and weight given to the second cumulative distribution function used for generation of the specified approximate time waveform, and the level value determined in the first processing.

Alternatively, for example, the signal analysis device 1 first acquires a potential at the start edge (corresponding to the time T1 in FIG. 4) of the target time waveform as the level value in a case where the target time waveform is the R wave, and acquires a potential at the end edge (corresponding to the time T6 in FIG. 4) of the target time waveform as the level value in a case where the target time waveform is the T wave. Then, the signal analysis device 1 repeats obtaining a candidate time waveform that is a time waveform represented by addition of a level value and a weighted difference between the candidate for the first cumulative distribution function and the candidate for the second cumulative distribution function and that approximates the target time waveform, and updating at least any of parameters specifying respective cumulative distribution functions and pieces of weight given to respective cumulative distribution functions in a direction in which the square error between the candidate time waveform and the target time waveform decreases, until the square error is less than or equal to a predetermined standard, or a predetermined number of times, to specify a finally obtained candidate time waveform as the approximate time waveform, and acquires, as parameters representing the characteristics of the target time waveform, a parameter specifying a candidate for the first cumulative distribution function, a parameter specifying a candidate for the second cumulative distribution function, weight given to the first cumulative distribution function, and weight given to the second cumulative distribution function used for generation of the specified approximate time waveform, and the level value determined in the first processing.

When the level value is β, addition of the level value and the weighted difference between the first cumulative distribution function and the second cumulative distribution function is expressed by, for example, following Formula (19). The function expressed by following Formula (19) is a function obtained by subtracting, from a function obtained by multiplying the first cumulative distribution function by the weight $k_1$, a function obtained by multiplying the second cumulative distribution function by the weight $k_2$, and adding the level value β.

[Math. 19]

$$k_1 f_1(x) - k_2 f_2(x) + \beta = k_1 \frac{1}{2}\left(1 + \mathrm{erf}\left(\frac{x-\mu_1}{\sqrt{2\sigma_1^2}}\right)\right) - k_2 \frac{1}{2}\left(1 + \mathrm{erf}\left(\frac{x-\mu_2}{\sqrt{2\sigma_2^2}}\right)\right) + \beta \tag{19}$$

When the target time waveform is approximated by an approximate time waveform of Formula (19) obtained by adding the level value to the weighted difference between the first cumulative distribution function and the second cumulative distribution function, the average $\mu_1$ and the standard deviation $\sigma_1$ that are the parameters specifying the first unimodal distribution or the parameters specifying the first cumulative distribution function, the average $\mu_2$ and the standard deviation $\sigma_2$ that are the parameters specifying the second unimodal distribution or the parameters specifying the second cumulative distribution function, and the level value β are at least acquired as parameters representing the characteristics of the target time waveform. Note that the weight $k_1$ of the first cumulative distribution function and the weight $k_2$ of the second cumulative distribution function or a ratio between the weight $k_1$ of the first cumulative distribution function and the weight $k_2$ of the second cumulative distribution function ($k_1/k_2$ or $k_2/k_1$) may also be acquired as parameters representing the characteristics of the target time waveform.

In consideration that the function of Formula (19) is the function obtained by subtracting, from the function obtained by multiplying the first cumulative distribution function by the weight $k_1$, the function obtained by multiplying the second cumulative distribution function by the weight $k_2$, and adding the level value β, both the weight $k_1$ and the weight $k_2$ are positive values. However, in a case where the target heart is in a peculiar state, a possibility cannot be denied that at least one of the weight $k_1$ or the weight $k_2$ obtained by fitting is not a positive value. Thus, the signal analysis device 1 may perform fitting such that both the weight $k_1$ and the weight $k_2$ have positive values, but it is not essential to perform the fitting such that both the weight $k_1$ and the weight $k_2$ have positive values.

The signal analysis device 1 preferably sets the R wave as the first target time waveform and the T wave as the second target time waveform among the R wave and the T wave included in the waveform for one cycle of the acquired electrocardiogram of the target heart, and acquires the parameters representing the characteristics of the target time waveform described above for each of the first target time waveform and the second target time waveform.

For example, in a case where the first target time waveform (that is, the R wave) is approximated by the function obtained by adding the level value to the weighted difference between the first cumulative distribution function and the second cumulative distribution function, a potential at the start edge of the first target time waveform is set as a level value $\beta_R$, the first target time waveform is approximated by an approximate time waveform of Formula (20) that is a function obtained by subtracting, from the function obtained by multiplying the first cumulative distribution function $f_a(x)$ expressed by Formula (7) by the weight $k_a$, the function obtained by multiplying the second cumulative distribution function $f_b(x)$ expressed by Formula (8) by the weight $k_b$, and adding the level value $\beta_R$, and the average $\mu_a$ and the standard deviation $\sigma_a$ that are the parameters specifying the first cumulative distribution function, the average $\mu_b$ and the standard deviation $\sigma_b$ that are the parameters specifying the second cumulative distribution function, and the level value $\beta_R$ are at least acquired as parameters representing the characteristics of the first target time waveform (that is, the R wave). Note that the weight $k_a$ of the first cumulative distribution function and the weight $k_b$ of the second cumulative distribution function or a ratio between the weight $k_a$ of the first cumulative distribution function and the weight $k_b$ of the second cumulative distribution function ($k_a/k_b$ or $k_b/k_a$) may also be acquired as parameters representing the characteristics of the first target time waveform (that is, the R wave).

[Math. 20]

$$k_a f_a(x) - k_b f_b(x) + \beta_R = k_a \frac{1}{2}\left(1 + \mathrm{erf}\left(\frac{x-\mu_a}{\sqrt{2\sigma_a^2}}\right)\right) - k_b \frac{1}{2}\left(1 + \mathrm{erf}\left(\frac{x-\mu_b}{\sqrt{2\sigma_b^2}}\right)\right) + \beta_R \tag{20}$$

In consideration that the function of Formula (20) is the function obtained by subtracting, from the function obtained by multiplying the first cumulative distribution function by the weight $k_a$, the function obtained by multiplying the second cumulative distribution function by the weight $k_b$, and adding the level value $\beta_R$, both the weight $k_a$ and the weight $k_b$ are positive values. However, in a case where the target heart is in a peculiar state, a possibility cannot be denied that at least one of the weight $k_a$ or the weight $k_b$ obtained by fitting is not a positive value. Thus, the signal analysis device 1 may perform fitting such that both the weight $k_a$ and the weight $k_b$ have positive values, but it is not essential to perform the fitting such that both the weight $k_a$ and the weight $k_b$ have positive values.

For example, in a case where the second target inverse time waveform that is the waveform obtained by inverting the time axis of the second target time waveform (that is, the T wave) is approximated by a function obtained by adding the level value to the weighted difference between the third cumulative distribution function and the fourth cumulative distribution function, a potential at the end edge of the second target time waveform is set as a level value βT, the second target inverse time waveform is approximated by an approximate inverse time waveform of Formula (21) that is a function obtained by subtracting, from the function obtained by multiplying the third cumulative distribution function $f_e(x')$ expressed by Formula (11) by the weight $k_e$, the function obtained by multiplying the fourth cumulative distribution function $f_g(x')$ expressed by Formula (12) by the weight $k_g$, and adding the level value BI, and the average pe and the standard deviation de that are the parameters specifying the third cumulative distribution function, the average $\mu_g$ and the standard deviation $\sigma_g$ that are the parameters specifying the fourth cumulative distribution function, and the level value $\beta_T$ are at least acquired as parameters representing the characteristics of the second target time waveform (that is, the T wave). Note that the weight $k_e$ of the third cumulative distribution function and the weight $k_g$ of the fourth cumulative distribution function or the ratio between the weight $k_e$ of the third cumulative distribution function and the weight $k_g$ of the fourth cumulative distribution function ($k_e/k_g$ or $k_g/k_e$) may also be acquired as parameters representing the characteristics of the second target time waveform (that is, the T wave).

[Math. 21]

$$k_e f_e(x') - k_g f_g(x') + \beta_T = k_e \frac{1}{2}\left(1 + \mathrm{erf}\left(\frac{x'-\mu_e}{\sqrt{2\sigma_e^2}}\right)\right) - k_g \frac{1}{2}\left(1 + \mathrm{erf}\left(\frac{x'-\mu_g}{\sqrt{2\sigma_g^2}}\right)\right) + \beta_T \tag{21}$$

In consideration that the function of Formula (21) is the function obtained by subtracting, from the function obtained by multiplying the third cumulative distribution function by the weight $k_e$, the function obtained by multiplying the fourth cumulative distribution function by the weight $k_g$, and adding the level value BI, both the weight $k_e$ and the weight $k_g$ are positive values. However, in a case where the target heart is in a peculiar state, a possibility cannot be denied that at least one of the weight $k_e$ or the weight $k_g$ obtained by fitting is not a positive value. Thus, the signal analysis device 1 may perform fitting such that both the weight $k_e$ and the weight $k_g$ have positive values, but it is not essential to perform the fitting such that both the weight $k_e$ and the weight $k_g$ have positive values.

For example, in a case where the second target time waveform (that is, the T wave) is approximated by a function obtained by adding the level value to a weighted difference between a function obtained by subtracting the third cumulative distribution function from 1 (that is, the third inverse cumulative distribution function) and a function obtained by subtracting the fourth cumulative distribution function from 1 (that is, the fourth inverse cumulative distribution function), the potential at the end edge of the second target time waveform is set as the level value βT, the second target time waveform is approximated by an approximate time waveform of Formula (22) that is a function obtained by subtracting, from the function obtained by multiplying the third inverse cumulative distribution function $f'_c(x)$ by the weight kor the function obtained by multiplying the fourth inverse cumulative distribution function $f'_d(x)$ by the weight $k_c$, and adding the level value $\beta_T$, and the average $\mu_c$ and the standard deviation $\sigma_c$ that are the parameters specifying the third cumulative distribution function, the average $\mu_d$ and the standard deviation $\sigma_d$ that are the parameters specifying the fourth cumulative distribution function, and the level value $\beta_T$ are acquired as parameters representing the characteristics of the second target time waveform (that is, the T wave). Note that the weight $k_c$ of the third inverse cumulative distribution function and the weight $k_d$ of the fourth inverse cumulative distribution function or a ratio between the weight $k_c$ of the third inverse cumulative distribution function and the weight $k_d$ of the fourth inverse cumulative distribution function ($k_c/k_d$ or $k_d/k_c$) may also be acquired as parameters representing the characteristics of the second target time waveform (that is, the T wave).

[Math. 22]

$$\begin{aligned} k_c f'_c(x) - k_d f'_d(x) + \beta_T &= k_c(1 - f_c(x)) - k_d(1 - f_d(x)) + \beta_T \\ &= k_d f_d(x) - k_c f_c(x) + k_c - k_d + \beta_T \\ &= k_d \frac{1}{2}\left(1 + \mathrm{erf}\left(\frac{x-\mu_d}{\sqrt{2\sigma_d^2}}\right)\right) - \end{aligned} \tag{22}$$

-continued $$k_c\frac{1}{2}\left(1+\text{erf}\left(\frac{x-\mu_c}{\sqrt{2\sigma_c^2}}\right)\right)+k_c-k_d+\beta_T$$

In consideration that the function of Formula (22) is the function obtained by subtracting, from the function obtained by multiplying the third inverse cumulative distribution function by the weight $k_c$, the function obtained by multiplying the fourth inverse cumulative distribution function by the weight $k_d$, and adding the level value $\beta_T$, both the weight $k_c$ and the weight $k_d$ are positive values. However, in a case where the target heart is in a peculiar state, a possibility cannot be denied that at least one of the weight $k_c$ or the weight $k_d$ obtained by fitting is not a positive value. Thus, the signal analysis device 1 may perform fitting such that both the weight $k_c$ and the weight $k_d$ have positive values, but it is not essential to perform the fitting such that both the weight $k_c$ and the weight $k_d$ have positive values.

Figure 6:
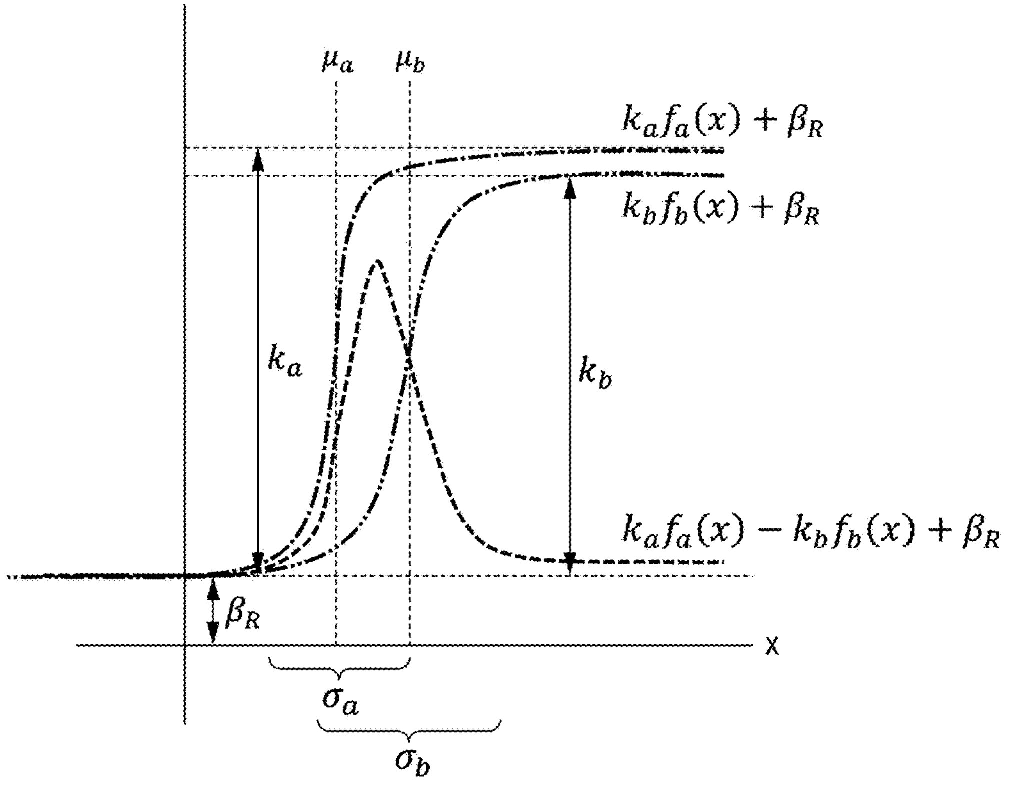
FIG. 6 is a diagram schematically illustrating a function obtained by multiplying the first cumulative distribution function by the weight and adding a level value, a function obtained by multiplying the second cumulative distribution function by the weight and adding the level value, and an approximate time waveform obtained by addition of the level value and the weighted difference between the first cumulative distribution function and the second cumulative distribution function, for the first target time waveform.

FIG. 6 is a diagram schematically illustrating a function $k_af_a(x)+\beta_R$ obtained by multiplying the first cumulative distribution function $f_a(x)$ by the weight $k_a$ and adding the level value $\beta_R$, a function $k_bf_b(x)+\beta_R$ obtained by multiplying the second cumulative distribution function $f_b(x)$ by the weight $k_b$ and adding the level value $\beta_R$, and an approximate time waveform $k_af_a(x)-k_bf_b(x)+\beta_R$ obtained by addition of the level value $\beta_R$ and the weighted difference between the first cumulative distribution function and the second cumulative distribution function, for the first target time waveform (that is, the R wave). A one-dot chain line is the function $k_af_a(x)+\beta_R$ obtained by multiplying the first cumulative distribution function $f_a(x)$ by the weight $k_a$ and adding the level value $\beta_R$, a two-dot chain line is the function $k_bf_b(x)+\beta_R$ obtained by multiplying the second cumulative distribution function $f_b(x)$ by the weight $k_c$ and adding the level value $\beta_R$, and a broken line is the approximate time waveform $k_af_a(x)-k_bf_b(x)+\beta_R$. The approximate time waveform $k_af_a(x)-k_bf_b(x)+\beta_R$ is a waveform approximating the first target time waveform (that is, the R wave).

Figure 7:
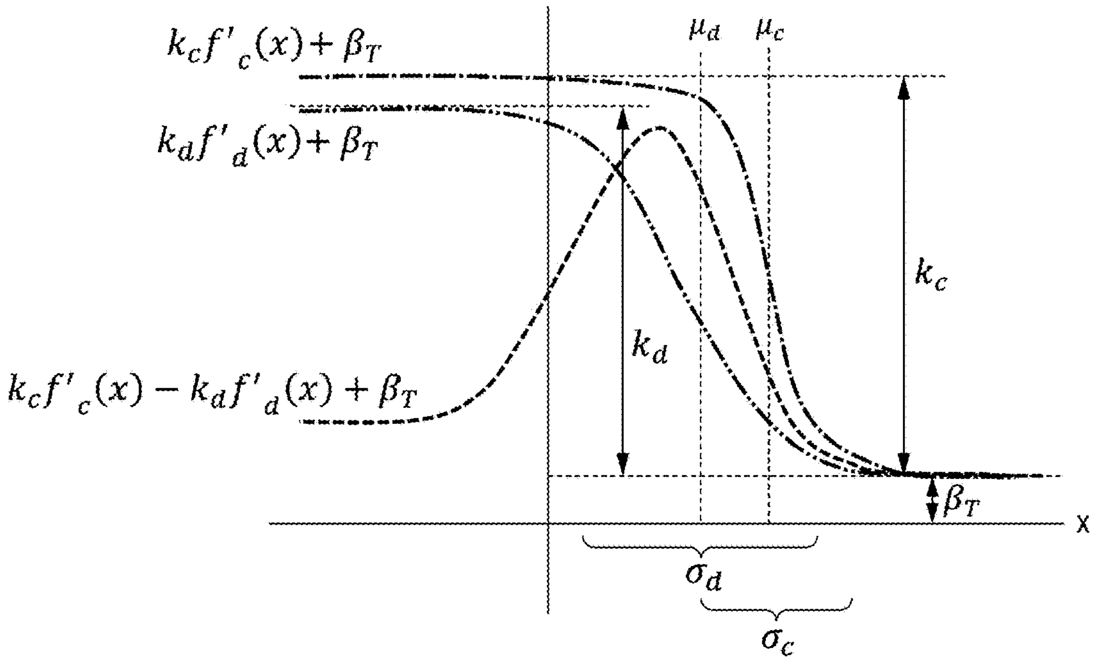
FIG. 7 is a diagram schematically illustrating a function obtained by multiplying the third inverse cumulative distribution function by the weight and adding a level value, a function obtained by multiplying the fourth inverse cumulative distribution function by the weight and adding the level value, and an approximate time waveform obtained by addition of the level value and the weighted difference between the third inverse cumulative distribution function and the fourth inverse cumulative distribution function, for the second target time waveform.

FIG. 7 is a diagram schematically illustrating a function $k_cf'_c(x)+\beta_T$ obtained by multiplying the third inverse cumulative distribution function $f'_c(x)=1-f_c(x)$ by the weight $k_c$ and adding the level value $\beta_T$, a function $k_df'_d(x)+\beta_T$ obtained by multiplying the fourth inverse cumulative distribution function $f'_d(x)=1-f_d(x)$ by the weight $k_d$ and adding the level value $\beta_T$, and an approximate time waveform $k_cf'_c(x)-k_df'_d(x)+\beta_T$ obtained by addition of the level value $\beta_T$ and the weighted difference between the third inverse cumulative distribution function and the fourth inverse cumulative distribution function, for the second target time waveform (that is, the T wave). A one-dot chain line is the function $k_cf'_c(x)+\beta_T$ obtained by multiplying the third inverse cumulative distribution function $f'_c(x)=1-f_c(x)$ by the weight $k_c$ and adding the level value $\beta_T$, a two-dot chain line is the function $k_df'_d(x)+\beta_T$ obtained by multiplying the fourth inverse cumulative distribution function $f'_d(x)=1-f_d(x)$ by the weight $k_d$ and adding the level value $\beta_T$, and a broken line is the approximate time waveform $k_cf'_c(x)-k_df'_d(x)+\beta_T$. The approximate time waveform $k_cf'_c(x)-k_df'_d(x)+\beta_T$ is a waveform approximating the second target time waveform (that is, the T wave).

Note that the level value $\beta_R$ that is the potential at the start edge of the R wave (to be exact, QRS wave) is a value representing the magnitude of a DC component at the start edge of the R wave, and in a case where there is an abnormality in a coronary artery, the level value $\beta_R$ may fall to the negative side. Furthermore, the level value $\beta_T$ that is the potential at the end edge of the T wave is a value representing the magnitude of a DC component at the end edge of the T wave, and in a case where there is an abnormality in repolarization of the myocardium, the level value $\beta_T$ may rise to the positive side.

[Approximation of Difference Between Target Time Waveform and Approximate Time Waveform]

Figure 8:
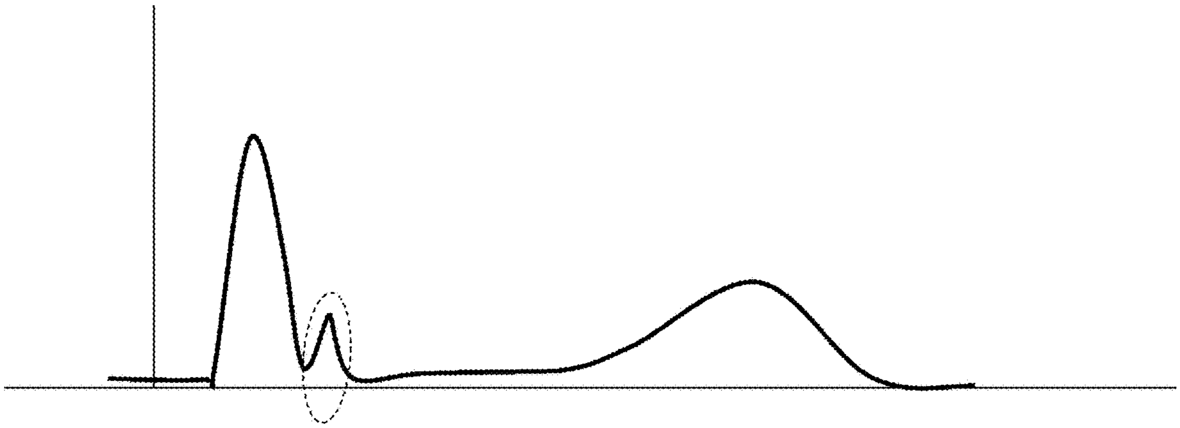
FIG. 8 is a diagram schematically illustrating a Δ wave included in a target time waveform.

In a case where the R wave or the T wave in a particular state is used as the target time waveform, a portion (hereinafter, referred to as a "residual portion") may be left in which the target time waveform cannot be approximated by the above-described approximate time waveform. For example, in a case where early repolarization or conduction disturbance (such as accessory pathway) occurs in the target heart, a Δ wave as indicated using a broken line in FIG. 8 may be included in the target time waveform (R wave). This Δ wave portion is left as the residual portion as the target time waveform cannot be approximated by the above-described approximate time waveform. In consideration that the residual portion is also a time waveform caused by certain activity of the heart, the signal analysis device 1 preferably performs analysis assuming that the residual portion is a cumulative Gaussian distribution, a function obtained by multiplying a cumulative Gaussian distribution by weight, a difference between cumulative Gaussian distributions, or a weighted difference between cumulative Gaussian distributions.

That is, as for a residual time waveform that is a difference between the target time waveform and the approximate time waveform, when the residual time waveform is approximated by a cumulative distribution function (for convenience, referred to as a "fifth cumulative distribution function") of a certain unimodal distribution (for convenience, referred to as a "fifth unimodal distribution") or a function obtained by multiplying the fifth cumulative distribution function by weight, the signal analysis device 1 may also acquire, as a parameter representing the characteristics of the target time waveform, a parameter specifying the fifth unimodal distribution or a parameter specifying the fifth cumulative distribution function.

Alternatively, as for the residual time waveform that is the difference between the target time waveform and the approximate time waveform, when the residual time waveform is approximated by a time waveform (hereinafter, referred to as an "approximate residual time waveform") represented by a difference or a weighted difference between the cumulative distribution function (for convenience, referred to as the "fifth cumulative distribution function") of the certain unimodal distribution (for convenience, referred to as the "fifth unimodal distribution") and a cumulative distribution function (for convenience, referred to as a "sixth cumulative distribution function") of a unimodal distribution (for convenience, referred to as a "sixth unimodal distribution") different from the fifth unimodal distribution, the signal analysis device 1 may also acquire, as parameters representing the characteristics of the target time waveform, the parameter specifying the fifth unimodal distribution or the parameter specifying the fifth cumulative distribution function, and a parameter specifying the sixth unimodal distribution or a parameter specifying the sixth cumulative distribution function.

More specifically, in a case where the residual time waveform is approximated by the fifth cumulative distribution function that is a cumulative distribution function of the fifth unimodal distribution expressed by Formula (23), as for the residual time waveform that is the difference between the target time waveform and the approximate time waveform, the signal analysis device 1 approximates the residual time waveform by an approximate time waveform $f_5(x)$ of the fifth cumulative distribution function expressed by Formula (24), and acquires, as parameters representing the characteristics of the target time waveform, an average $\mu_5$ and a standard deviation $\sigma_5$ that are parameters specifying the fifth cumulative distribution function, in addition to the above-described parameters representing the characteristics of the target time waveform.

[Math. 23]

$$\frac{1}{\sqrt{2\pi\sigma_5^2}}\exp\left(-\frac{(x-\mu_5)^2}{2\sigma_5^2}\right) \tag{23}$$

[Math. 24]

$$f_5(x) = \frac{1}{2}\left(1+\mathrm{erf}\left(\frac{x-\mu_5}{\sqrt{2\sigma_5^2}}\right)\right) \tag{24}$$

In a case where the residual time waveform is approximated by the function obtained by multiplying the fifth cumulative distribution function by the weight, as for the residual time waveform that is the difference between the target time waveform and the approximate time waveform, the signal analysis device 1 may approximate the residual time waveform by an approximate time waveform $k_5f_5(x)$ of a function obtained by multiplying the fifth cumulative distribution function $f_5(x)$ expressed by Formula (24) by weight $k_5$, and acquire, as parameters representing the characteristics of the target time waveform, the average 15 and the standard deviation $\sigma_5$ that are the parameters specifying the fifth cumulative distribution function, in addition to the above-described parameters representing the characteristics of the target time waveform. The signal analysis device 1 may further acquire the weight $k_5$ as a parameter representing the characteristics of the target time waveform.

In a case where the residual time waveform is approximated by the difference between the fifth cumulative distribution function and the sixth cumulative distribution function that is a cumulative distribution function of the sixth unimodal distribution expressed by Formula (25), as for the residual time waveform that is the difference between the target time waveform and the approximate time waveform, for example, the signal analysis device 1 approximates the residual time waveform by an approximate time waveform $f_5(x)-f_6(x)$ that is a waveform obtained by subtracting the sixth cumulative distribution function expressed by Formula (26) from the fifth cumulative distribution function expressed by Formula (24), and also acquires, as parameters representing the characteristics of the target time waveform, the average $\mu_5$ and the standard deviation $\sigma_5$ that are the parameters specifying the fifth cumulative distribution function and an average $\mu_6$ and a standard deviation $\sigma_6$ that are parameters specifying the sixth cumulative distribution function, in addition to the above-described parameters representing the characteristics of the target time waveform.

[Math. 25]

$$\frac{1}{\sqrt{2\pi\sigma_6^2}}\exp\left(-\frac{(x-\mu_6)^2}{2\sigma_6^2}\right) \tag{25}$$

[Math. 26]

$$f_6(x) = \frac{1}{2}\left(1+\mathrm{erf}\left(\frac{x-\mu_6}{\sqrt{2\sigma_6^2}}\right)\right) \tag{26}$$

In a case where the residual time waveform is approximated by the weighted difference between the fifth cumulative distribution function and the sixth cumulative distribution function, as for the residual time waveform that is the difference between the target time waveform and the approximate time waveform, the signal analysis device 1 approximates the residual time waveform by an approximate time waveform $k_5f_5(x)-k_6f_6(x)$ that is a waveform obtained by subtracting a function $k_6f_6(x)$ obtained by multiplying the sixth cumulative distribution function $f_6(x)$ by weight $k_6$ from a function $k_5f_5(x)$ obtained by multiplying the fifth cumulative distribution function $f_5(x)$ by the weight $k_5$, and also acquires, as parameters representing the characteristics of the target time waveform, the average $\mu_5$ and the standard deviation $\sigma_5$ that are the parameters specifying the fifth cumulative distribution function and the average $\mu_6$ and the standard deviation of that are the parameters specifying the sixth cumulative distribution function, in addition to the above-described parameters representing the characteristics of the target time waveform. The signal analysis device 1 may further acquire the weight $k_5$ and the weight $k_c$ or a ratio of the weight $k_5$ and the weight $k_6$ ($k_5/k_6$ or $k_6/k_5$) as parameters representing the characteristics of the target time waveform.

In consideration that the residual time waveform is approximated by the approximate time waveform obtained by multiplying the sixth cumulative distribution function by the weight $k_c$ from the function obtained by multiplying the fifth cumulative distribution function by the weight $k_5$, both the weight $k_5$ and the weight $k_c$ are positive values. However, in a case where the target heart is in a peculiar state, a possibility cannot be denied that at least one of the weight $k_5$ or the weight $k_6$ obtained by fitting is not a positive value. Thus, the signal analysis device 1 may perform fitting such that both the weight $k_5$ and the weight $k_6$ have positive values, but it is not essential to perform the fitting such that both the weight $k_5$ and the weight $k_6$ have positive values.

The description returns to FIG. 1. The signal analysis device 1 includes a control unit 11 including a processor 91 such as a central processing unit (CPU) and a memory 92 connected together by a bus, and executes a program. The signal analysis device 1 functions as a device including the control unit 11, an input unit 12, a communication unit 13, a storage unit 14, and an output unit 15 by executing the program.

More specifically, the processor 91 reads the program stored in the storage unit 14, and stores the read program in the memory 92. The processor 91 executes the program stored in the memory 92, whereby the signal analysis device 1 functions as the device including the control unit 11, the input unit 12, the communication unit 13, the storage unit 14, and the output unit 15.

The control unit 11 controls operation of various functional units included in the signal analysis device 1. The control unit 11 executes, for example, the myocardial activity information parameter acquisition processing. The control unit 11 controls operation of the output unit 15, for example, and causes the output unit 15 to output an acquisition result of the myocardial activity information parameter acquisition processing. The control unit 11 records, in the storage unit 14, various types of information generated by execution of the myocardial activity information parameter acquisition processing, for example.

The input unit 12 includes an input device such as a mouse, a keyboard, or a touchscreen. The input unit 12 may be configured as an interface that connects these input devices to the signal analysis device 1. The input unit 12 receives input of various types of information to the signal analysis device 1.

For example, information indicating a shape of a distribution represented by each cumulative distribution function (hereinafter, the information is referred to as "distribution shape designation information") is input to the input unit 12 for a plurality of candidates for each cumulative distribution function used for fitting.

Note that the distribution shape designation information may be stored in the storage unit 14 in advance. In such a case, the distribution shape designation information stored in the storage unit 14 does not need to be input from the input unit 12. Hereinafter, the signal analysis device 1 will be described by taking, as an example, a case where the storage unit 14 stores the distribution shape designation information in advance for simplicity of description.

The communication unit 13 includes a communication interface for connecting the signal analysis device 1 to an external device. The communication unit 13 communicates with the external device in a wired or wireless manner. The external device is, for example, a device of a transmission source of a waveform of an electrocardiogram of a target heart. The device of the transmission source of the waveform of the electrocardiogram of the target heart is, for example, an electrocardiogram measurement device. For example, in a case where the external device is the electrocardiogram measurement device, the communication unit 13 acquires the waveform of the electrocardiogram from the electrocardiogram measurement device by communication. Note that the waveform of the electrocardiogram may be input to the input unit 12.

The storage unit 14 includes a non-transitory computer-readable storage medium device such as a magnetic hard disk device or a semiconductor storage device. The storage unit 14 stores various types of information regarding the signal analysis device 1. The storage unit 14 stores, for example, information input via the input unit 12 or the communication unit 13. The storage unit 14 stores, for example, an electrocardiogram input via the input unit 12 or the communication unit 13. The storage unit 14 stores, for example, various types of information generated by execution of the myocardial activity information parameter acquisition processing.

The output unit 15 outputs various types of information. The output unit 15 includes, for example, a display device such as a cathode ray tube (CRT) display, a liquid crystal display, or an organic electro-luminescence (EL) display. The output unit 15 may be configured as an interface that connects these display devices to the signal analysis device 1. The output unit 15 outputs, for example, information input to the input unit 12. The output unit 15 may display, for example, an electrocardiogram input to the input unit 12 or the communication unit 13. The output unit 15 may display, for example, an execution result of the myocardial activity information parameter acquisition processing.

Figure 9:
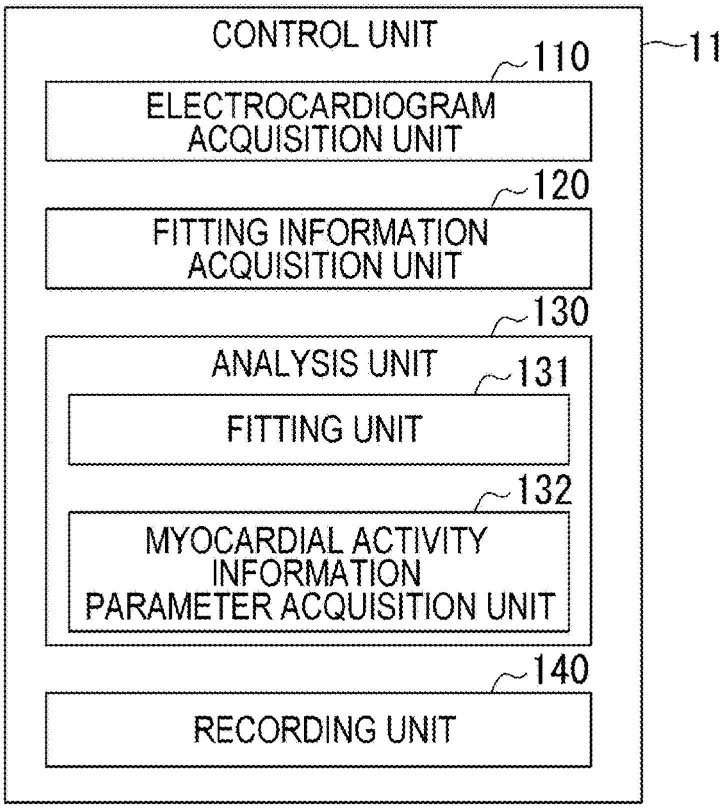
FIG. 9 is a diagram illustrating an example of a functional configuration of a control unit 11 in the first embodiment.

FIG. 9 is a diagram illustrating an example of a functional configuration of the control unit 11 in the first embodiment. The control unit 11 includes an electrocardiogram acquisition unit 110, a fitting information acquisition unit 120, an analysis unit 130, and a recording unit 140.

The electrocardiogram acquisition unit 110 acquires a waveform for one cycle from the waveform of the electrocardiogram of the target heart input to the input unit 12 or the communication unit 13, and outputs the waveform to the analysis unit 130. The waveform of the electrocardiogram of the target heart is a waveform in which waveforms of a plurality of beats (a plurality of cycles) is arranged in time series. Even in a case where an abnormality occurs in the target heart, not all waveforms of beats included in the waveform of the electrocardiogram are particular waveforms, and only waveforms of any small number of beats included in the waveform of the electrocardiogram are often characteristic waveforms. In the myocardial activity information parameter acquisition processing, this characteristic waveform is preferably targeted. Thus, the electrocardiogram acquisition unit 110 acquires a waveform for one cycle that is a characteristic waveform from the waveform of the electrocardiogram of the target heart. For example, the electrocardiogram acquisition unit 110 only needs to acquire the waveform for one cycle that is the characteristic waveform from the waveform of the electrocardiogram of the target heart by using a known technique for determining similarity and peculiarity. Furthermore, for example, the electrocardiogram acquisition unit 110 may cause the output unit 15 to display the waveform of the electrocardiogram, cause the input unit 12 to receive designation of a waveform for one cycle by a user such as a doctor, and acquire a waveform for one cycle corresponding to the designation received by the input unit 12 from the waveform of the electrocardiogram.

The electrocardiogram acquisition unit 110 outputs the waveform for one cycle as digital time-series data sampled at a predetermined sampling frequency. The predetermined sampling frequency is a sampling frequency of a signal used in processing in the fitting information acquisition unit 120, and is, for example, 250 Hz. In a case where the input waveform of the electrocardiogram is sampled at the predetermined sampling frequency, the electrocardiogram acquisition unit 110 only needs to cut out digital time-series data of a waveform for one cycle from digital time-series data of the input waveform of the electrocardiogram and output the digital time-series data. In a case where the input waveform of the electrocardiogram is sampled at a sampling frequency different from the predetermined sampling frequency, the electrocardiogram acquisition unit 110 only needs to cut out digital time-series data of a waveform for one cycle from digital time-series data of the input waveform of the electrocardiogram, convert the digital time-series data to the predetermined frequency, and then output the digital time-series data.

Moreover, the electrocardiogram acquisition unit 110 specifies a time section of the R wave and a time section of the T wave included in the waveform of one cycle of the electrocardiogram, acquires information specifying the time section of the R wave and information specifying the time section of the T wave, and outputs the information to the analysis unit 130. For example, the electrocardiogram acquisition unit 110 only needs to specify the start edge of the R wave, the end edge of the R wave, the start edge of the T wave, and the end edge of the T wave by a known technique, and acquire sample numbers corresponding to the specified start edge of the R wave, end edge of the R wave, start edge of the T wave, and end edge of the T wave, relative times from the start edges of the waveforms, and the like as the information specifying the time section of the R wave and the information specifying the time section of the T wave. Note that the R wave in the present specification refers to a QRS wave, to be exact. Although it is true that there are various interpretations as to which point of a waveform the start edge of the R wave (that is, start edge of the QRS wave) is, the electrocardiogram acquisition unit 110 only needs to set a point specified by any known technique as the start edge of the R wave.

Note that, in the waveform of the electrocardiogram of the target heart, a characteristic waveform may appear that changes as time passes. Thus, the electrocardiogram acquisition unit 110 may acquire, from the waveform of the electrocardiogram of the target heart, waveforms for a plurality of cycles as a target waveform on which the myocardial activity information parameter acquisition processing is performed. That is, the electrocardiogram acquisition unit 110 may acquire a time-series waveform (trend graph) in a predetermined long-term from the waveform of the electrocardiogram of the target heart, and output, for a waveform of each cycle included in the acquired waveform, the waveform, the information specifying the time section of the R wave included in the waveform, and the information specifying the time section of the T wave included in the waveform to the analysis unit 130.

The fitting information acquisition unit 120 acquires the distribution shape designation information. In a case where the distribution shape designation information is stored in the storage unit 14, the fitting information acquisition unit 120 reads the distribution shape designation information from the storage unit 14.

The analysis unit 130 includes a fitting unit 131 and a myocardial activity information parameter acquisition unit 132.

Using candidates for cumulative distribution functions indicated by the distribution shape designation information, the fitting unit 131 performs fitting on the target time waveform that is the waveform in the time section of at least one of the R wave or the T wave included in the waveform for one cycle of the electrocardiogram acquired by the electrocardiogram acquisition unit 110.

The myocardial activity information parameter acquisition unit 132 acquires parameters representing characteristics of the target time waveform on the basis of results of fitting by the fitting unit 131. The myocardial activity information parameter acquisition unit 132 acquires, as parameters representing the characteristics of the target time waveform, for example, the parameter specifying the first unimodal distribution or the parameter specifying the first cumulative distribution function, and the parameter specifying the second unimodal distribution or the parameter specifying the second cumulative distribution function when the target time waveform is approximated by the approximate time waveform that is the time waveform represented by the difference or the weighted difference between the first cumulative distribution function that is a cumulative distribution function of the first unimodal distribution and the second cumulative distribution function that is a cumulative distribution function of the second unimodal distribution. The parameters representing the characteristics of the target time waveform acquired by the myocardial activity information parameter acquisition unit 132 are examples of myocardial activity parameters.

As described above, the analysis unit 130 acquires the myocardial activity parameters on the basis of the target time waveform that is the waveform in the time section of at least one of the R wave or the T wave included in the waveform for one cycle of the electrocardiogram of the target heart and distribution candidate information.

The storage unit 14 records various types of information generated by processing executed by the control unit 11 in the storage unit 14.

Figure 10:
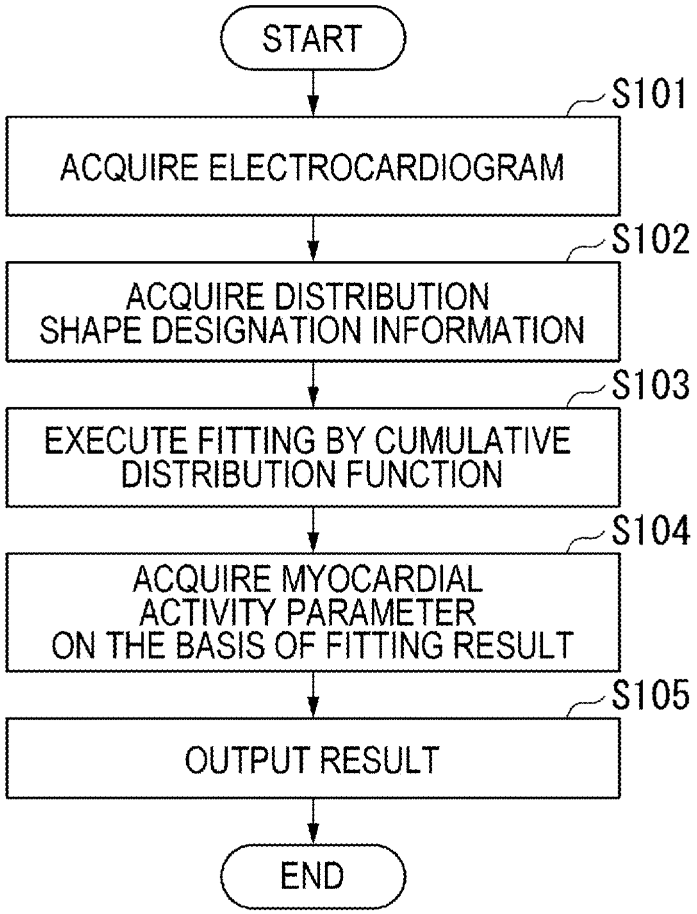
FIG. 10 is a flowchart illustrating an example of a flow of processing executed by the signal analysis device 1 in the first embodiment.

FIG. 10 is a flowchart illustrating an example of a flow of processing executed by the signal analysis device 1 in the first embodiment. The electrocardiogram acquisition unit 110 acquires the waveform for one cycle of the electrocardiogram of the target heart, the information specifying the time section of the R wave, and the information specifying the time section of the T wave via the input unit 12 or the communication unit 13 (step S101). Next, the fitting information acquisition unit 120 acquires the distribution shape designation information (step S102). Next, using the candidates for the cumulative distribution functions indicated by the distribution shape designation information, the fitting unit 131 performs fitting on the target time waveform that is the waveform in the time section of at least one of the R wave or the T wave included in the waveform for one cycle of the electrocardiogram acquired in step S101 (step S103). Next, the myocardial activity information parameter acquisition unit 132 acquires the myocardial activity parameters on the basis of the fitting results (step S104). The acquired myocardial activity parameters are output to the output unit 15 (step S105).

In step S105, a graph of the fitting results for each target time waveform may be displayed. Furthermore, the processing in step S102 only needs to be executed before the processing in step S103 is executed, and may be executed before execution of step S101. The processing in steps S103 and S104 is an example of processing executed by the analysis unit 130.

Figure 11:
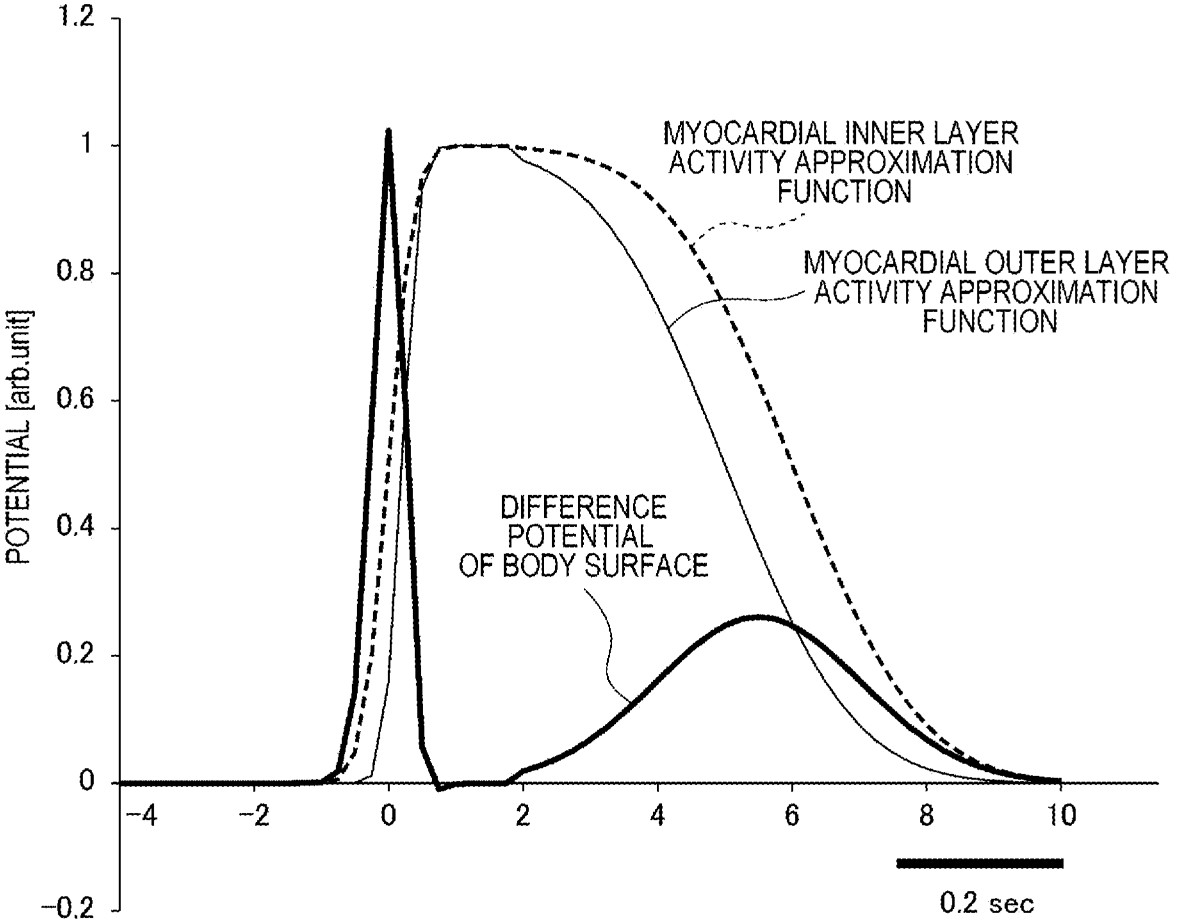
FIG. 11 is a first diagram illustrating an example of analysis results by the signal analysis device 1 in the first embodiment.

FIG. 11 is a first diagram illustrating an example of analysis results by the signal analysis device 1 in the first embodiment. More specifically, FIG. 11 is an example of analysis results by the signal analysis device 1 for the waveform of the electrocardiogram of the target heart in which the motion is normal. In FIG. 11, the horizontal axis represents time and the vertical axis represents a potential. A unit of the vertical axis is an arbitrary unit.

FIG. 11 illustrates an example in which results of performing first fitting and second fitting on the R wave in depolarization of the electrocardiogram of the target heart in which the motion is normal, and results of performing fourth fitting and third fitting on the T wave in a repolarization phase of the electrocardiogram of the target heart in which the motion is normal, are displayed using $k_a/\alpha_1$ instead of the weight $k_a$ so that the first fitting result at the time T3 and the third fitting result at the time T4 are the same value, and using $k_b/\alpha_2$ instead of the weight $k_b$ so that the second fitting result at the time T3 and the fourth fitting result at the time T4 are the same value. Hereinafter, a result obtained by connecting the first fitting result having changed weight and the third fitting result together via a straight line is referred to as a myocardial inner layer activity approximation function, and a result obtained by connecting the second fitting result having changed weight and the fourth fitting result together via a straight line is referred to as a myocardial outer layer activity approximation function.

FIG. 11 corresponds to a fact that, in depolarization in a normal heart, activity (that is, activity of ion channels) of the myocardial inner layer starts earlier and proceeds rapidly than that of the myocardial outer layer, activity of the myocardial outer layer starts slightly later than a timing at which activity of ion channels of the myocardial inner layer starts, and a difference between the timing at which the activity of ion channels of the myocardial inner layer starts and a timing at which the activity of the myocardial outer layer starts results in a positive and sharp R wave. That is, an average value and a standard deviation of the myocardial inner layer activity approximation function of a portion of the first fitting result, in the myocardial inner layer activity approximation function, and an average value and a standard deviation of a portion of the second fitting result, in the myocardial outer layer activity approximation function, are parameters representing timing and progress of activity of ion channels in depolarization of the normal heart.

Furthermore, FIG. 11 corresponds to a fact that, in a repolarization phase of the normal heart, inactivation of activity of ion channels in the myocardial outer layer starts earlier than that in the myocardial inner layer, inactivation of the myocardial inner layer starts later than inactivation of the myocardial outer layer, both the inactivation of the myocardial outer layer and the inactivation of the myocardial inner layer proceed slowly, and a difference between the inactivation of the myocardial inner layer and the inactivation of the myocardial outer layer results in a positive and gentle T wave. That is, an average value and a standard deviation of a portion of the fourth fitting result, in the myocardial outer layer activity approximation function, and an average value and a standard deviation of a portion of the third fitting result, in the myocardial inner layer activity approximation function, are parameters representing timing and progress of inactivation of activity of ion channels in the repolarization phase of the normal heart. As described above, the myocardial inner layer activity approximation function and the myocardial outer layer activity approximation function obtained by the first to fourth fitting correspond to timing and progress of collective activation of ion channels in the depolarization and collective inactivation of ion channels in the repolarization phase, and average values and standard deviations of the fitting results of the functions are parameters representing activity of the myocardium.

Shapes of the myocardial inner layer activity approximation function and the myocardial outer layer activity approximation function in FIG. 11 substantially correspond to results of measurement of electromotive force of the myocardium directly measured by inserting a catheter electrode into the myocardium of the target heart in which the motion is normal. This indicates that, with the signal analysis device 1, information representing the activity of the myocardium can be acquired only from the electrocardiogram without inserting the catheter electrode.

Figure 12:
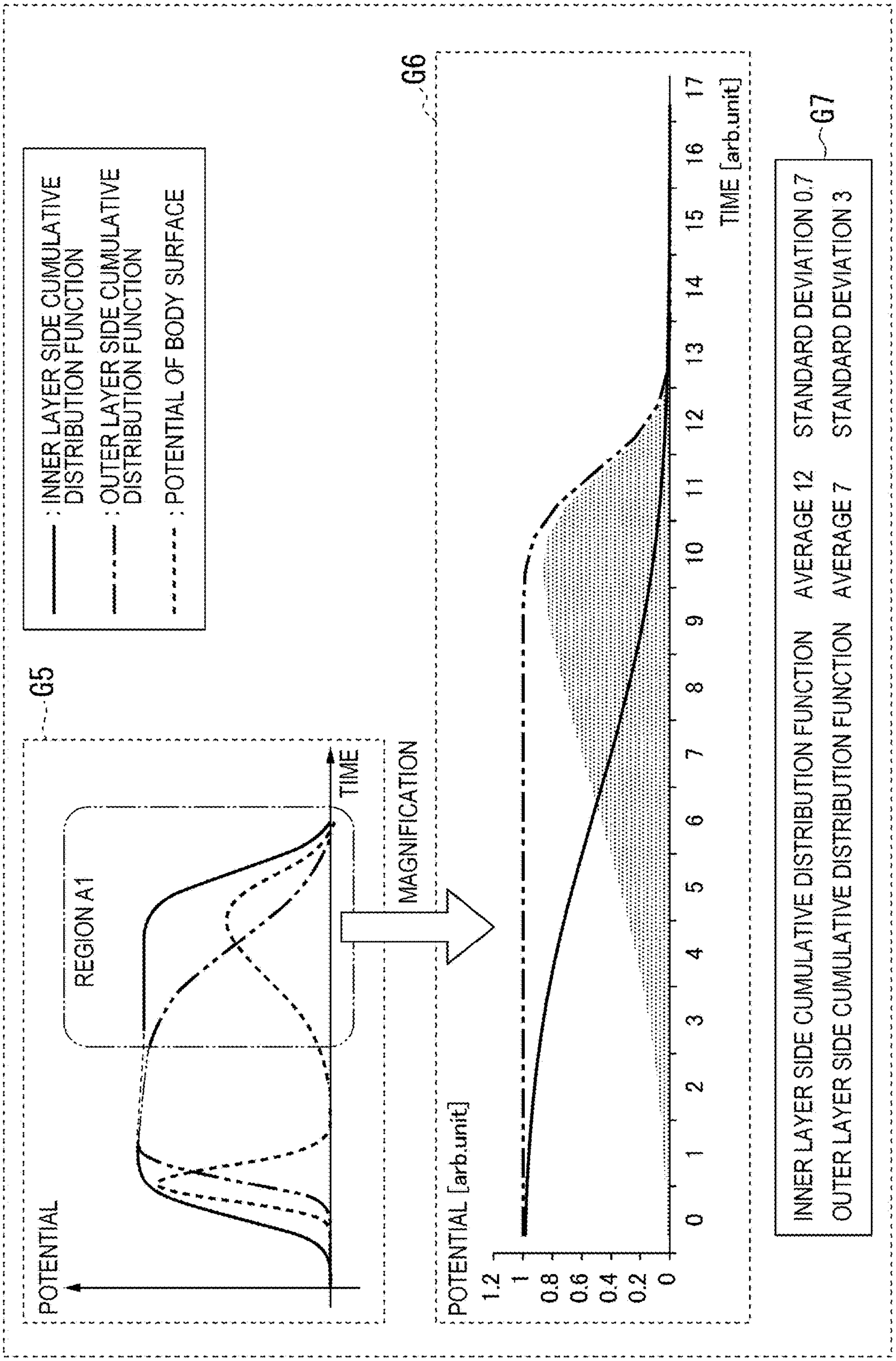
FIG. 12 is a second diagram illustrating an example of analysis results by the signal analysis device 1 in the first embodiment.

FIG. 12 is a second diagram illustrating an example of analysis results by the signal analysis device 1 in the first embodiment. More specifically, FIG. 12 is an example of analysis results by the signal analysis device 1 for the waveform of the electrocardiogram of the target heart in which the motion is normal.

Figure 13:
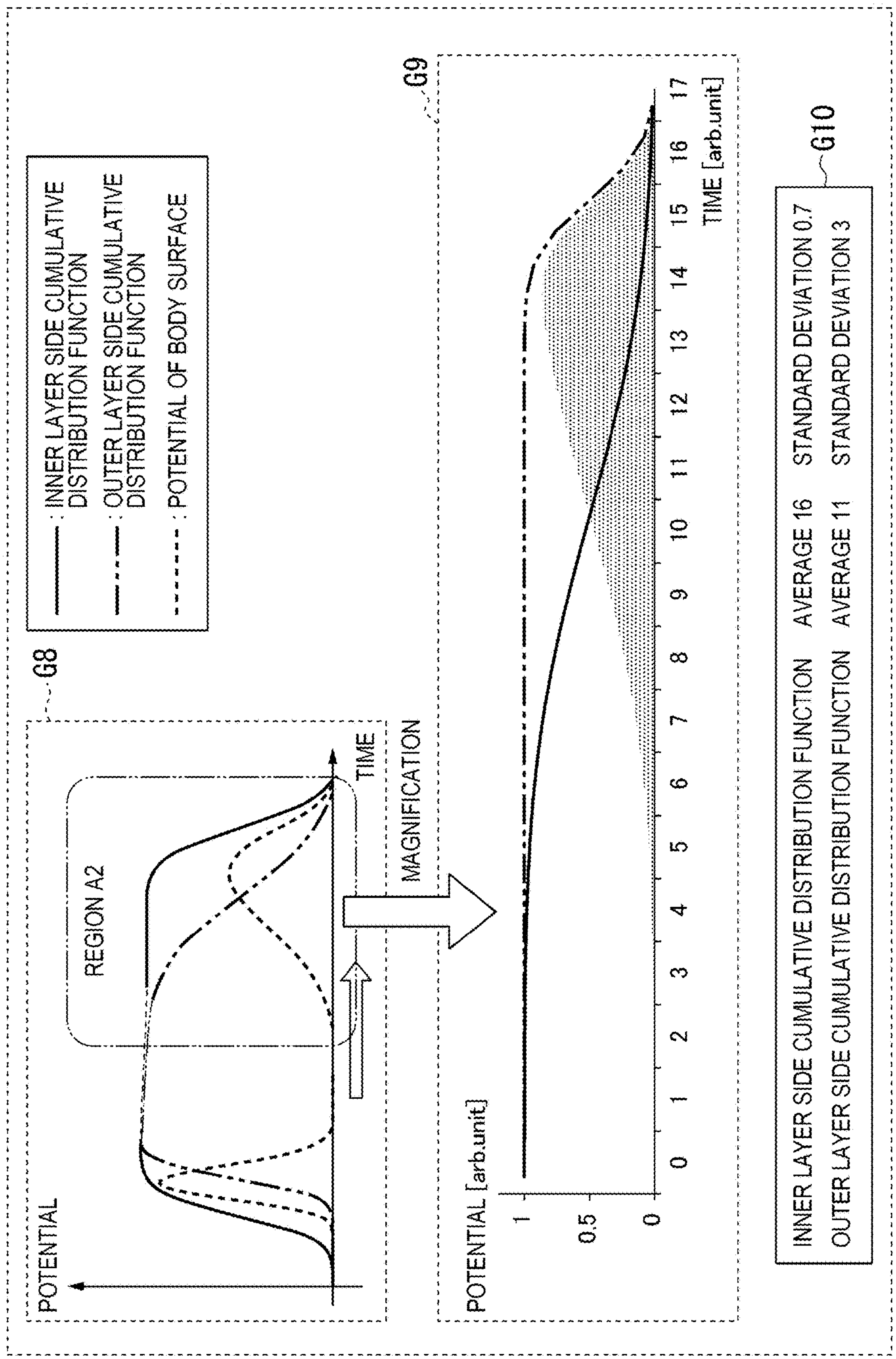
FIG. 13 is a third diagram illustrating an example of analysis results by the signal analysis device 1 in the first embodiment.
Figure 14:
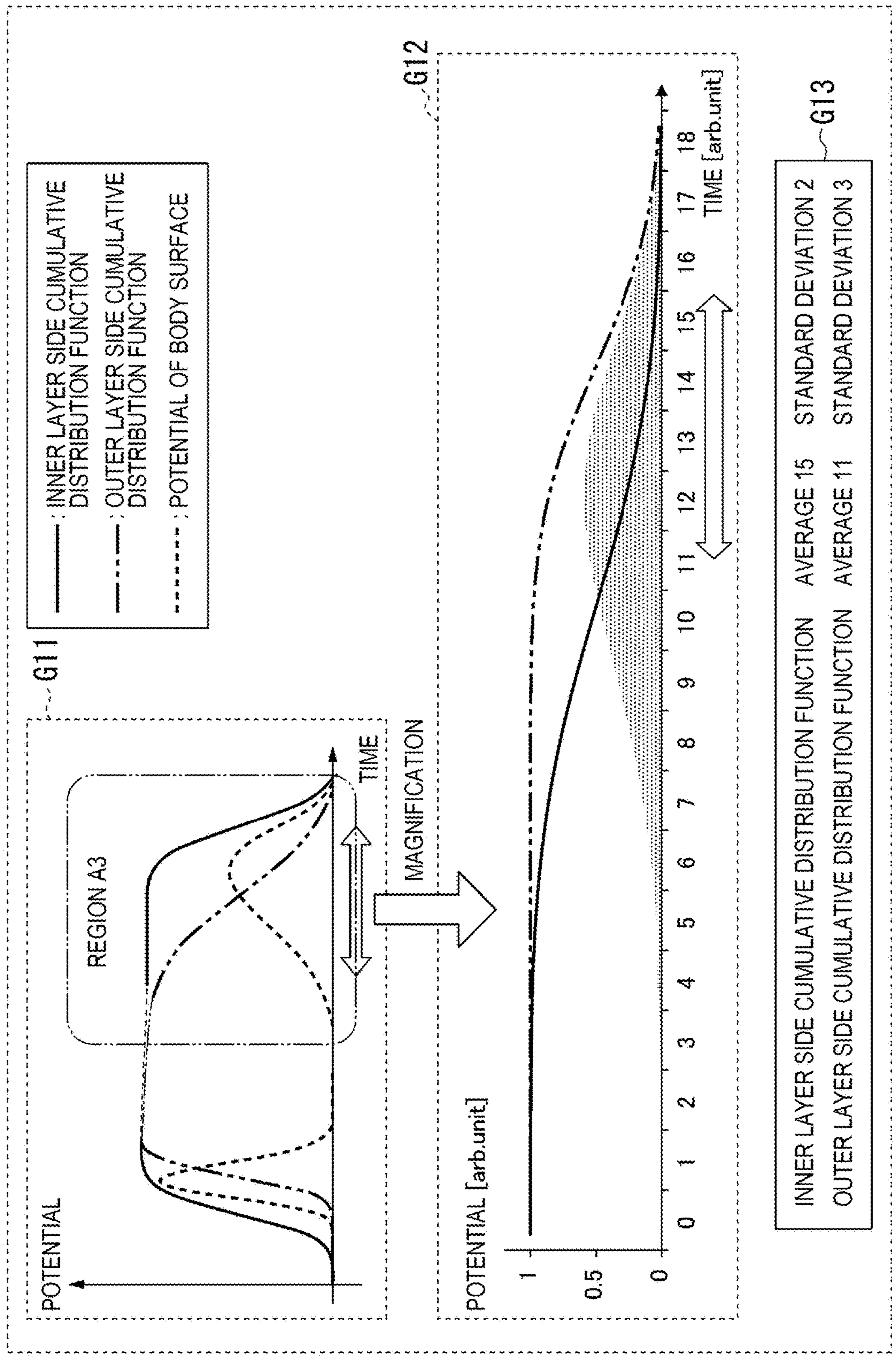
FIG. 14 is a fourth diagram illustrating an example of analysis results by the signal analysis device 1 in the first embodiment.

FIG. 12 illustrates three results of a graph G5, a graph G6, and a result G7. In FIG. 12, “inner layer side cumulative distribution function” indicates a fitting result of a function representing a collective channel activity timing distribution of ion channels existing in the myocardial inner layer. In FIG. 12, “outer layer side cumulative distribution function” indicates a fitting result of a function representing a collective channel activity timing distribution of ion channels existing in the myocardial outer layer. In FIG. 12, “potential of body surface” is a function representing a temporal change in potential of the body surface and is the waveform of the electrocardiogram. In FIG. 12, the horizontal axis represents time and the vertical axis represents a potential. Units of both the horizontal axis and the vertical axis are all arbitrary units. Note that the length of time represented by an interval of one scale on each of horizontal axes in FIGS. 12 to 14 is the same length. Furthermore, in each of vertical axes in FIGS. 12 to 14, 1 represents the maximum value of a cumulative Gaussian distribution.

The graph G5 represents an entire waveform of the electrocardiogram generated in one-time pulsation. The graph G6 illustrates an enlarged view of a T wave region that is a part of the graph G5. The T wave region is a region indicated as a region A1 in FIG. 12. The result G7 indicates statistics of two Gaussian distributions of a Gaussian distribution that is a cumulative source of the inner layer side cumulative distribution function and a Gaussian distribution that is a cumulative source of the outer layer side cumulative distribution function. Values of the result G7 represent the statistics of the two Gaussian distributions. Specifically, the statistics of the two Gaussian distributions are average values and standard deviations of Gaussian distributions that are cumulative sources of the inner layer side cumulative distribution function and the outer layer side cumulative distribution function.

FIG. 13 is a third diagram illustrating an example of analysis results by the signal analysis device 1 in the first embodiment. More specifically, FIG. 13 is an example of analysis results by the signal analysis device 1 for the waveform of the electrocardiogram of the target heart in which the motion is long T type 3.

FIG. 13 illustrates three results of a graph G8, a graph G9, and a result G10. In FIG. 13, “inner layer side cumulative distribution function” indicates a fitting result of a function representing a collective channel activity timing distribution of channels existing in the myocardial inner layer. In FIG. 13, “outer layer side cumulative distribution function” indicates a fitting result of a function representing a collective channel activity timing distribution of channels existing in the myocardial outer layer. In FIG. 13, “potential of body surface” is a function representing a temporal change in potential of the body surface and is the waveform of the electrocardiogram. In FIG. 13, the horizontal axis represents time and the vertical axis represents a potential. Units of both the horizontal axis and the vertical axis are all arbitrary units.

The graph G8 represents an entire waveform of the electrocardiogram generated in one-time pulsation. The graph G9 illustrates an enlarged view of a T wave region that is a part of the graph G8. The T wave region is a region indicated as a region A2 in FIG. 13. The result G10 indicates statistics of two Gaussian distributions of a Gaussian distribution that is a cumulative source of the inner layer side cumulative distribution function and a Gaussian distribution that is a cumulative source of the outer layer side cumulative distribution function. Values of the result G10 represent the statistics of the two Gaussian distributions, that is, average values and standard deviations of Gaussian distributions that are cumulative sources of the inner layer side cumulative distribution function and the outer layer side cumulative distribution function.

Shapes of the inner layer side cumulative distribution function and the outer layer side cumulative distribution function in FIG. 13 substantially correspond to results obtained by directly measuring a change in electromotive force generated by pulsation of the myocardial outer layer of the target heart in which the motion is long T type 3 by inserting a catheter electrode. This indicates that, with the signal analysis device 1, information representing the activity of the myocardium can be acquired only from the electrocardiogram without inserting the catheter electrode.

FIG. 14 is a fourth diagram illustrating an example of analysis results by the signal analysis device 1 in the first embodiment. More specifically, FIG. 14 is an example of analysis results by the signal analysis device 1 for the waveform of the electrocardiogram of the target heart in which the motion is long QT type 1.

FIG. 14 illustrates three results of a graph G11, a graph G12, and a result G13. In FIG. 14, “inner layer side cumulative distribution function” indicates a fitting result of a function representing a collective channel activity timing distribution of channels existing in the myocardial inner layer. In FIG. 14, “outer layer side cumulative distribution function” indicates a fitting result of a function representing a collective channel activity timing distribution of channels existing in the myocardial outer layer. In FIG. 14, "potential of body surface" is a function representing a temporal change in potential of the body surface and is the waveform of the electrocardiogram. In FIG. 14, the horizontal axis represents time and the vertical axis represents a potential. Units of both the horizontal axis and the vertical axis are all arbitrary units.

The graph G11 represents an entire waveform of the electrocardiogram generated in one-time pulsation. The graph G12 illustrates an enlarged view of a T wave region that is a part of the graph G11. The T wave region is a region indicated as a region A3 in FIG. 13. The result G13 indicates statistics of two Gaussian distributions of a Gaussian distribution that is a cumulative source of the inner layer side cumulative distribution function and a Gaussian distribution that is a cumulative source of the outer layer side cumulative distribution function. Values of the result G13 represent the statistics of the two Gaussian distributions. Specifically, the statistics of the two Gaussian distributions are average values and standard deviations of Gaussian distributions that are cumulative sources of the inner layer side cumulative distribution function and the outer layer side cumulative distribution function.

Shapes of the inner layer side cumulative distribution function and the outer layer side cumulative distribution function in FIG. 14 substantially correspond to results obtained by directly measuring a change in electromotive force generated by pulsation of the myocardial outer layer of the target heart in which the motion is long QT type 3 by inserting a catheter electrode. This indicates that, with the signal analysis device 1, information representing the activity of the myocardium can be acquired only from the electrocardiogram without inserting the catheter electrode.

Note that FIG. 14 is also an example of a result of estimation of channel current characteristics related to sudden death by the signal analysis device 1.

Figure 15:
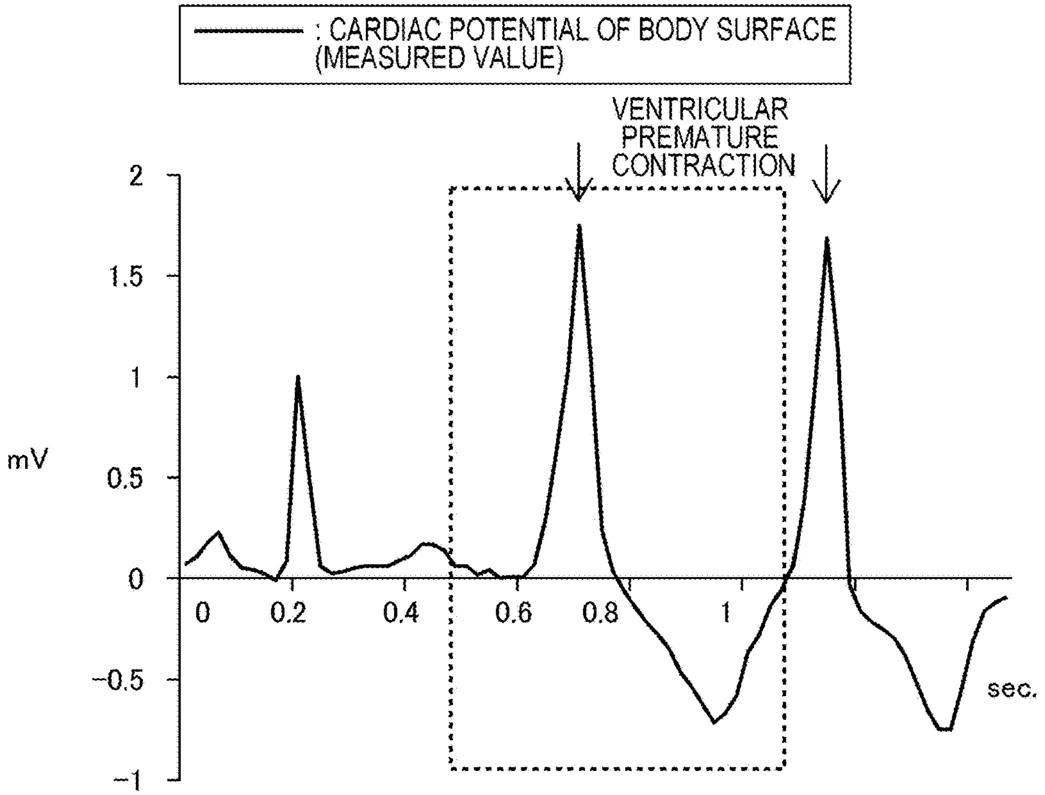
FIG. 15 is a first explanatory diagram of an example in which an electrocardiogram of ventricular premature contractions is analyzed by the signal analysis device 1 of the first embodiment.
Figure 16:
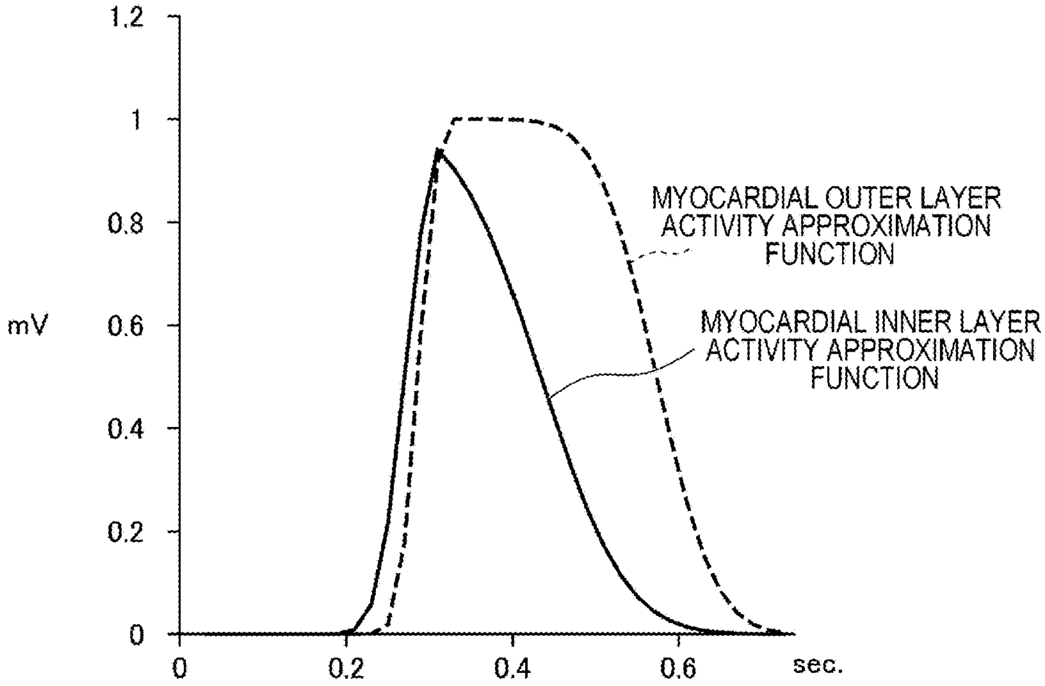
FIG. 16 is a second explanatory diagram of the example in which the electrocardiogram of the ventricular premature contractions is analyzed by the signal analysis device 1 of the first embodiment.
Figure 17:
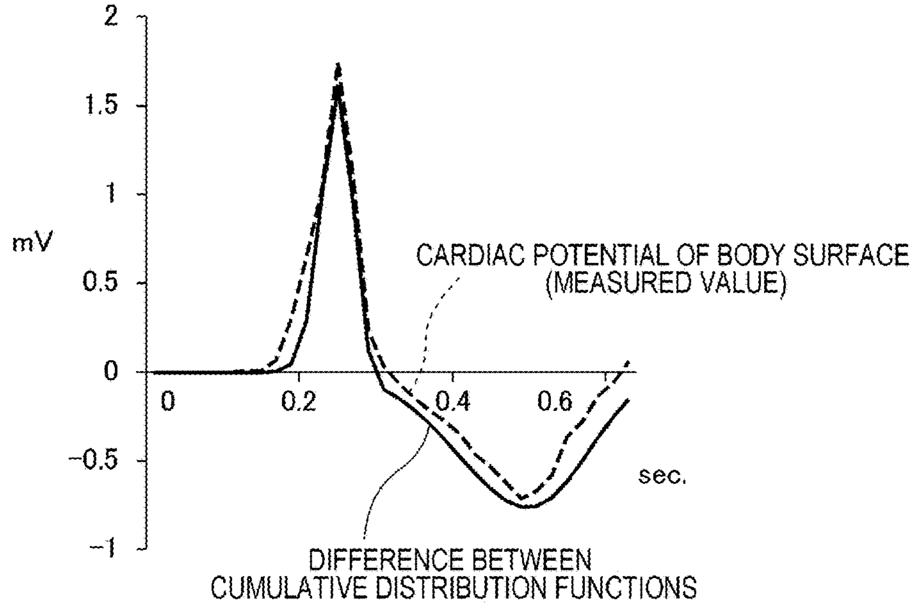
FIG. 17 is a third explanatory diagram of the example in which the electrocardiogram of the ventricular premature contractions is analyzed by the signal analysis device 1 of the first embodiment.

With reference to FIGS. 15 to 17, it will be described that information representing activity of a myocardium can be acquired only from an electrocardiogram by the signal analysis device 1 also for an electrocardiogram of ventricular premature contractions. In FIGS. 15 to 17, the horizontal axis represents time (second) and the vertical axis represents a potential (mV).

FIG. 15 is a first explanatory diagram for describing an example in which the electrocardiogram of the ventricular premature contractions is analyzed by the signal analysis device 1 of the first embodiment. FIG. 16 is a second explanatory diagram of the example in which the electrocardiogram of the ventricular premature contractions is analyzed by the signal analysis device 1 of the first embodiment. FIG. 17 is a third explanatory diagram of the example in which the electrocardiogram of the ventricular premature contractions is analyzed by the signal analysis device 1 of the first embodiment.

More specifically, FIG. 15 illustrates a cardiac potential of the body surface. That is, FIG. 15 illustrates normal one-time heartbeat and two consecutive ventricular premature contractions recorded in the electrocardiogram. More specifically, FIG. 16 illustrates a myocardial inner layer activity approximation function including an inner layer side cumulative distribution function in depolarization and an inner layer side cumulative distribution function of a repolarization phase, of a ventricular premature contraction analyzed by the signal analysis device 1, and a myocardial outer layer activity approximation function including an outer layer side cumulative distribution function in the depolarization and an outer layer side cumulative distribution function in the repolarization phase, of the ventricular premature contraction analyzed by the signal analysis device 1. More specifically, FIG. 17 illustrates an example of a waveform of a ventricular premature contraction of an actually measured electrocardiogram.

FIG. 16 illustrates that the inner layer side cumulative distribution function in the depolarization precedes the outer layer side cumulative distribution function, and a standard deviation of each of the inner layer side cumulative distribution function and the outer layer side cumulative distribution function is larger than that of a normal heartbeat, and a spread of excitation is gentle. This analysis result corresponds to characteristics of a waveform of the R wave having a wide skirt.

FIG. 16 corresponds to a fact that the inner layer side cumulative distribution function starts inactivation earlier than the outer layer side cumulative distribution function in the repolarization phase, and illustrates the order of inactivation on the inner layer side and the outer layer side as a magnitude relationship between average values of two cumulative distribution functions in the repolarization phase. A function obtained by subtracting the outer layer side cumulative distribution function from the inner layer side cumulative distribution function in FIG. 16 corresponds to characteristics of a large negative T wave in the repolarization phase, and as illustrated in FIG. 17, a waveform obtained by subtracting the outer layer side cumulative distribution function from the inner layer side cumulative distribution function substantially corresponds to a waveform of the ventricular premature contraction of the actually measured electrocardiogram.

Note that results of FIGS. 15 to 17 indicate that analysis by the signal analysis device 1 corresponds to an example in which a giant wave or a negative potential is generated due to modified conduction of excitation of the myocardium, early repolarization, or delay of repolarization. Note that, in FIGS. 15 to 17, an average u of the inner layer side cumulative distribution function in the depolarization phase is −1, and a standard deviation $\sigma$ is 0.32. Furthermore, in FIGS. 15 to 17, an average $\mu$ of the outer layer side cumulative distribution function in the depolarization is −0.8, and a standard deviation $\sigma$ is 0.21. Furthermore, in FIGS. 15 to 17, an average $\mu$ of the inner layer side cumulative distribution function in the repolarization phase is 1, and a standard deviation $\sigma$ is 1. Furthermore, in FIGS. 15 to 17, an average $\mu$ of the outer layer side cumulative distribution function in the repolarization phase is 2.99, and a standard deviation $\sigma$ is 0.7.

Figure 18:
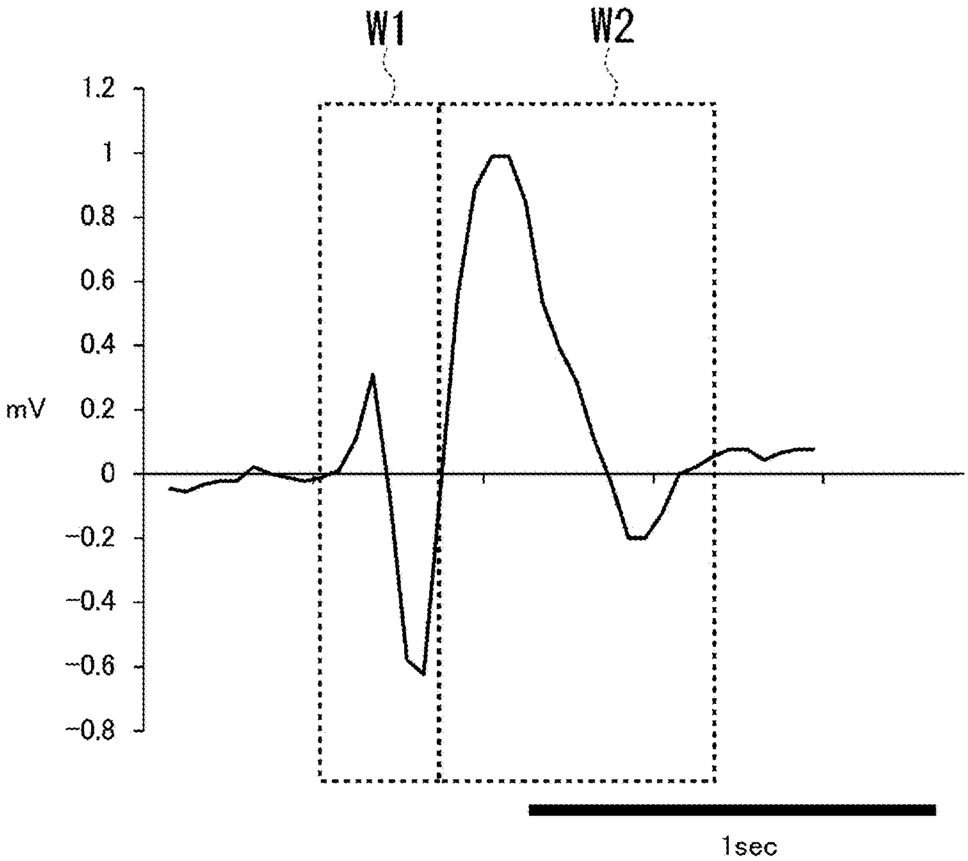
FIG. 18 is a first explanatory diagram in which an electrocardiogram of the target heart in a depolarization period of Brugada syndrome type 1 is analyzed by the signal analysis device 1 in the first embodiment.
Figure 19:
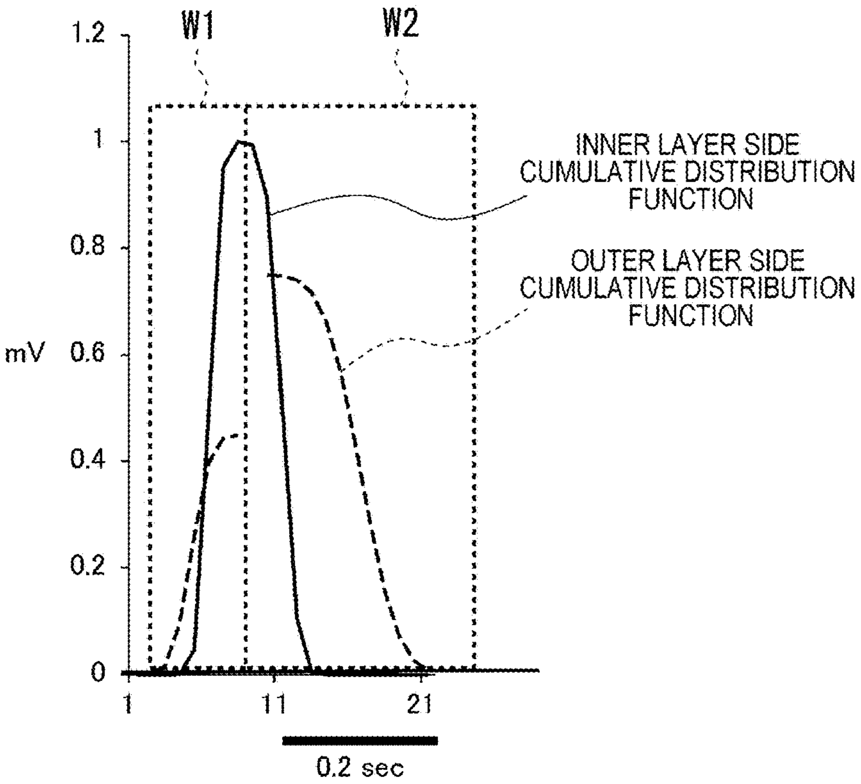
FIG. 19 is a second explanatory diagram in which the electrocardiogram of the target heart in the depolarization period of Brugada syndrome type 1 is analyzed by the signal analysis device 1 in the first embodiment.
Figure 20:
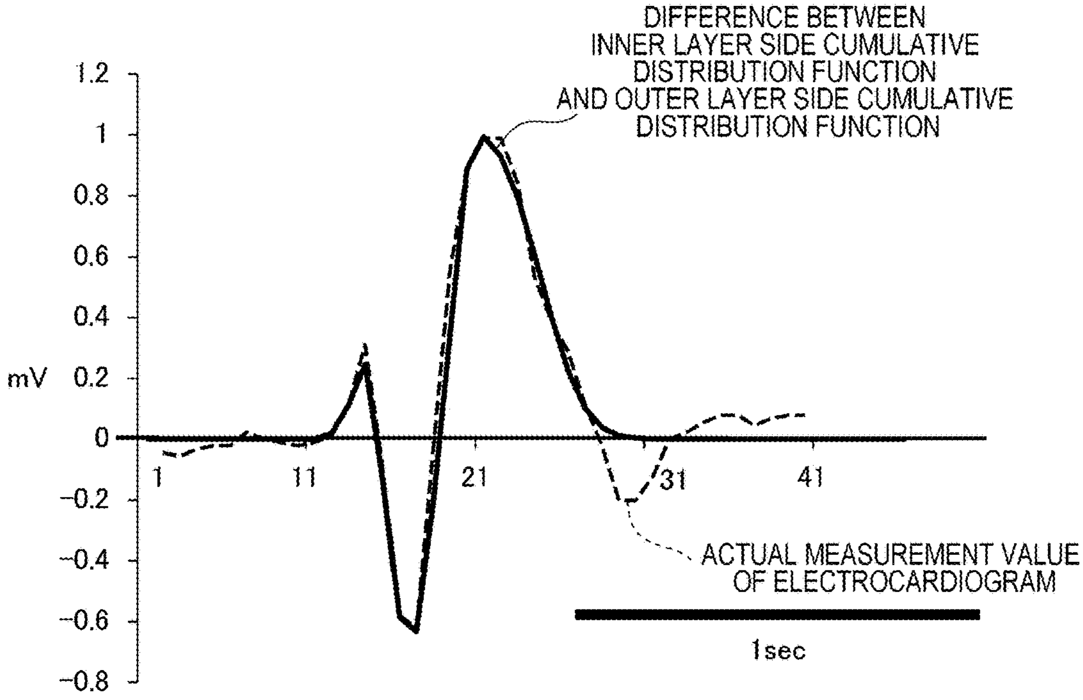
FIG. 20 is a third explanatory diagram in which the electrocardiogram of the target heart in the depolarization period of Brugada syndrome type 1 is analyzed by the signal analysis device 1 in the first embodiment.
Figure 21:
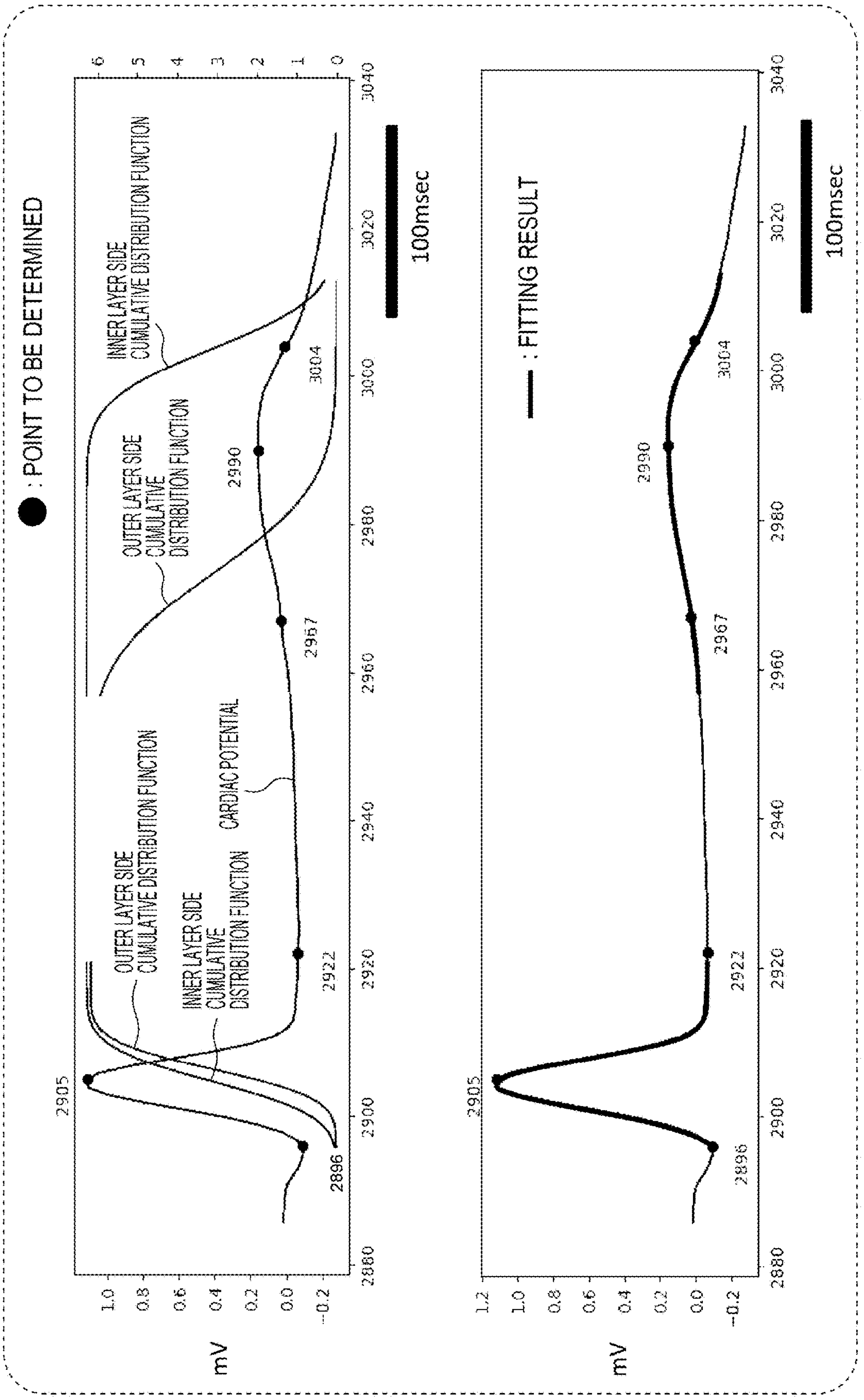
FIG. 21 is a diagram illustrating a first example in which an electrocardiogram is analyzed by the signal analysis device 1 in the first embodiment.
Figure 22:
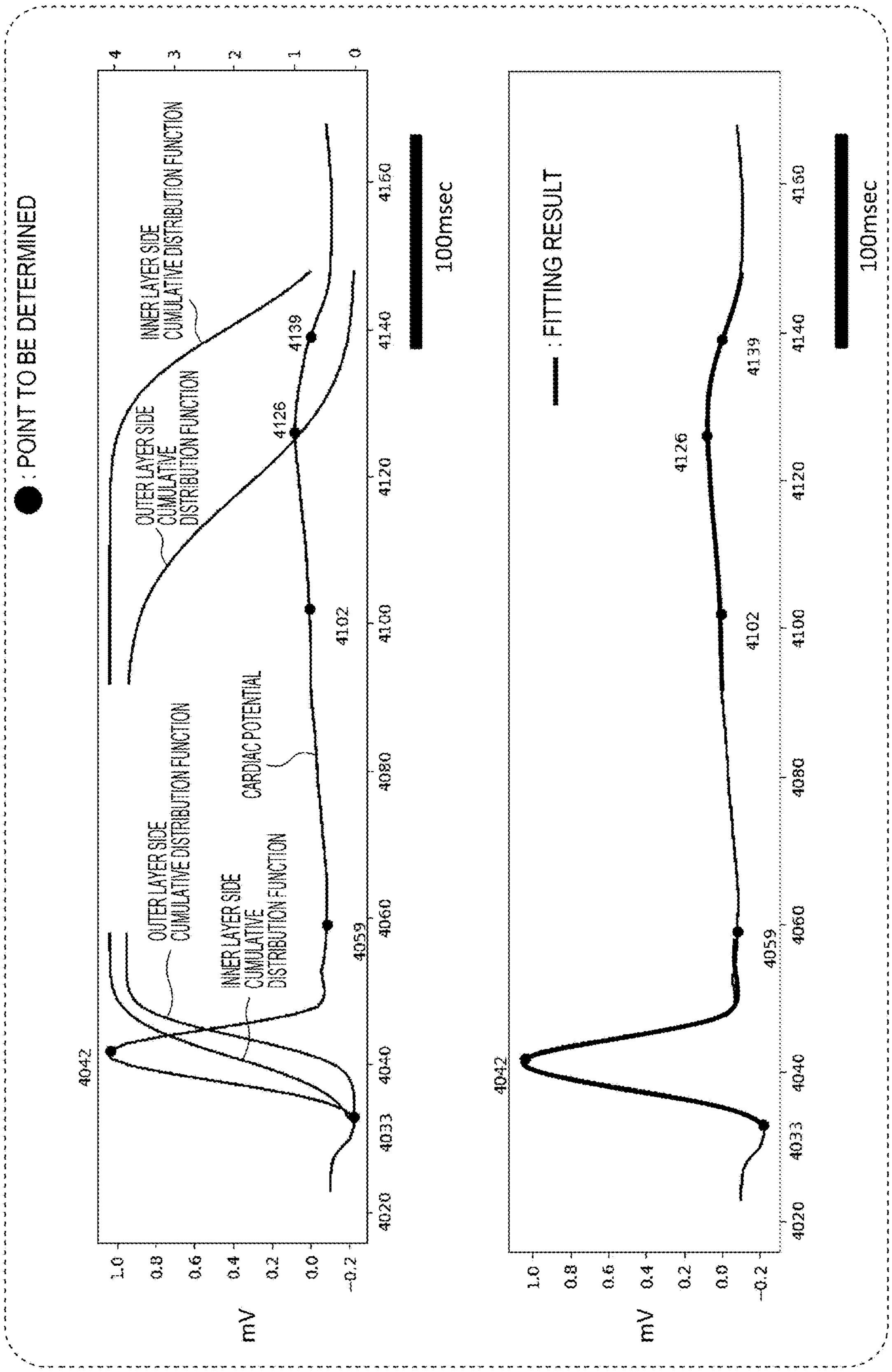
FIG. 22 is a diagram illustrating a second example in which an electrocardiogram is analyzed by the signal analysis device 1 in the first embodiment.
Figure 23:
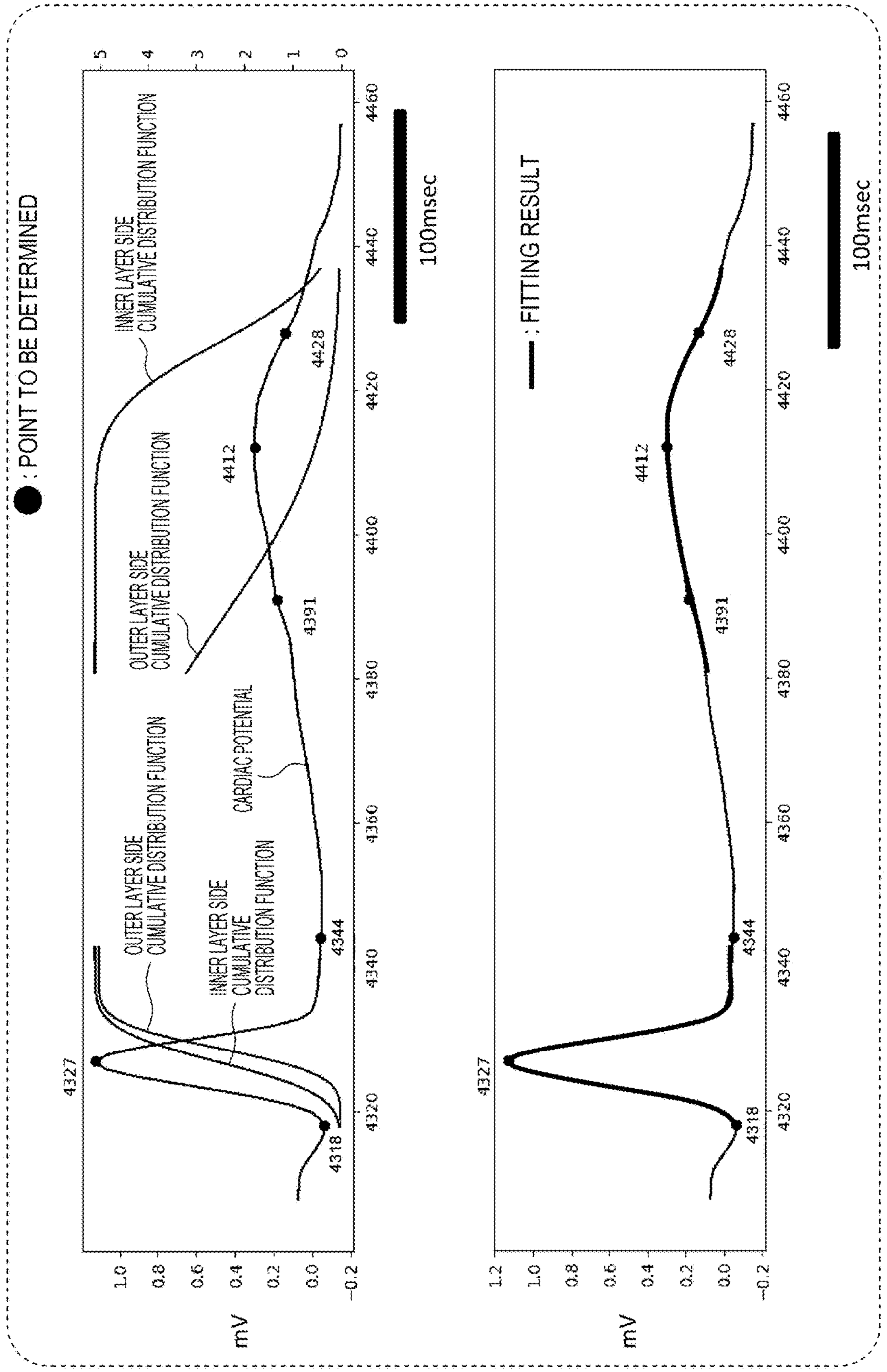
FIG. 23 is a diagram illustrating a third example in which an electrocardiogram is analyzed by the signal analysis device 1 in the first embodiment.
Figure 24:
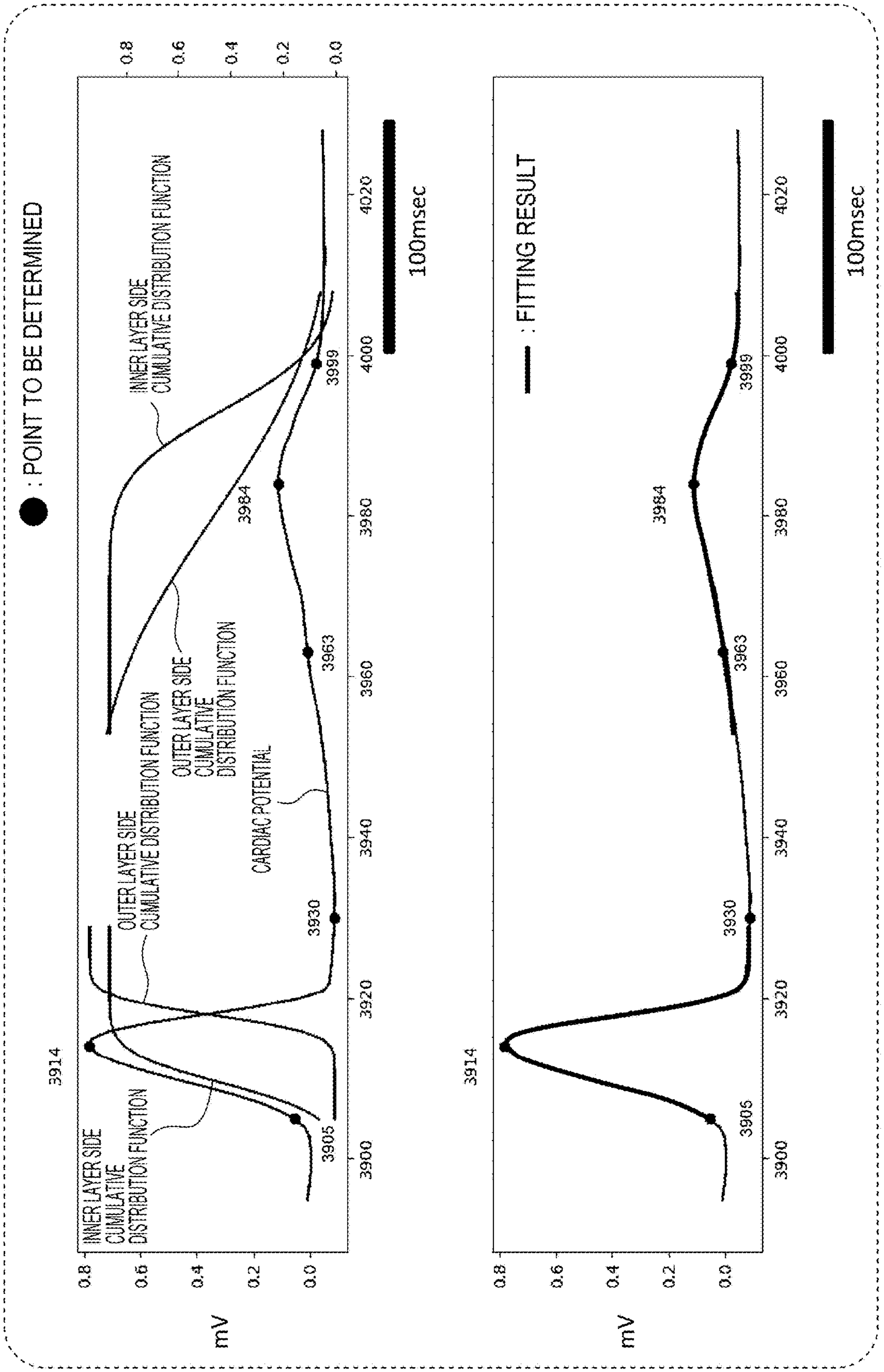
FIG. 24 is a diagram illustrating a fourth example in which an electrocardiogram is analyzed by the signal analysis device 1 in the first embodiment.
Figure 25:
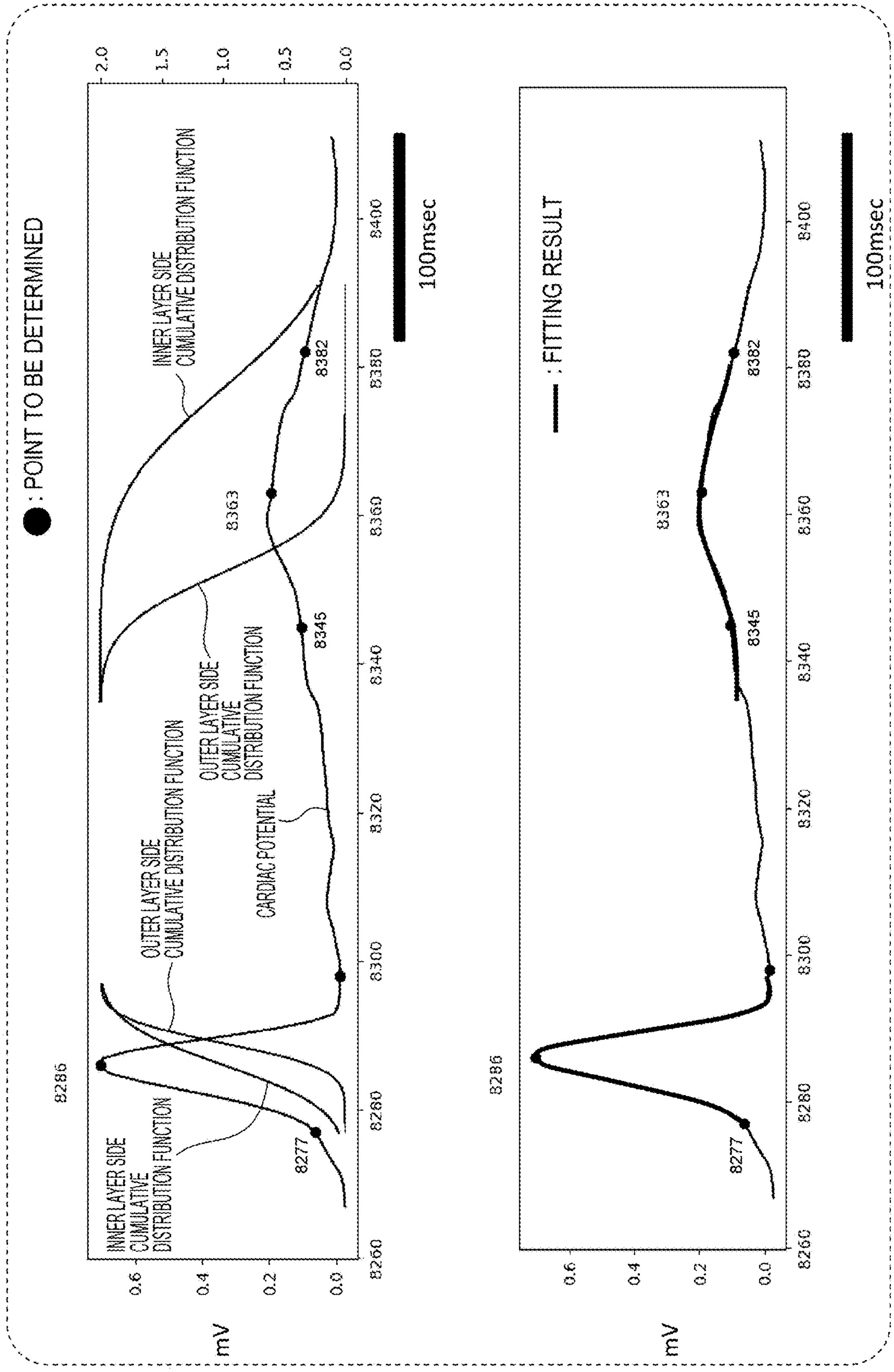
FIG. 25 is a diagram illustrating a fifth example in which an electrocardiogram is analyzed by the signal analysis device 1 in the first embodiment.
Figure 26:
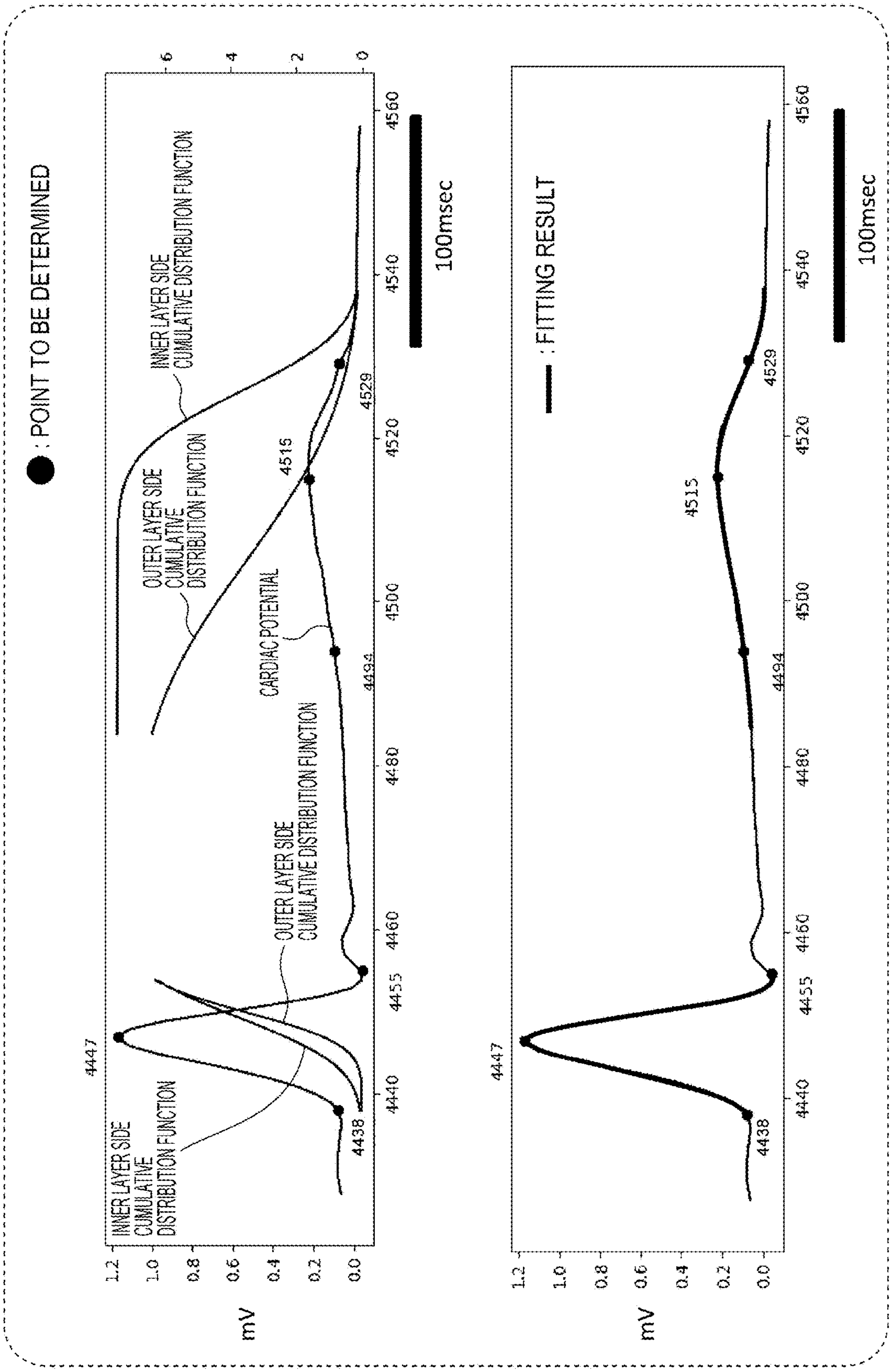
FIG. 26 is a diagram illustrating a sixth example in which an electrocardiogram is analyzed by the signal analysis device 1 in the first embodiment.
Figure 27:
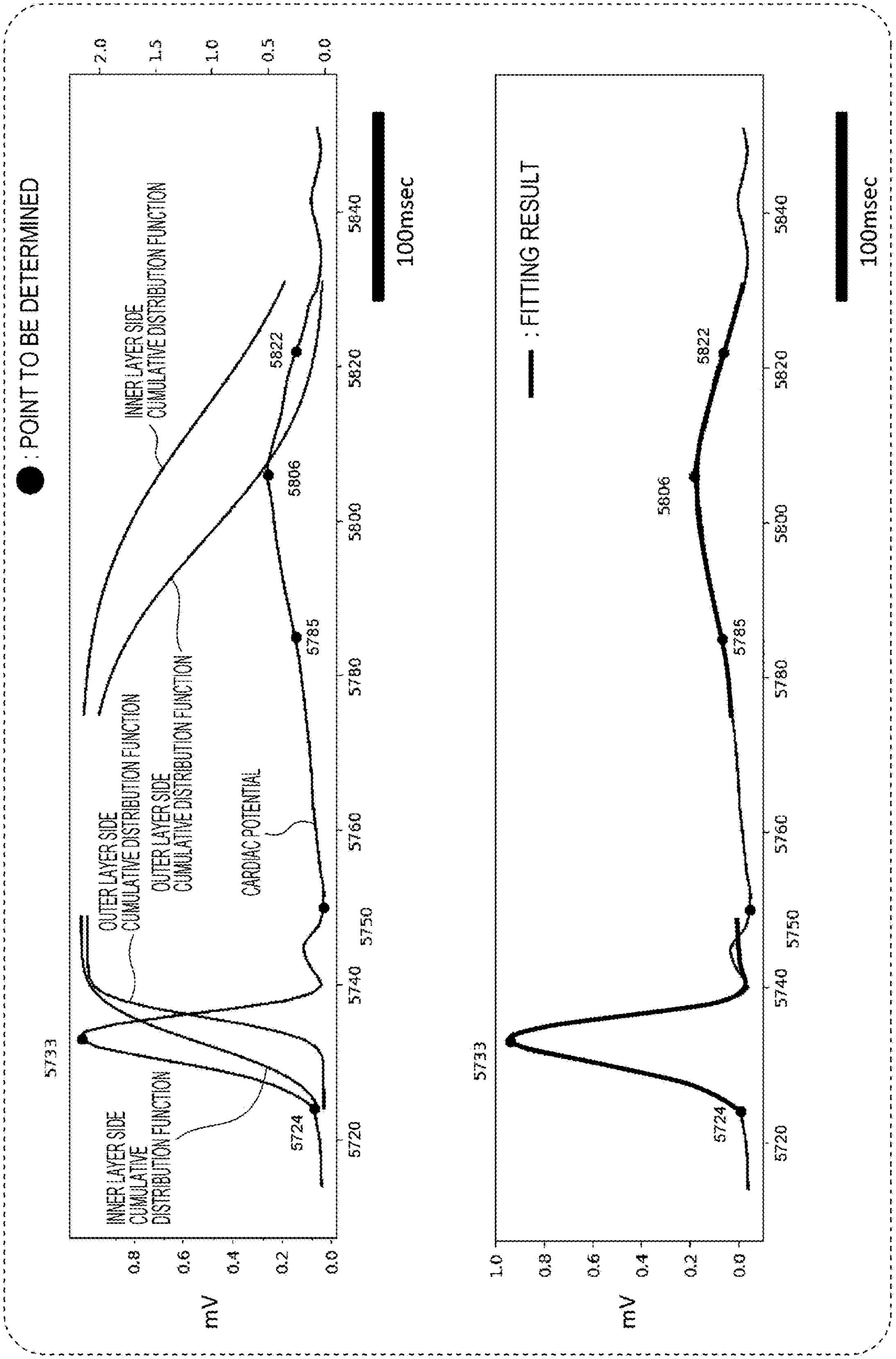
FIG. 27 is a diagram illustrating a seventh example in which an electrocardiogram is analyzed by the signal analysis device 1 in the first embodiment.
Figure 28:
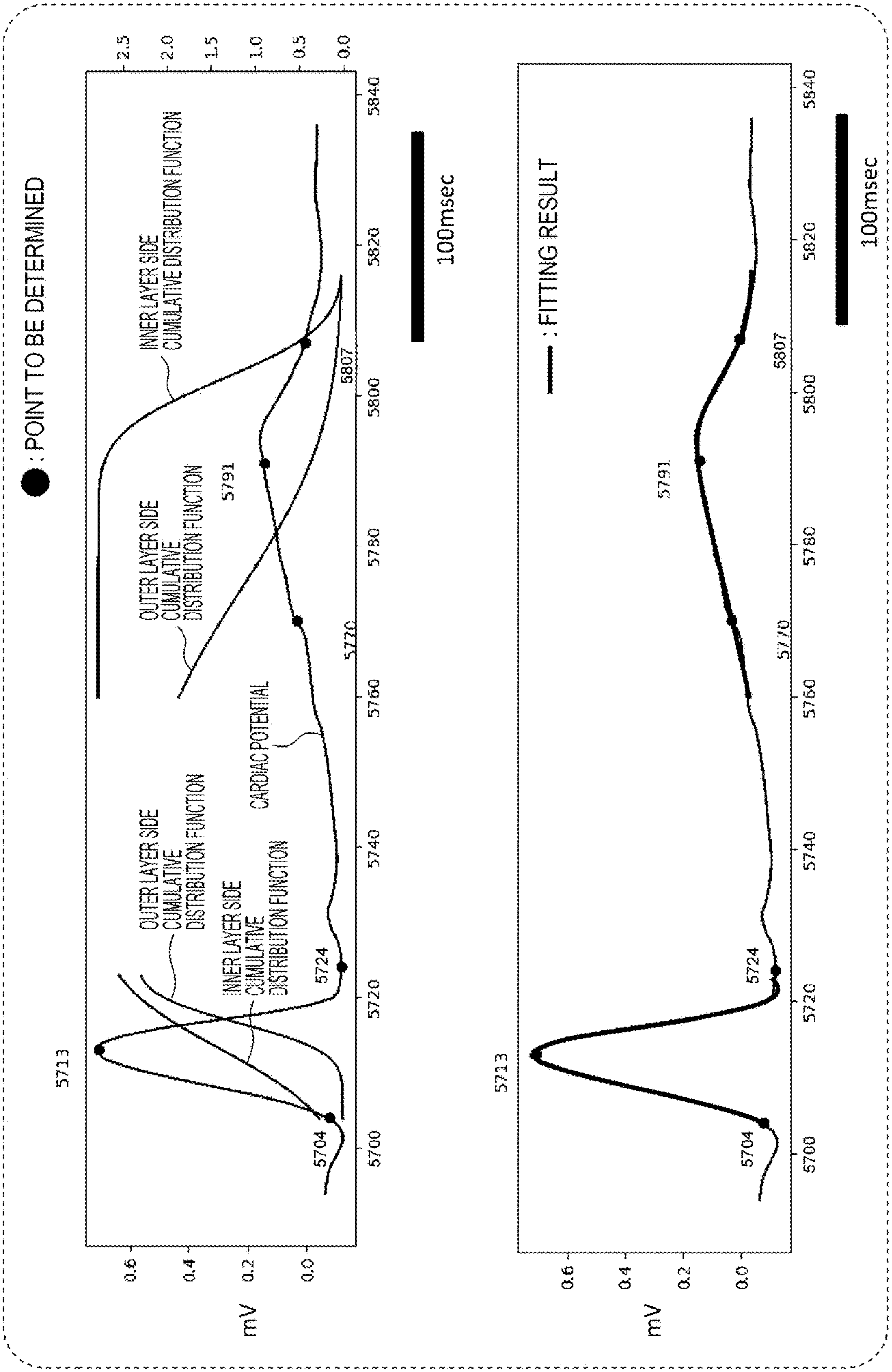
FIG. 28 is a diagram illustrating an eighth example in which an electrocardiogram is analyzed by the signal analysis device 1 in the first embodiment.
Figure 29:
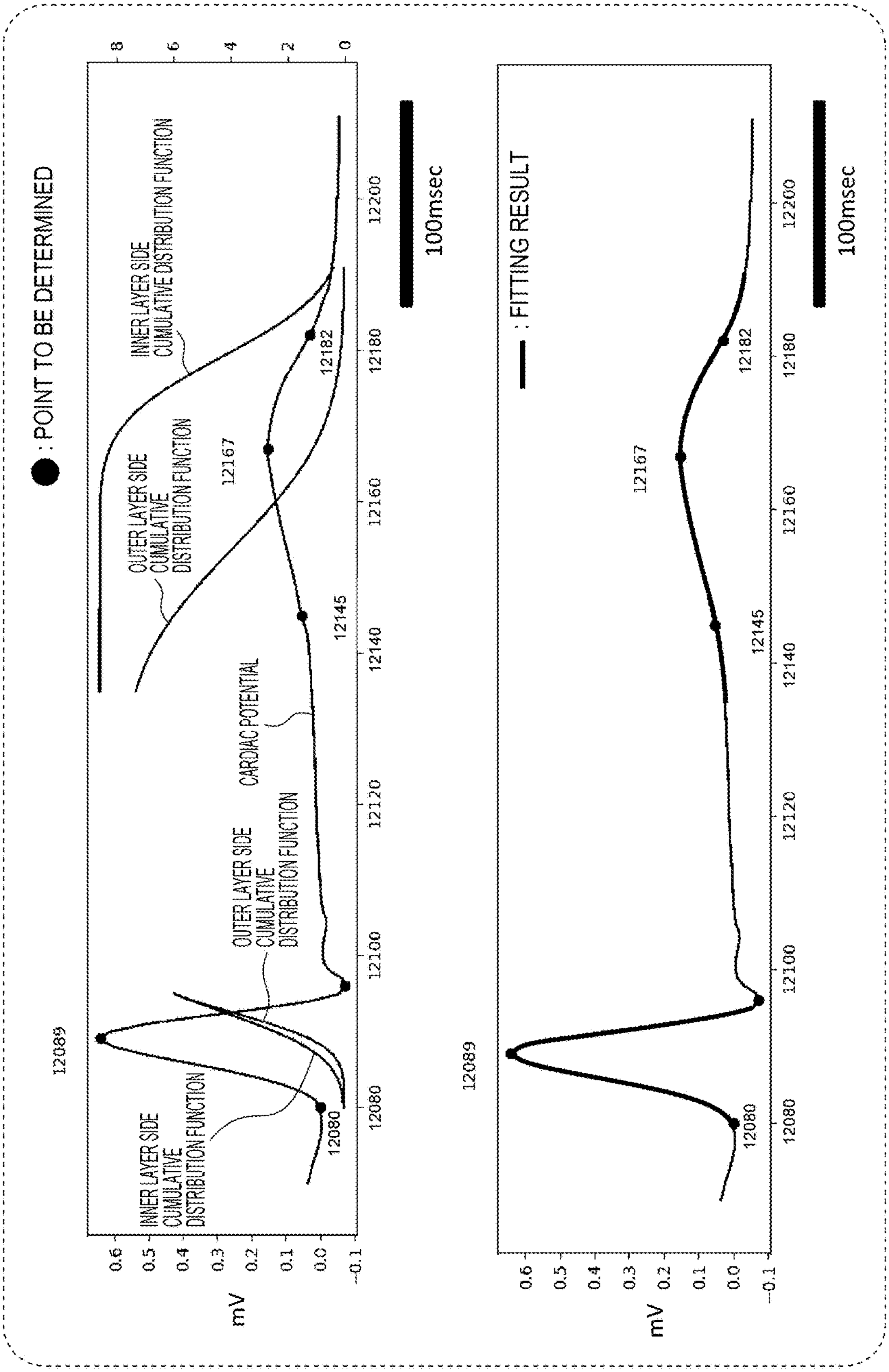
FIG. 29 is a diagram illustrating a ninth example in which an electrocardiogram is analyzed by the signal analysis device 1 in the first embodiment.
Figure 30:
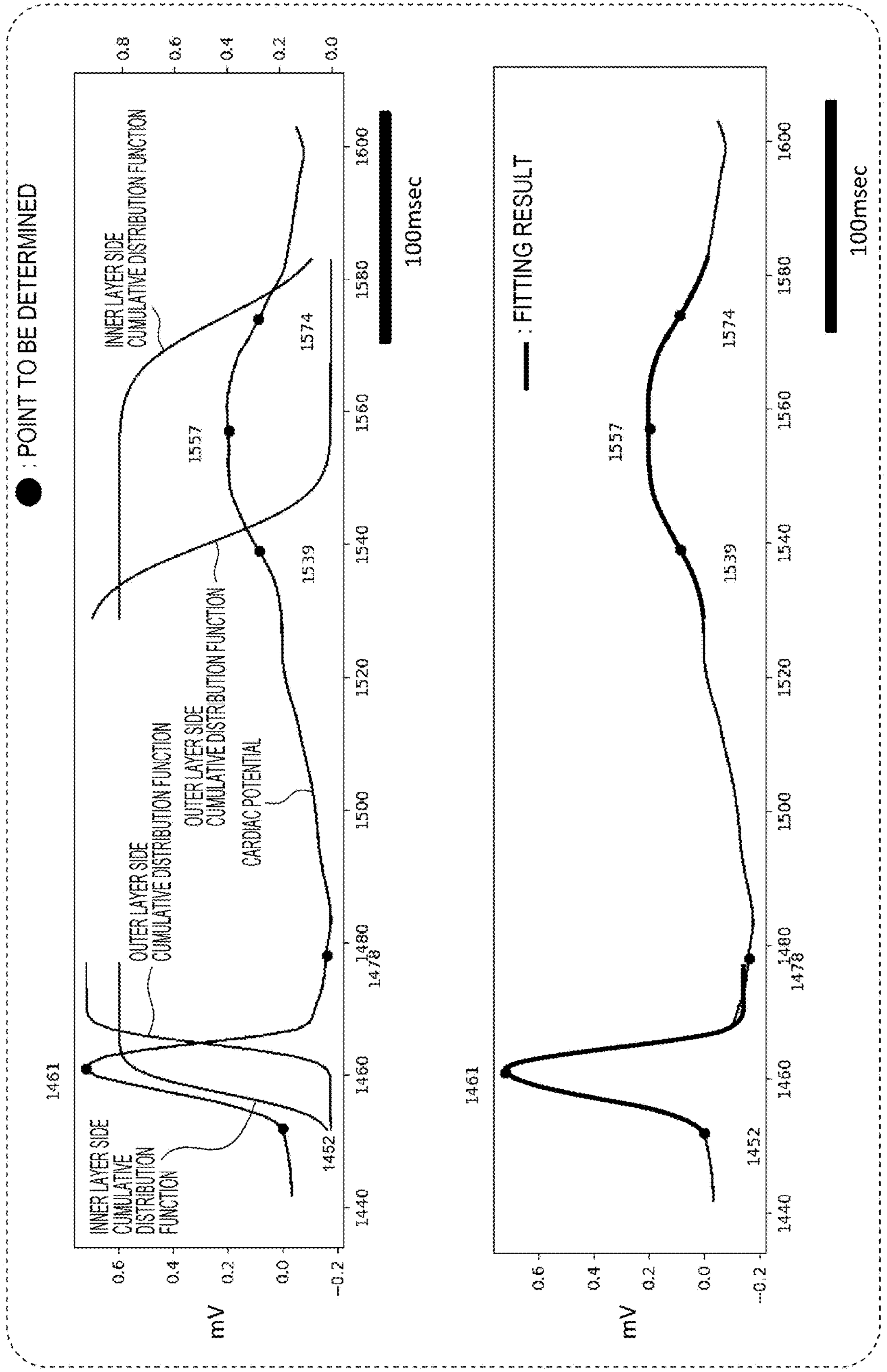
FIG. 30 is a diagram illustrating a tenth example in which an electrocardiogram is analyzed by the signal analysis device 1 in the first embodiment.
Figure 31:
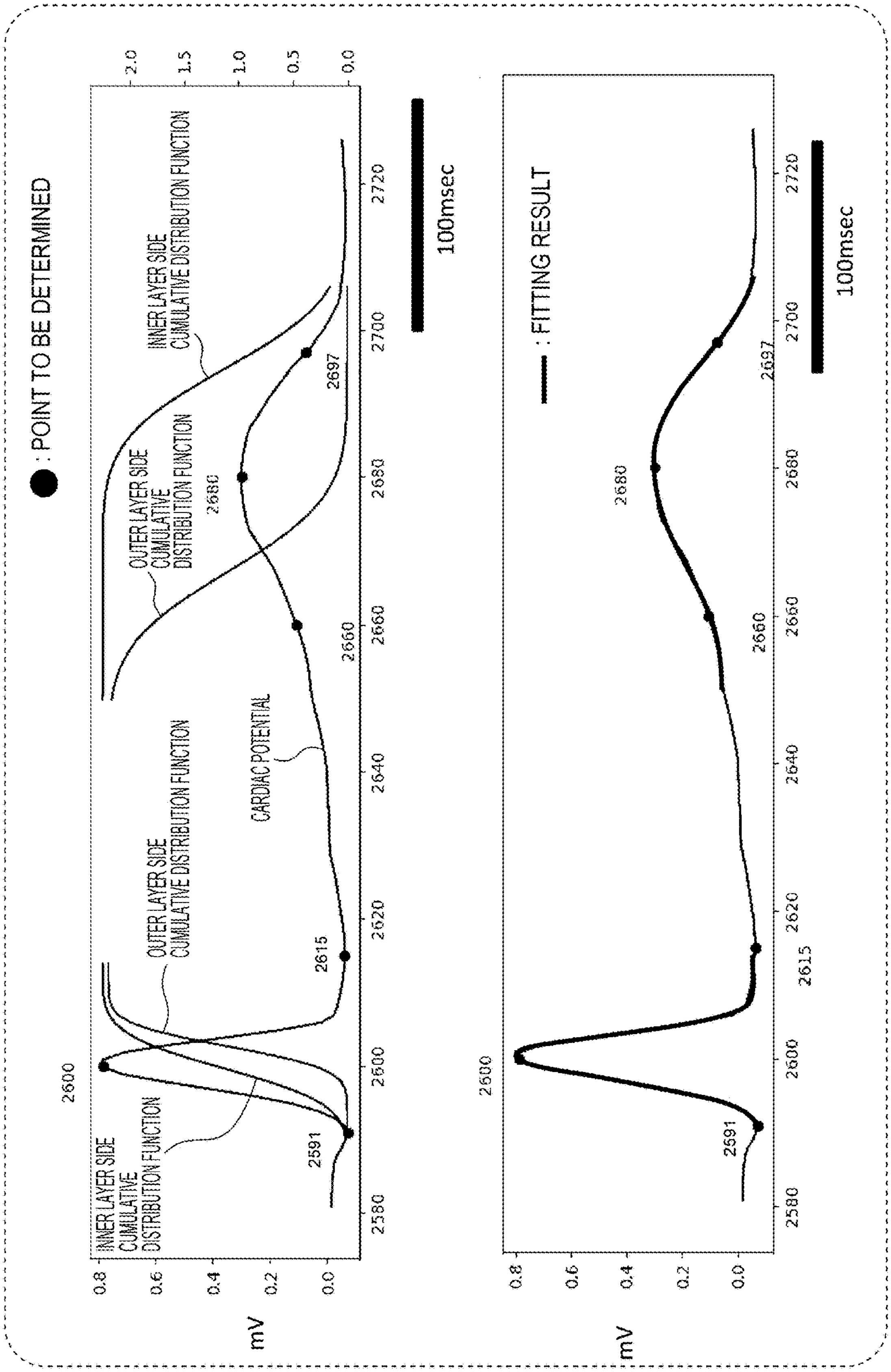
FIG. 31 is a diagram illustrating an eleventh example in which an electrocardiogram is analyzed by the signal analysis device 1 in the first embodiment.
Figure 32:
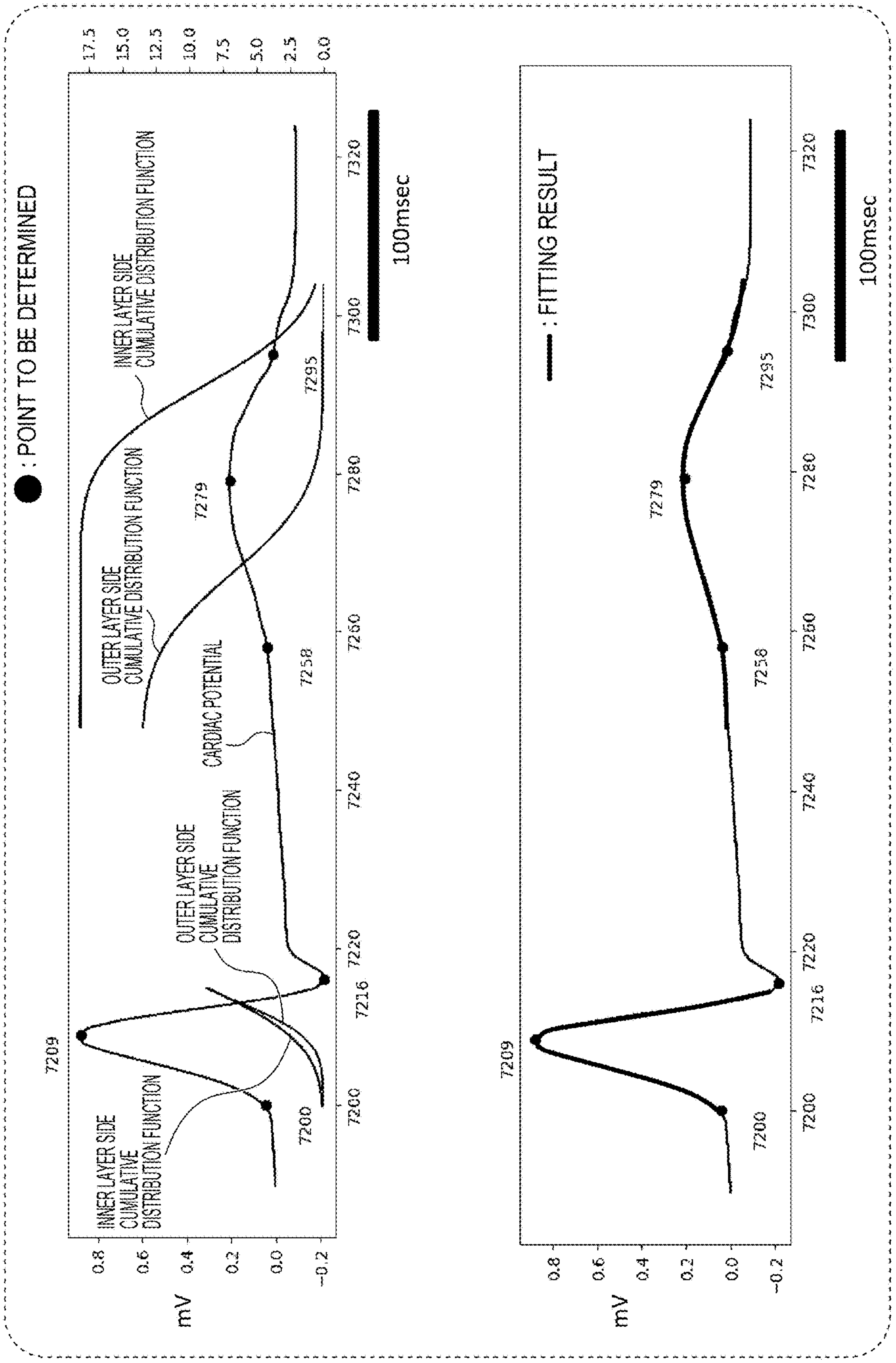
FIG. 32 is a diagram illustrating a twelfth example in which an electrocardiogram is analyzed by the signal analysis device 1 in the first embodiment.
Figure 33:
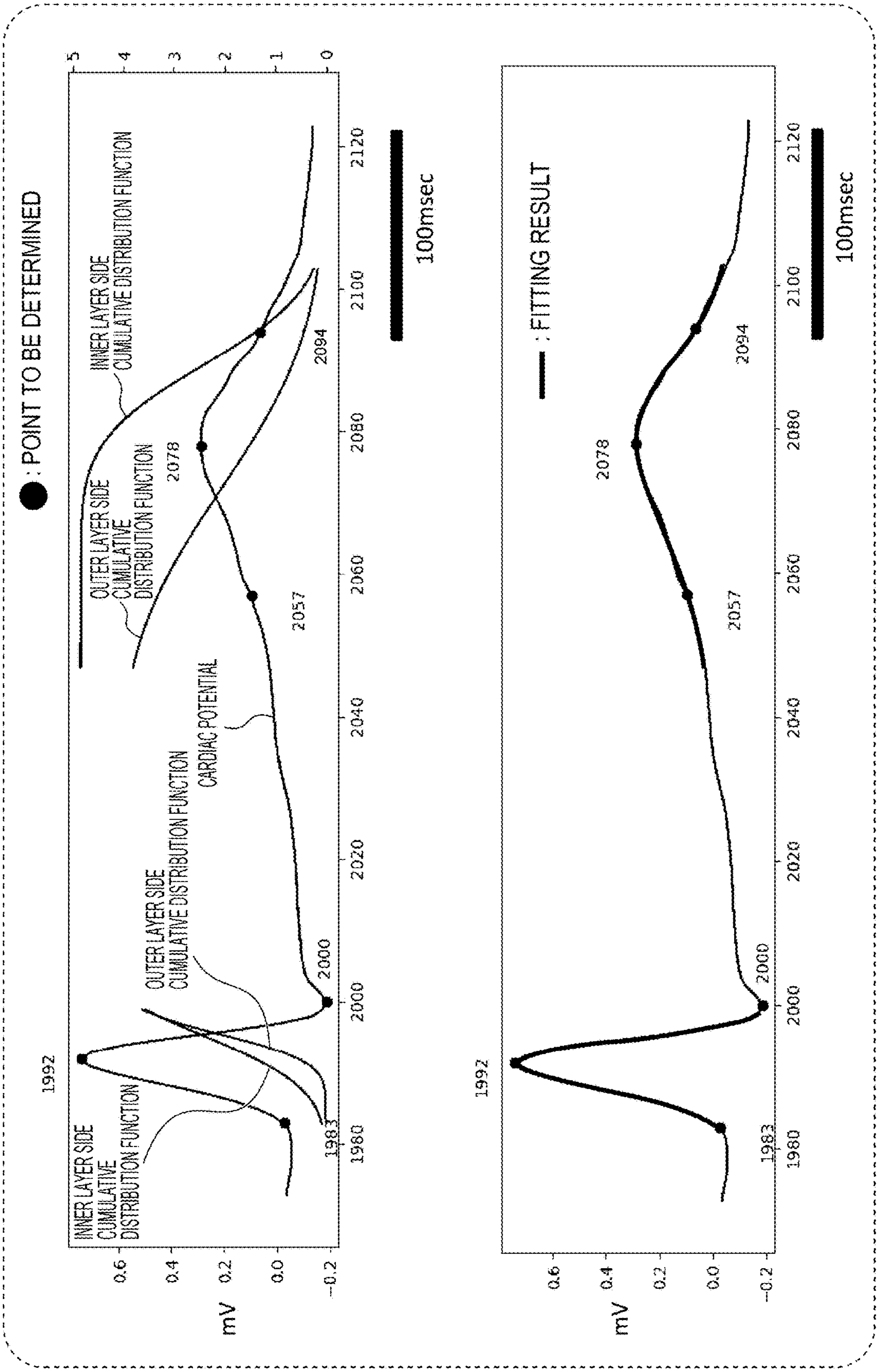
FIG. 33 is a diagram illustrating a thirteenth example in which an electrocardiogram is analyzed by the signal analysis device 1 in the first embodiment.
Figure 34:
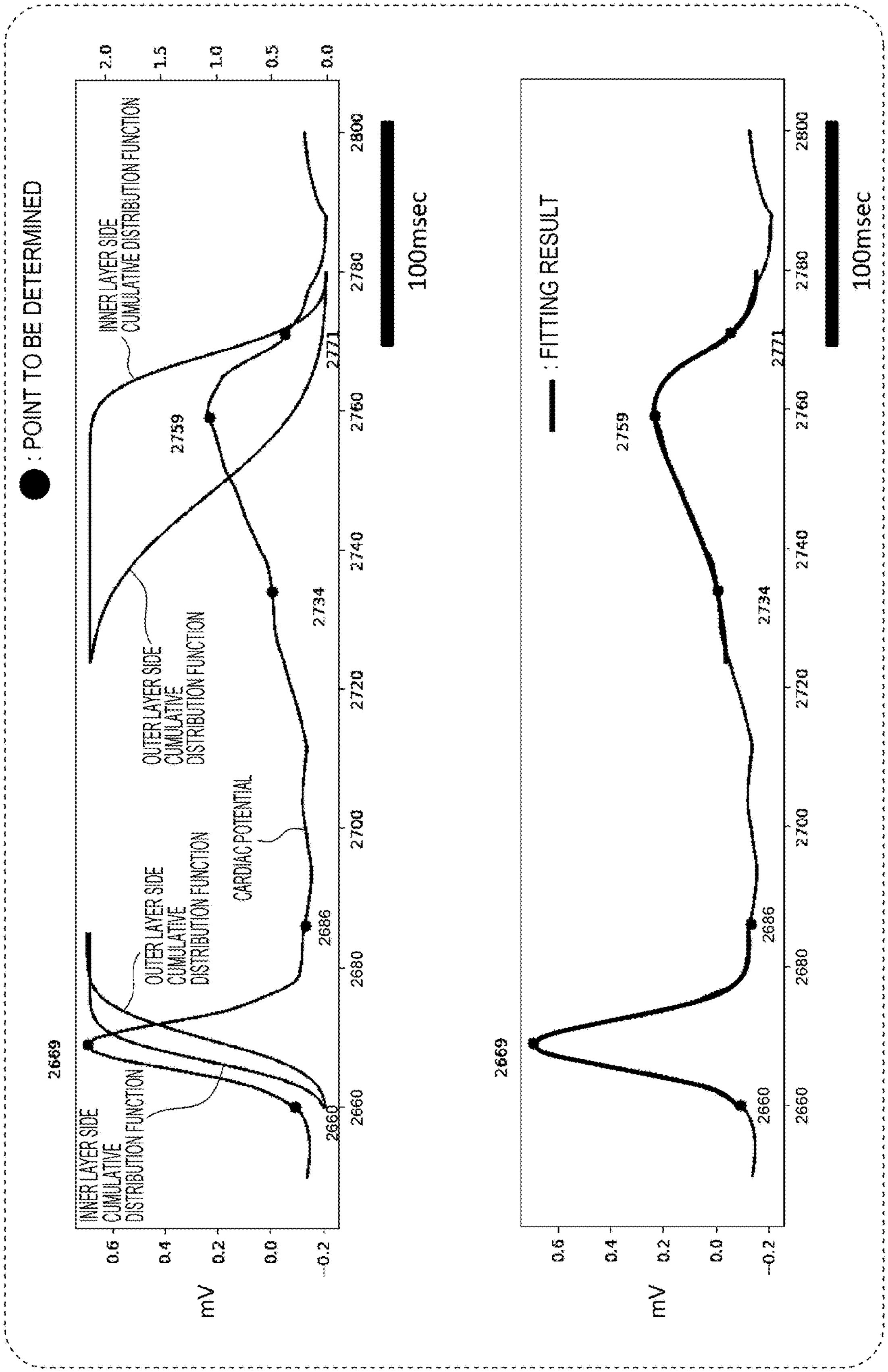
FIG. 34 is a diagram illustrating a fourteenth example in which an electrocardiogram is analyzed by the signal analysis device 1 in the first embodiment.
Figure 35:
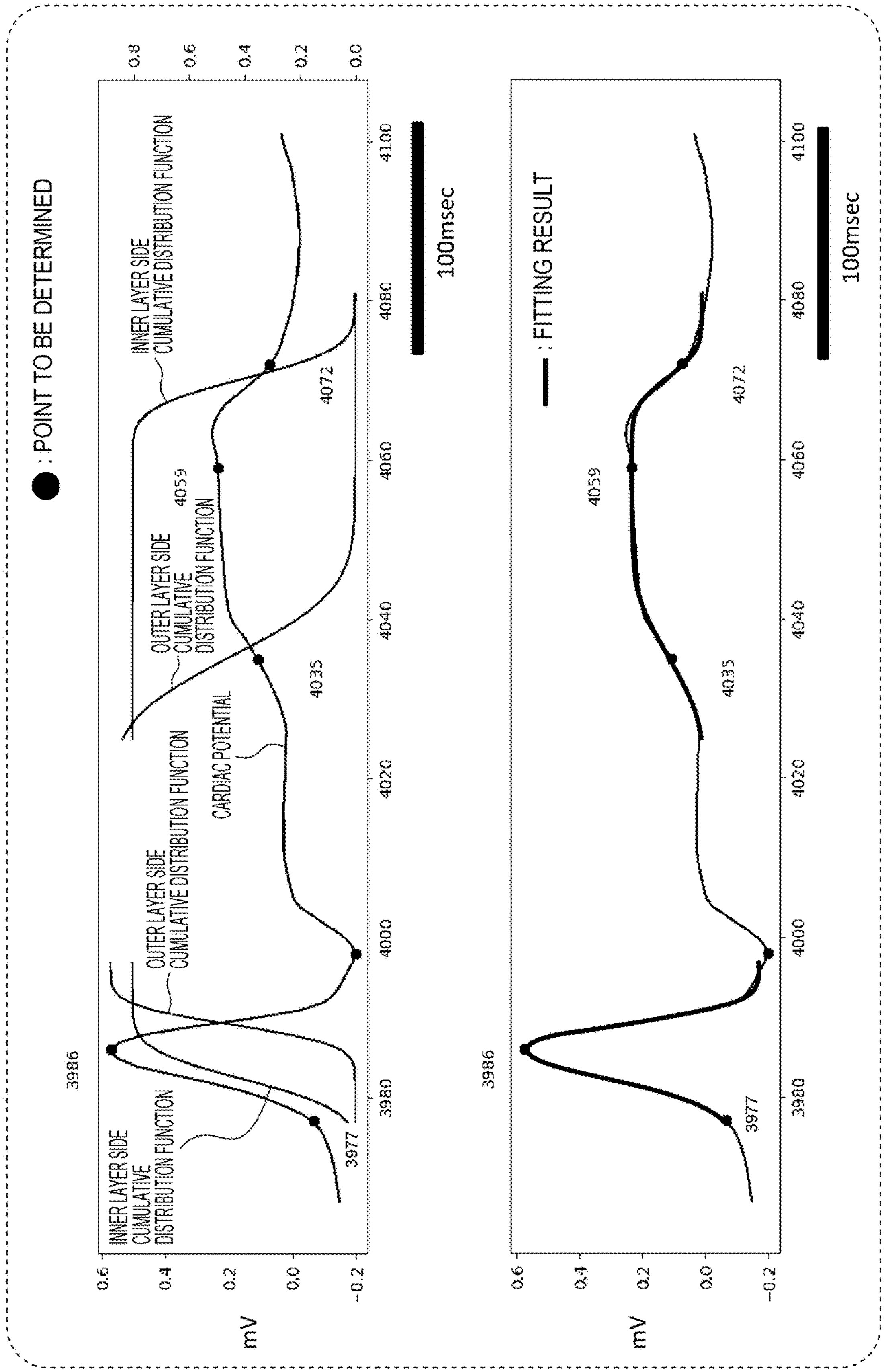
FIG. 35 is a diagram illustrating a fifteenth example in which an electrocardiogram is analyzed by the signal analysis device 1 in the first embodiment.
Figure 36:
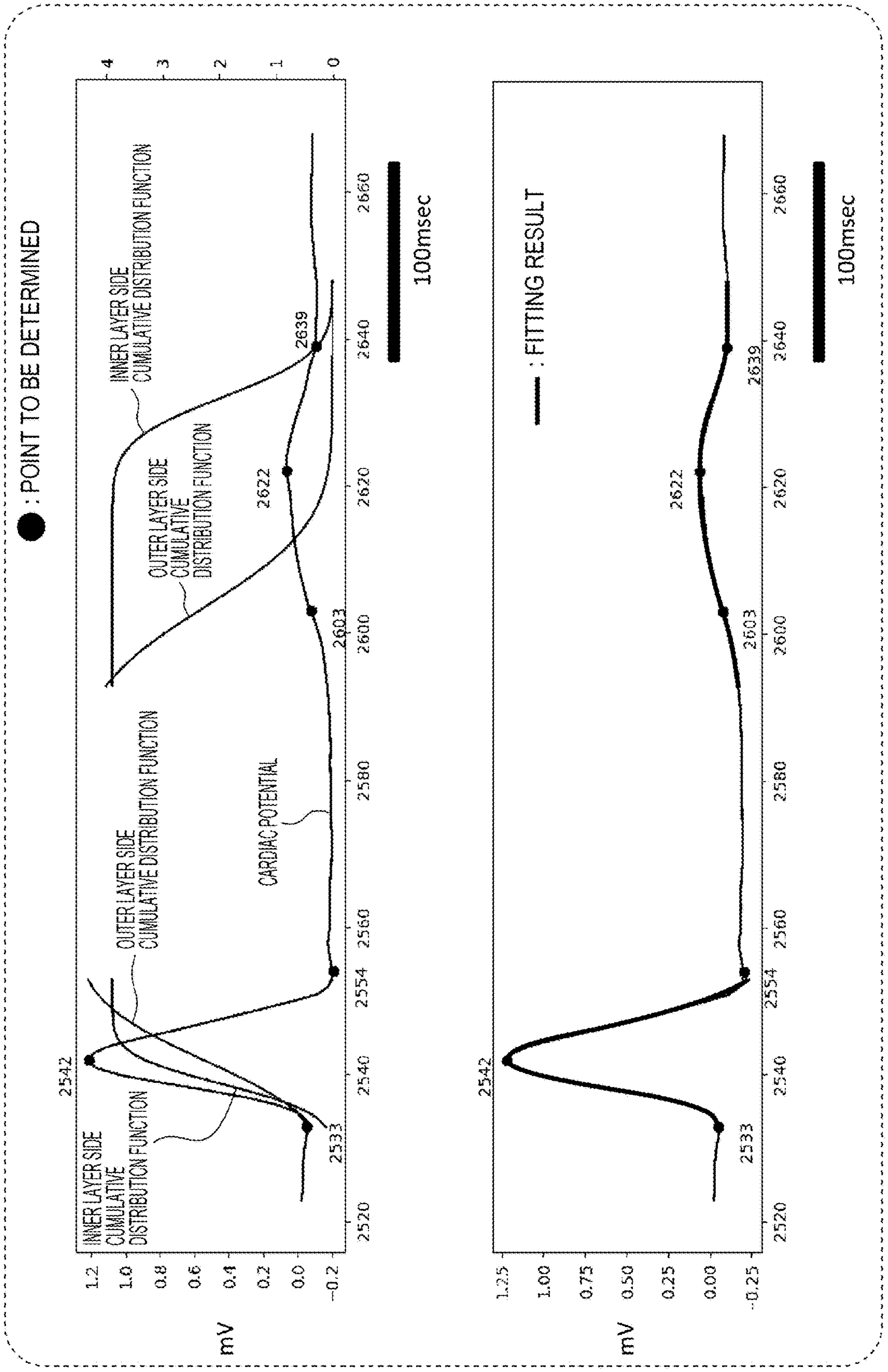
FIG. 36 is a diagram illustrating a sixteenth example in which an electrocardiogram is analyzed by the signal analysis device 1 in the first embodiment.
Figure 37:
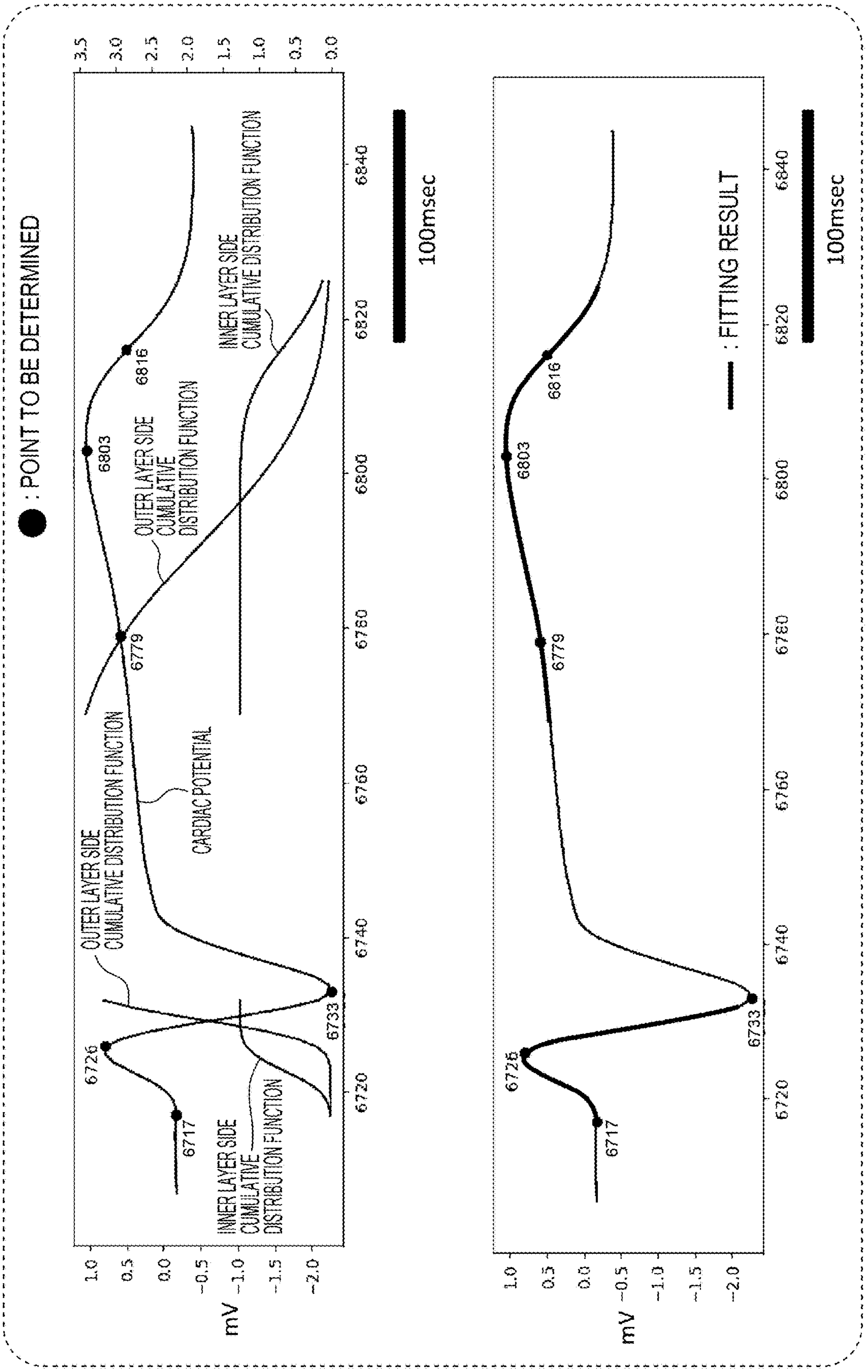
FIG. 37 is a diagram illustrating a seventeenth example in which an electrocardiogram is analyzed by the signal analysis device 1 in the first embodiment.
Figure 38:
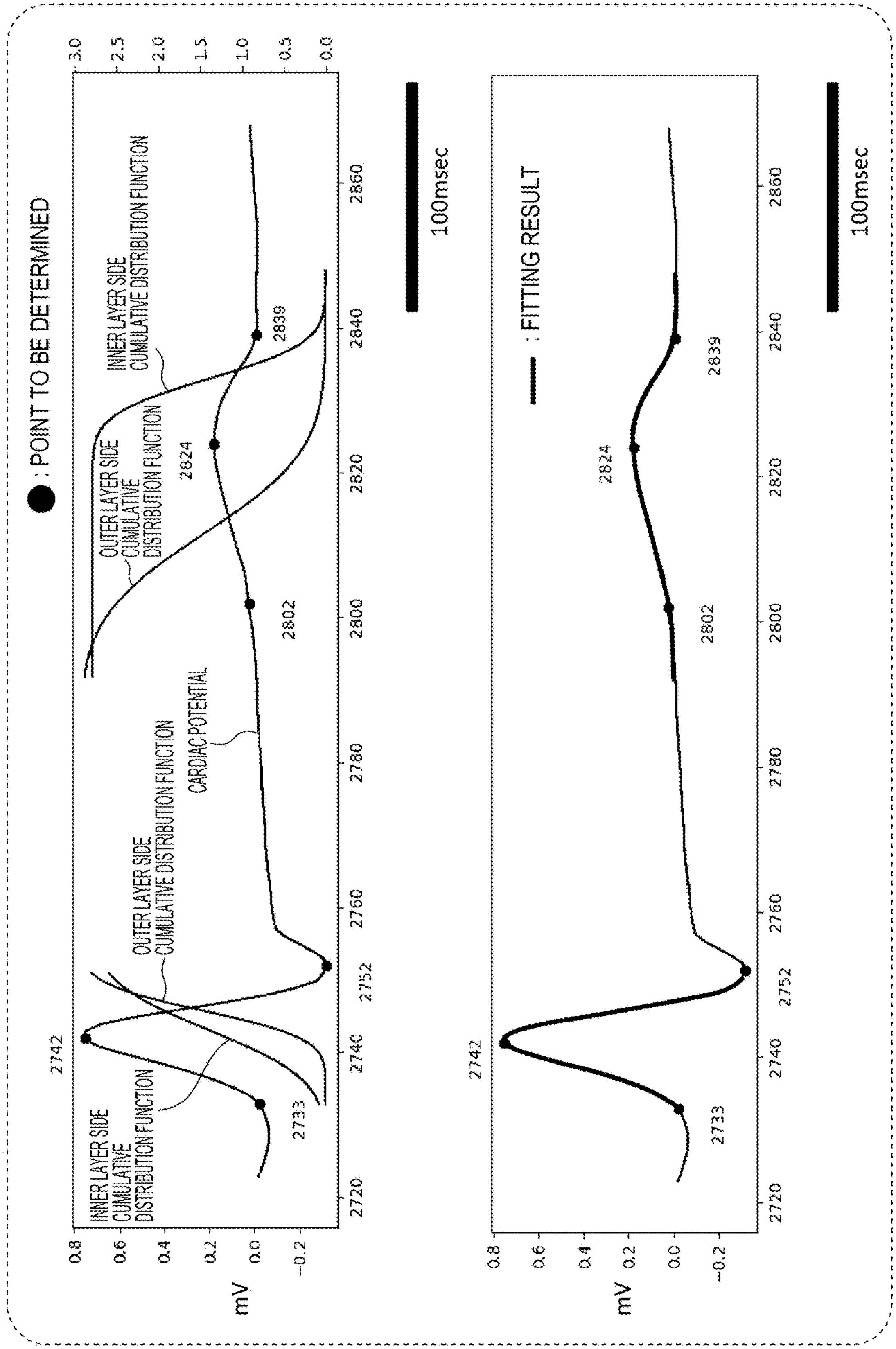
FIG. 38 is a diagram illustrating an eighteenth example in which an electrocardiogram is analyzed by the signal analysis device 1 in the first embodiment.
Figure 39:
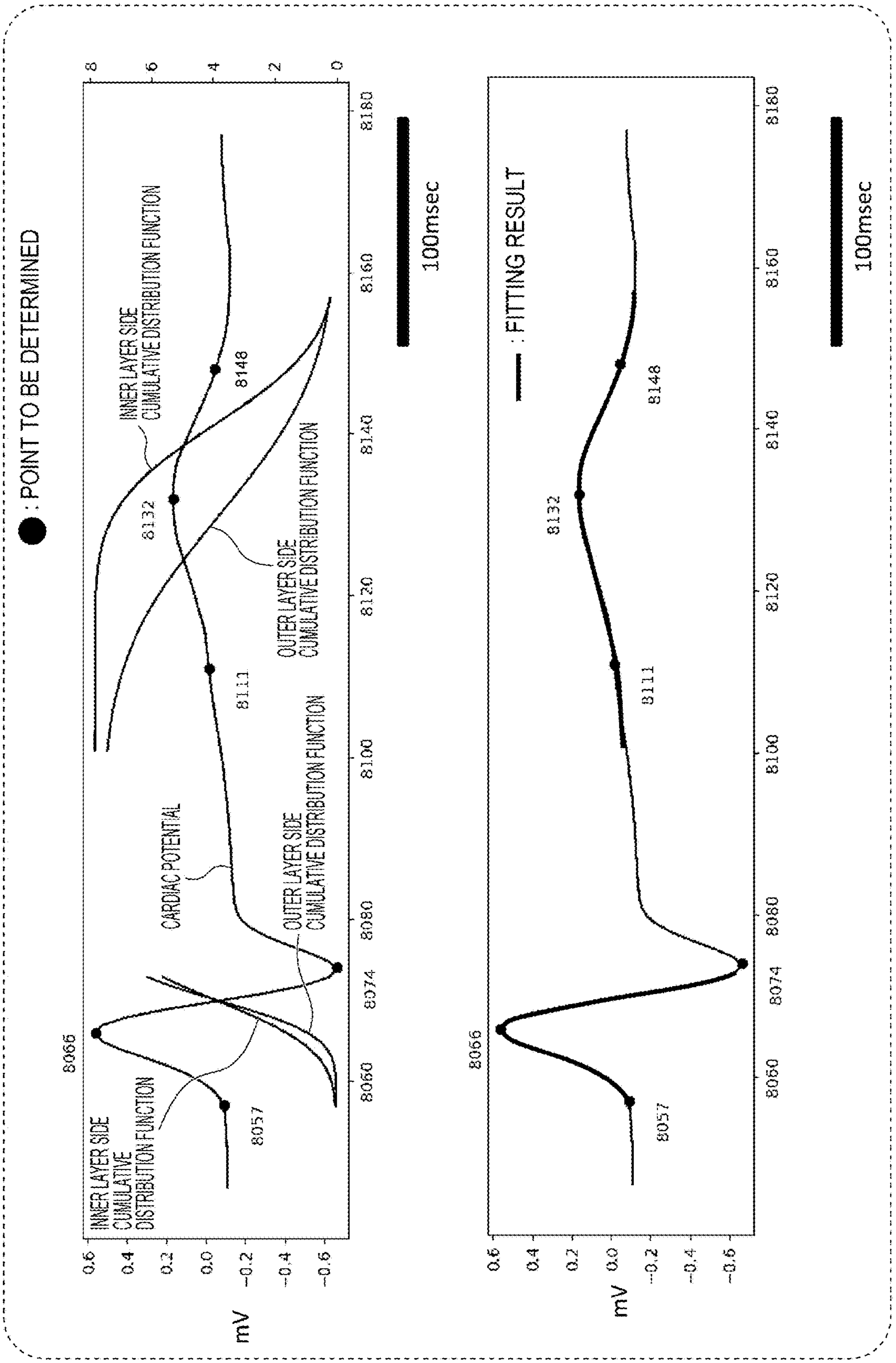
FIG. 39 is a diagram illustrating a nineteenth example in which an electrocardiogram is analyzed by the signal analysis device 1 in the first embodiment.
Figure 40:
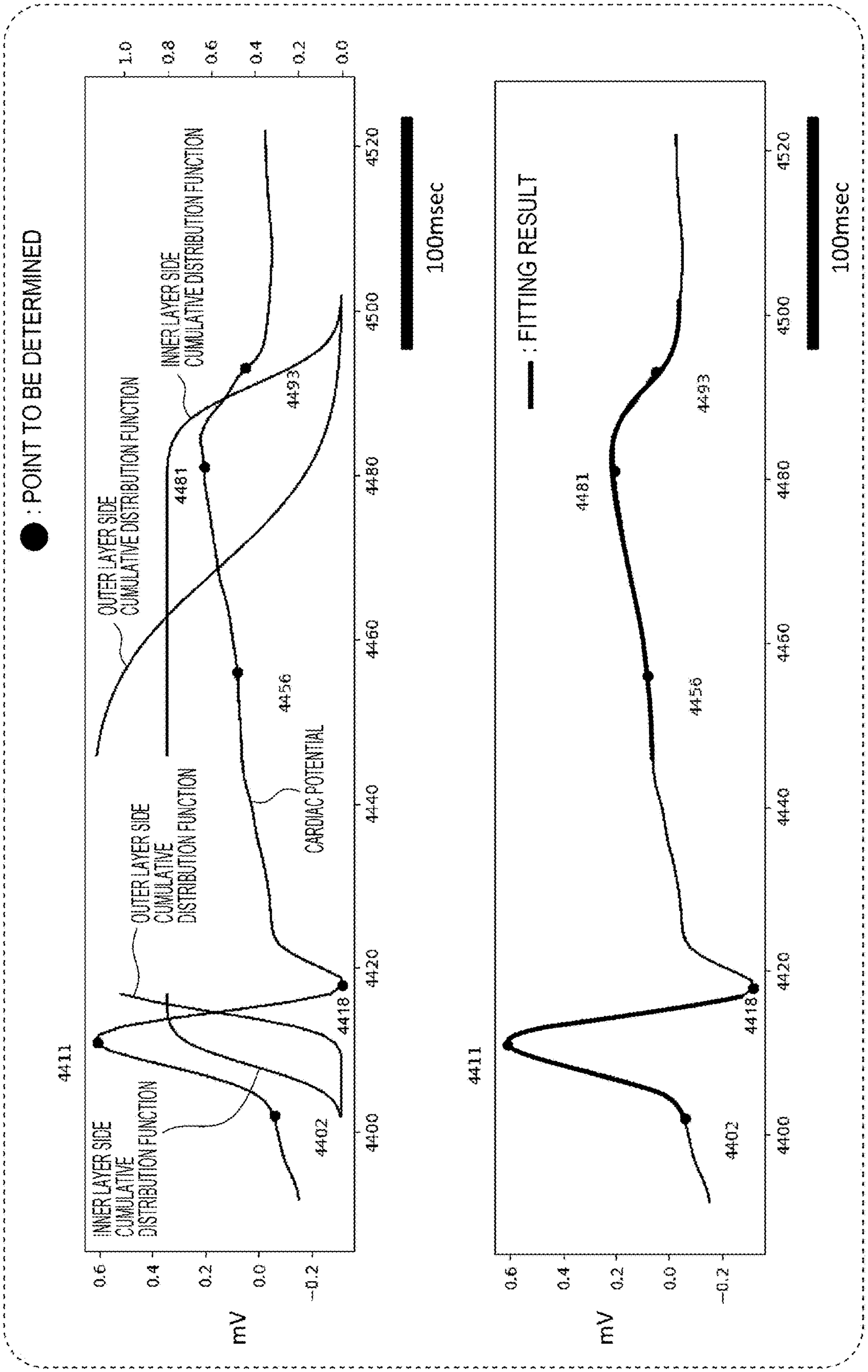
FIG. 40 is a diagram illustrating a twentieth example in which an electrocardiogram is analyzed by the signal analysis device 1 in the first embodiment.
Figure 41:
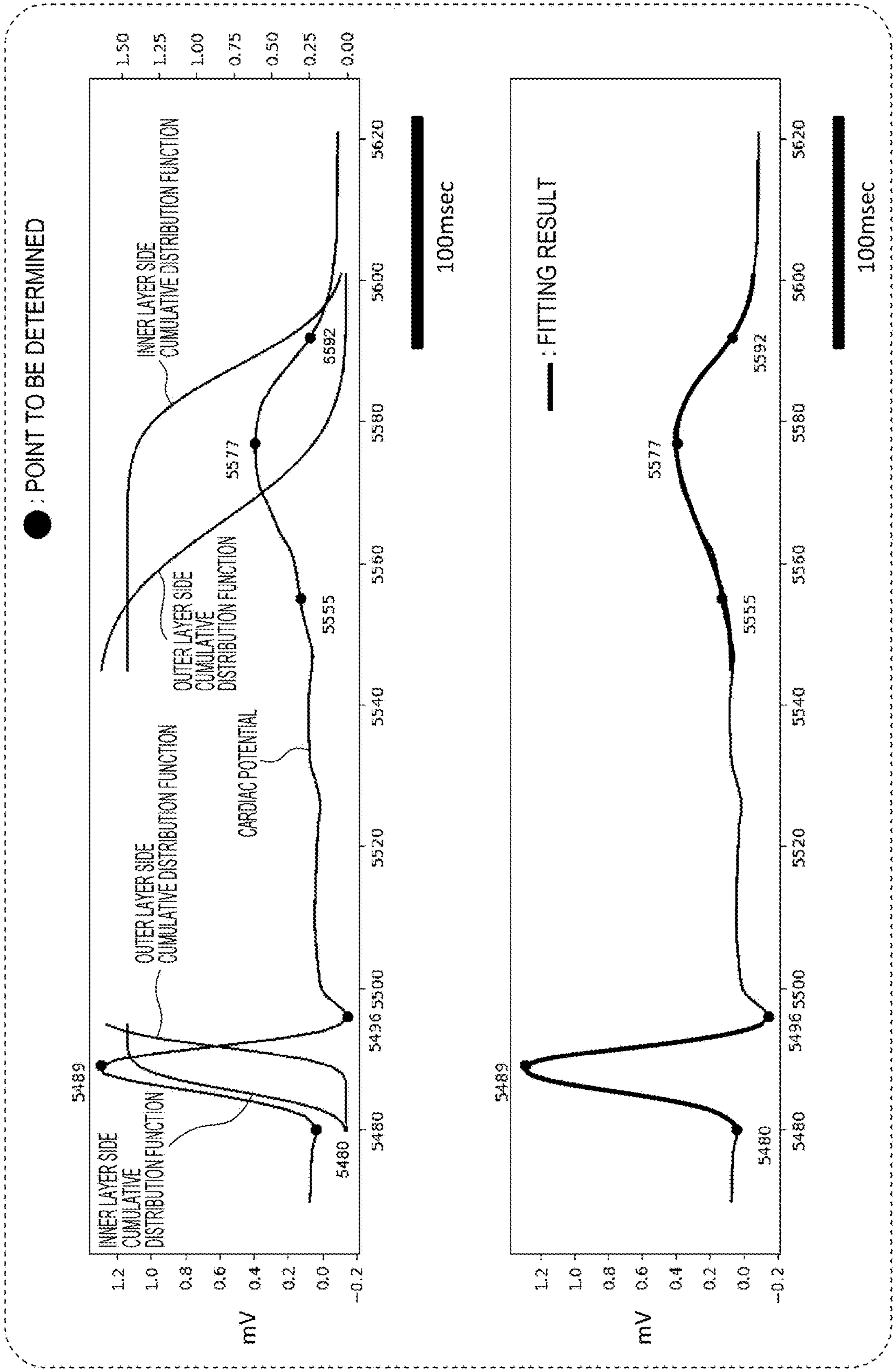
FIG. 41 is a diagram illustrating a twenty-first example in which an electrocardiogram is analyzed by the signal analysis device 1 in the first embodiment.
Figure 42:
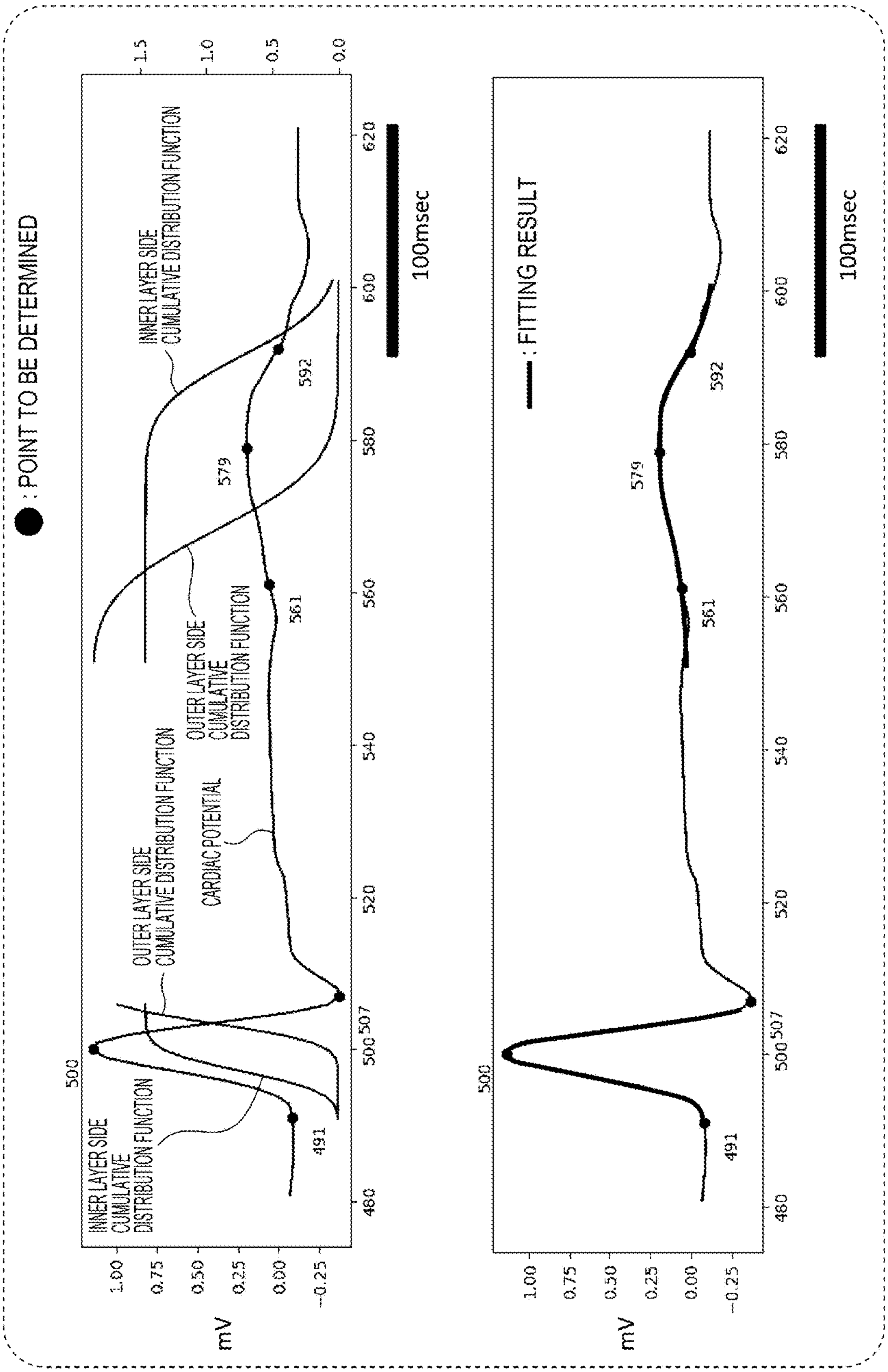
FIG. 42 is a diagram illustrating a twenty-second example in which an electrocardiogram is analyzed by the signal analysis device 1 in the first embodiment.
Figure 43:
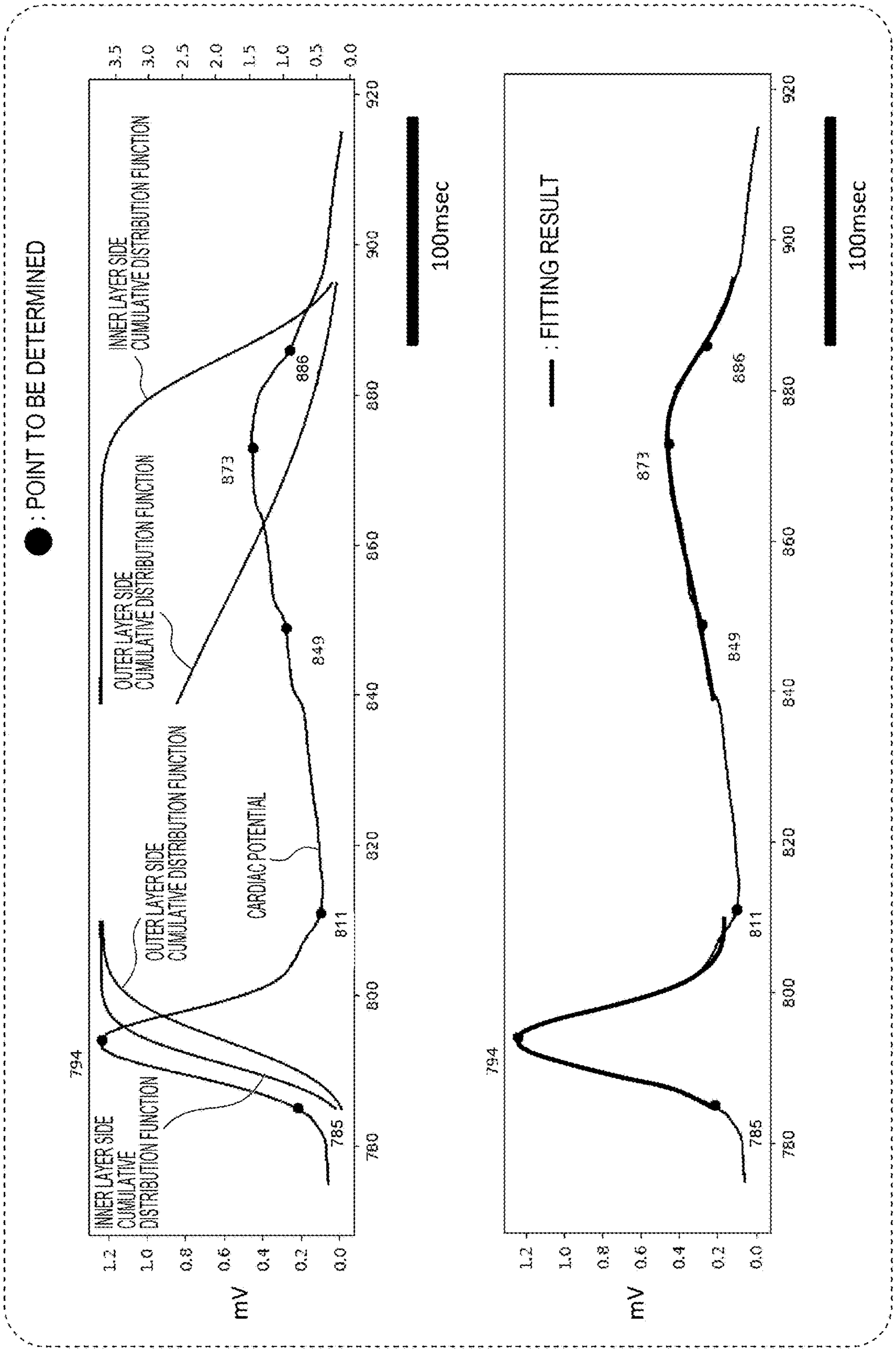
FIG. 43 is a diagram illustrating a twenty-third example in which an electrocardiogram is analyzed by the signal analysis device 1 in the first embodiment.
Figure 44:
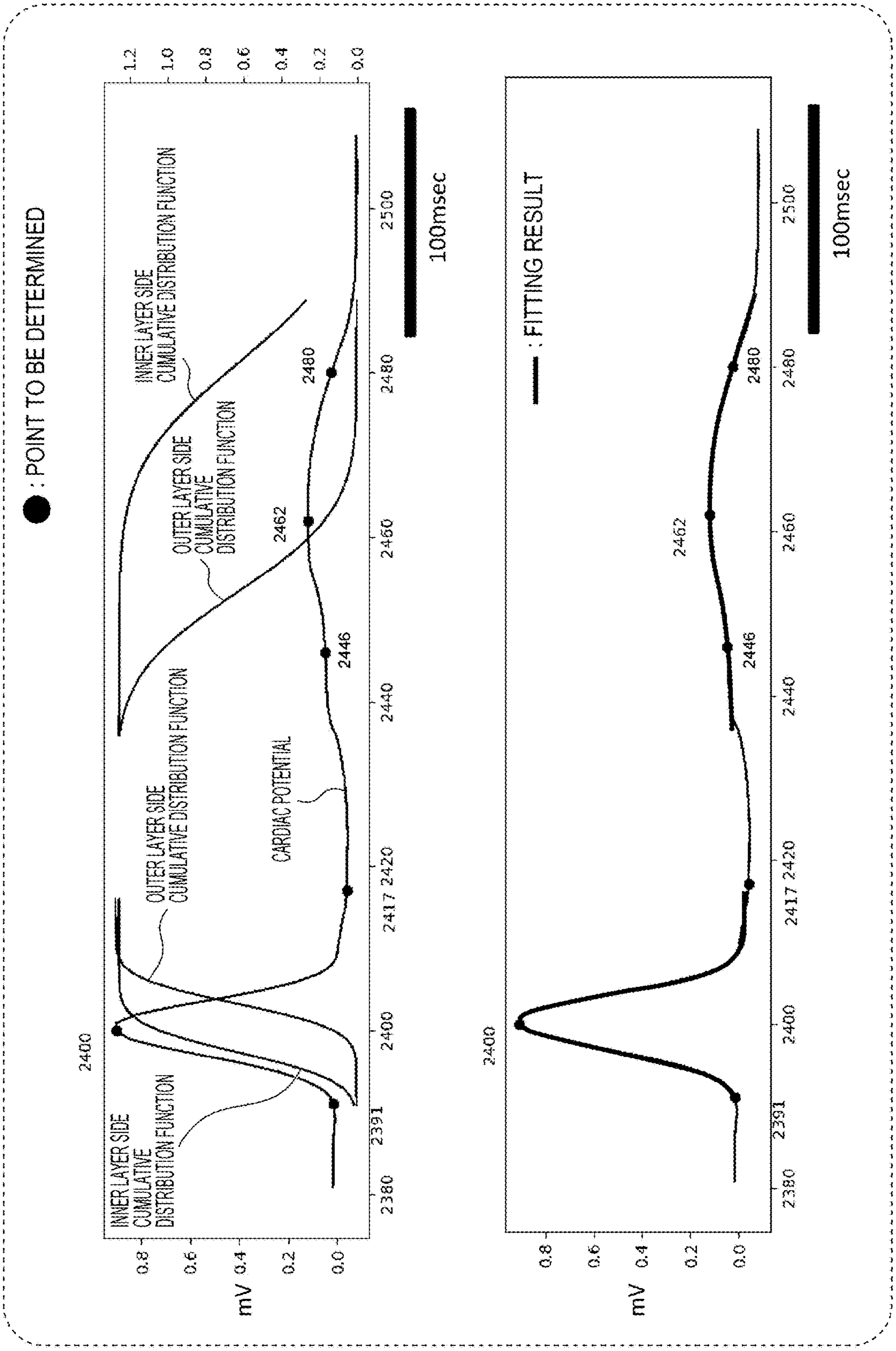
FIG. 44 is a diagram illustrating a twenty-fourth example in which an electrocardiogram is analyzed by the signal analysis device 1 in the first embodiment.
Figure 45:
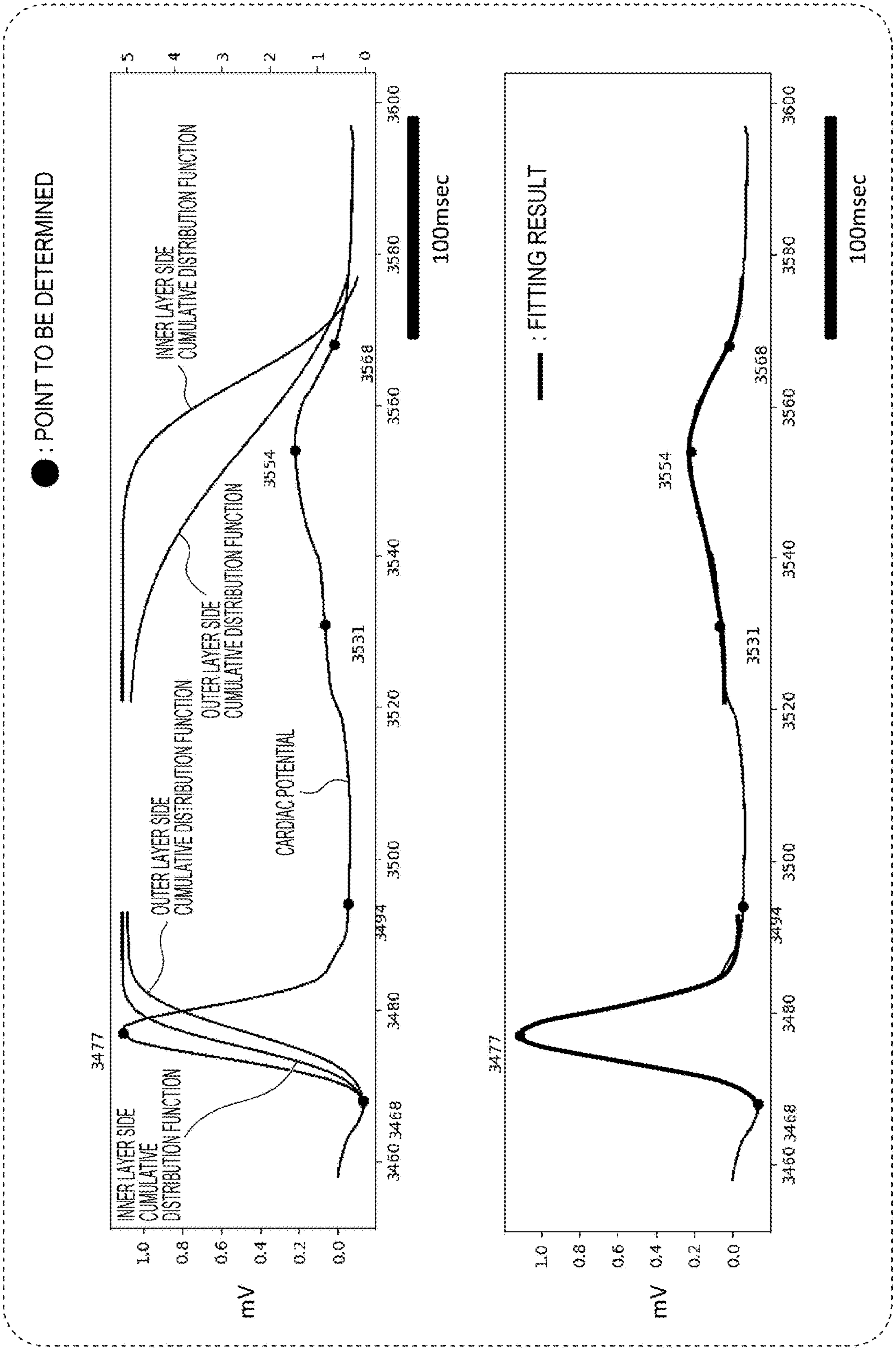
FIG. 45 is a diagram illustrating a twenty-fifth example in which an electrocardiogram is analyzed by the signal analysis device 1 in the first embodiment.
Figure 46:
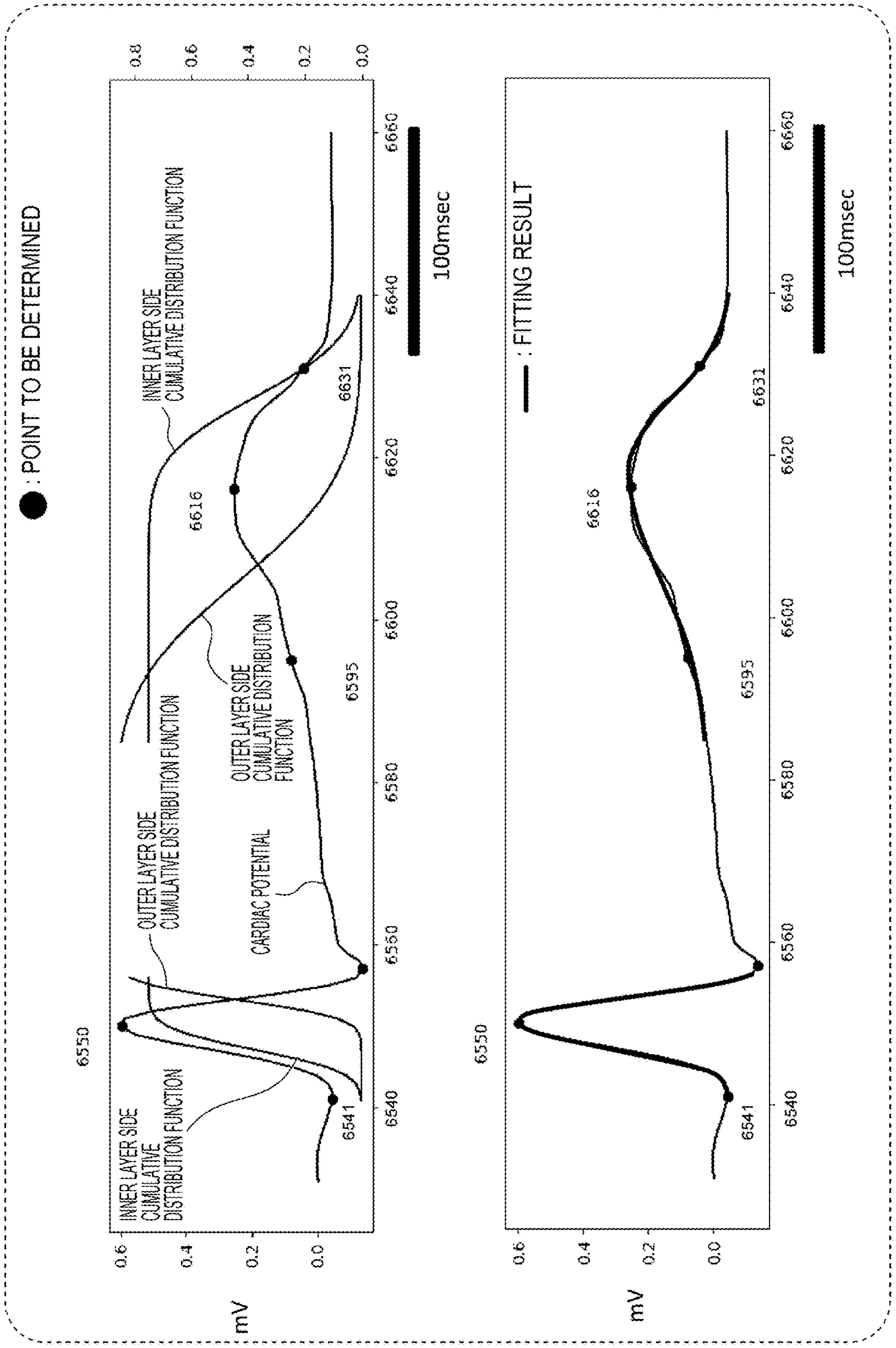
FIG. 46 is a diagram illustrating a twenty-sixth example in which an electrocardiogram is analyzed by the signal analysis device 1 in the first embodiment.
Figure 47:
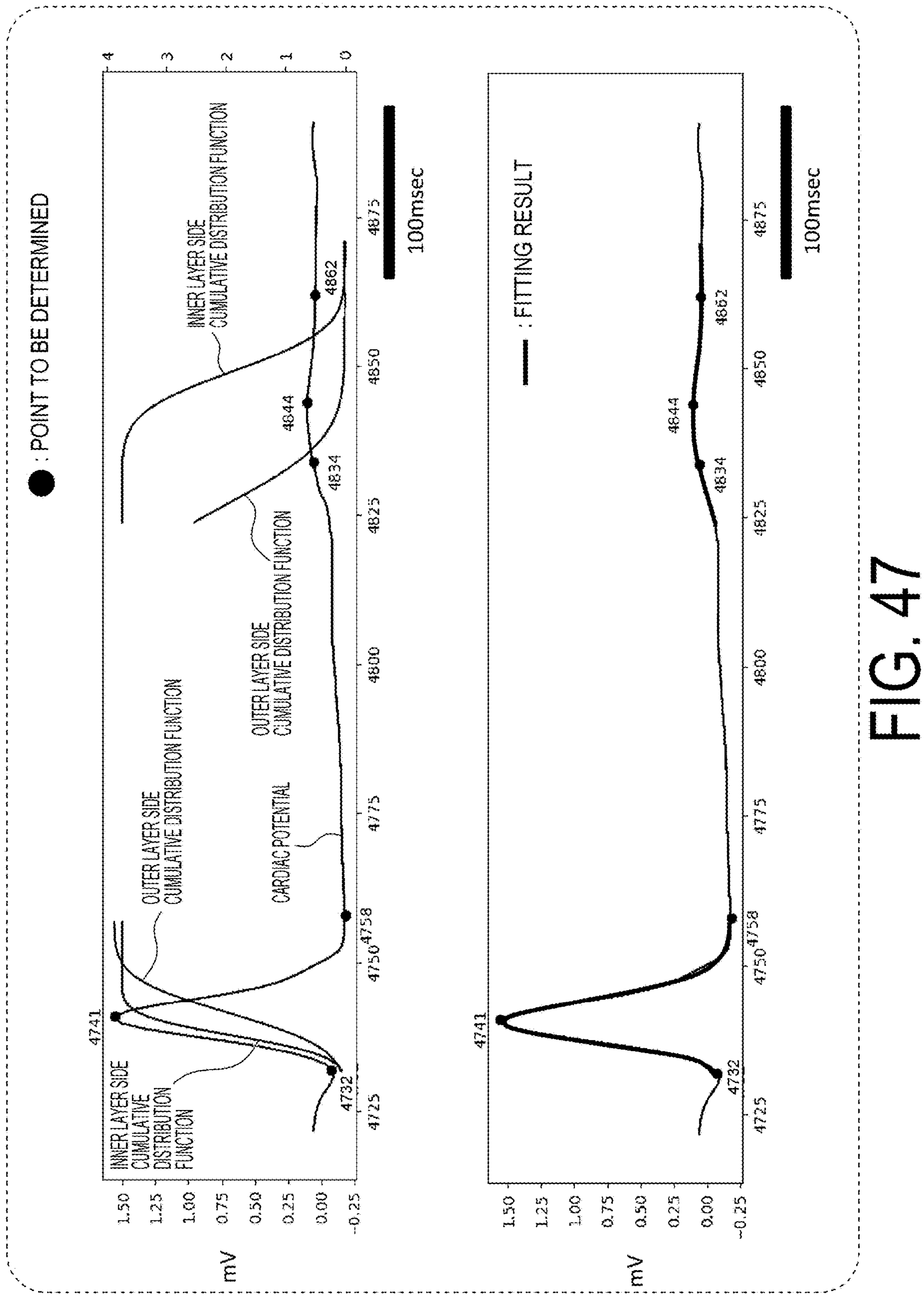
FIG. 47 is a diagram illustrating a twenty-seventh example in which an electrocardiogram is analyzed by the signal analysis device 1 in the first embodiment.
Figure 48:
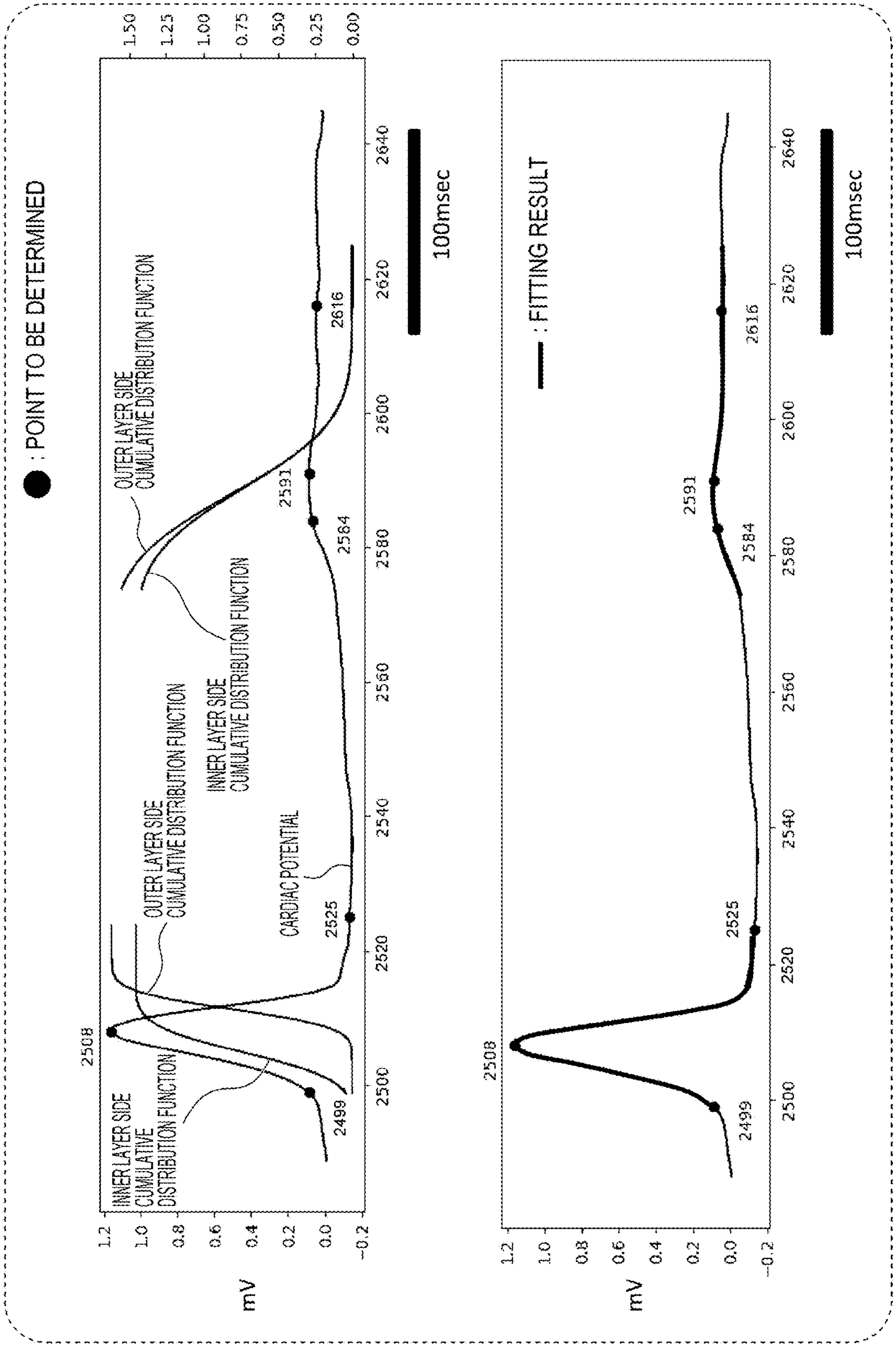
FIG. 48 is a diagram illustrating a twenty-eighth example in which an electrocardiogram is analyzed by the signal analysis device 1 in the first embodiment.
Figure 49:
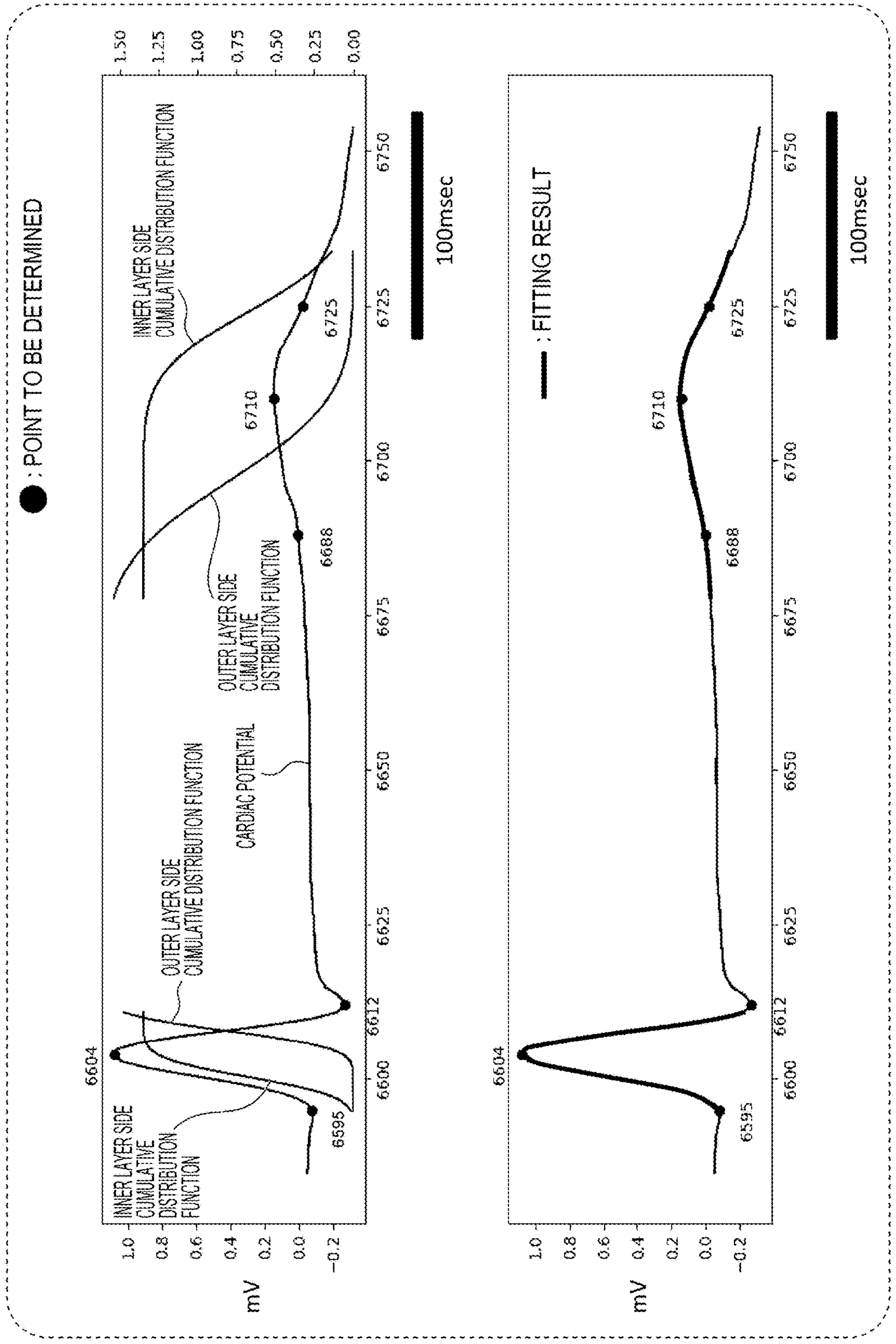
FIG. 49 is a diagram illustrating a twenty-ninth example in which an electrocardiogram is analyzed by the signal analysis device 1 in the first embodiment.
Figure 50:
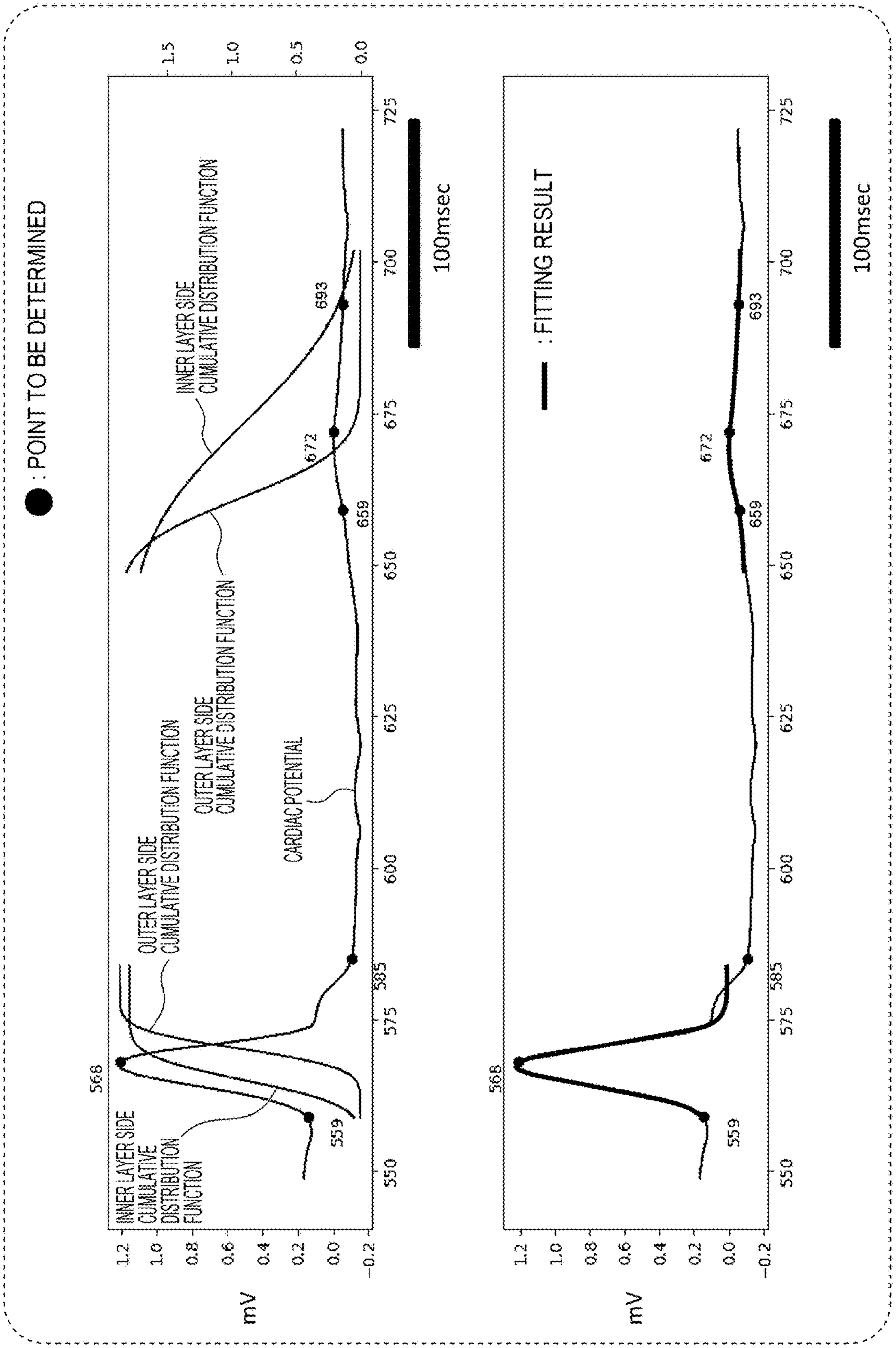
FIG. 50 is a diagram illustrating a thirtieth example in which an electrocardiogram is analyzed by the signal analysis device 1 in the first embodiment.
Figure 51:
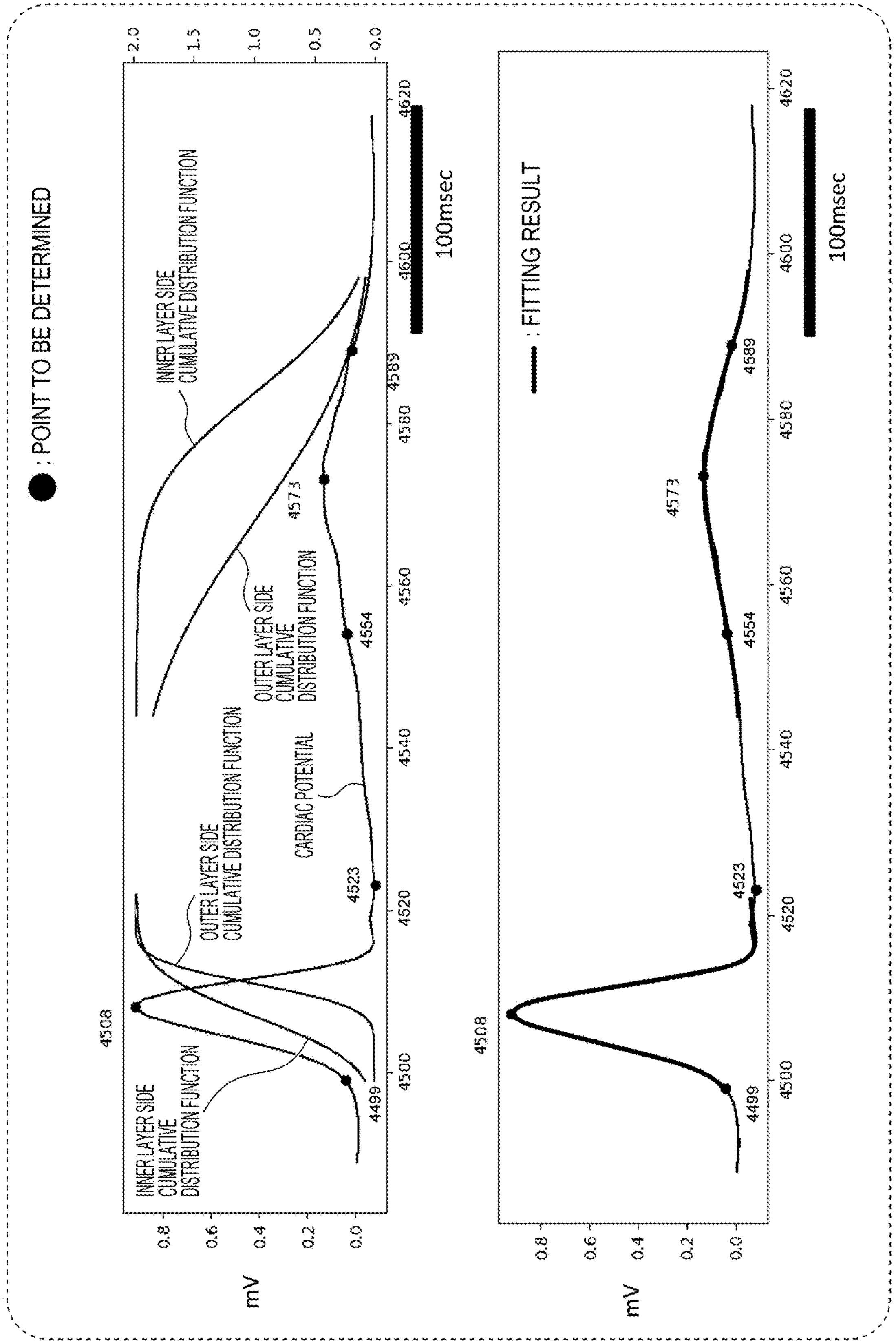
FIG. 51 is a diagram illustrating a thirty-first example in which an electrocardiogram is analyzed by the signal analysis device 1 in the first embodiment.
Figure 52:
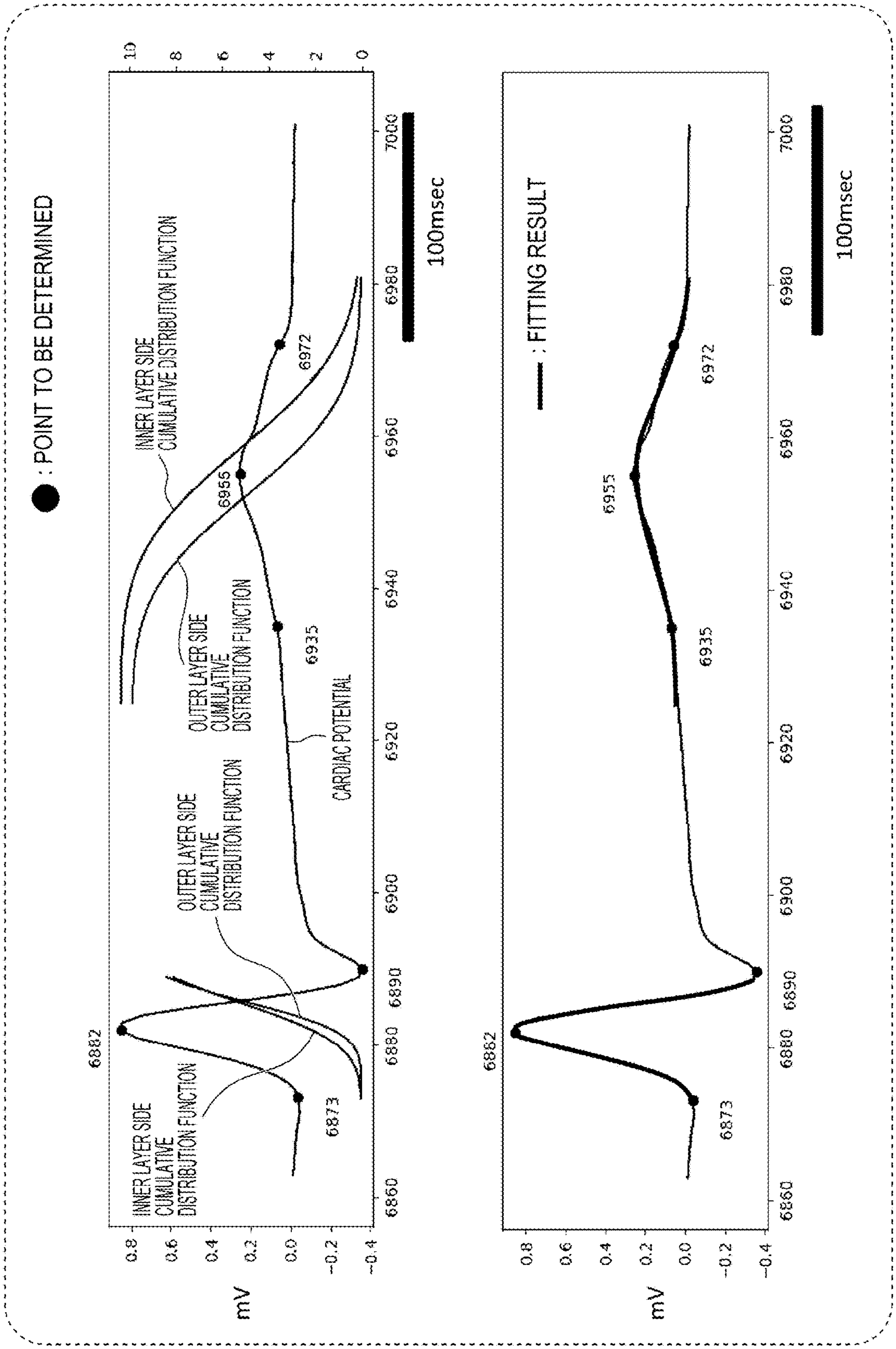
FIG. 52 is a diagram illustrating a thirty-second example in which an electrocardiogram is analyzed by the signal analysis device 1 in the first embodiment.
Figure 53:
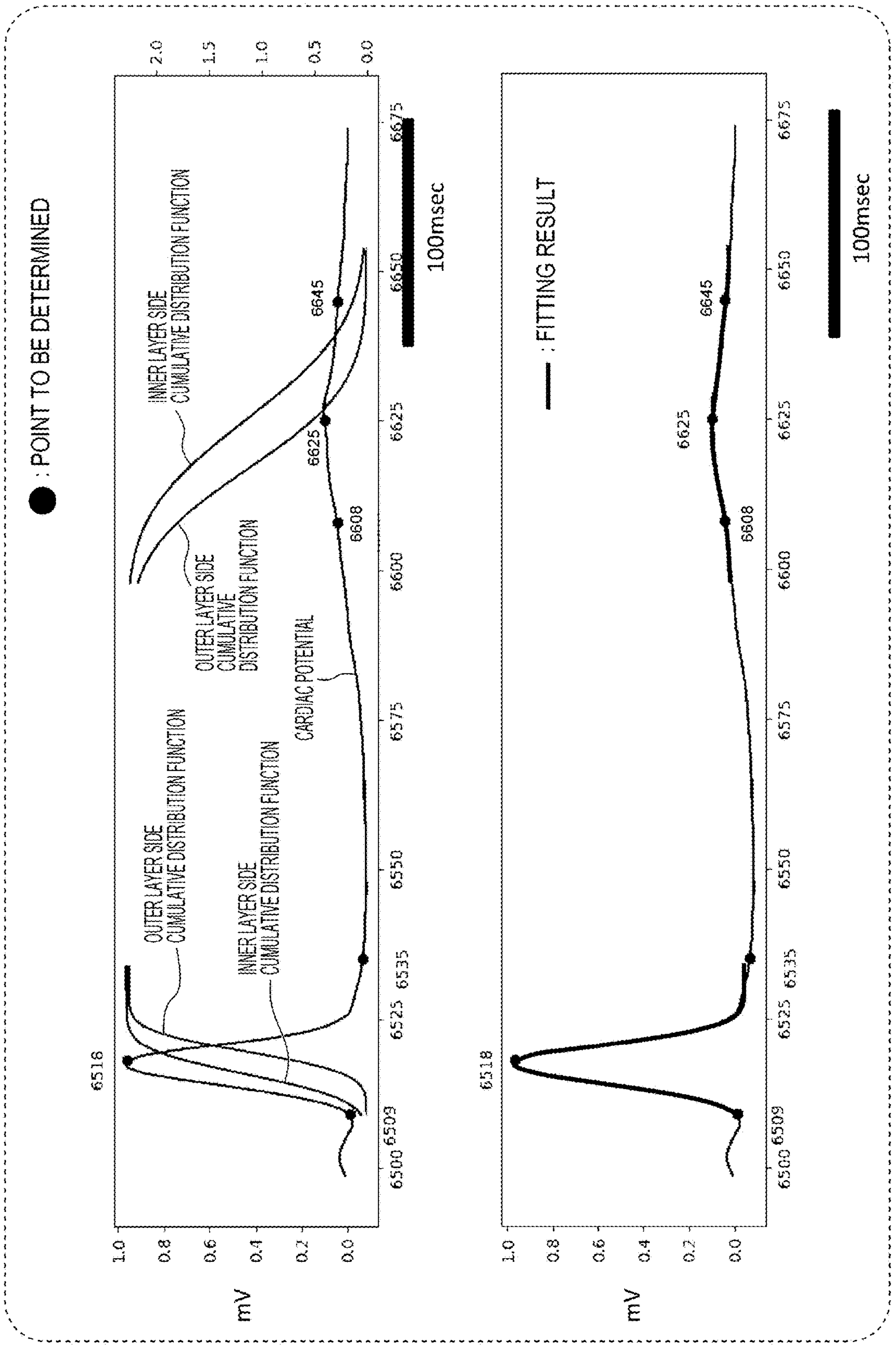
FIG. 53 is a diagram illustrating a thirty-third example in which an electrocardiogram is analyzed by the signal analysis device 1 in the first embodiment.
Figure 54:
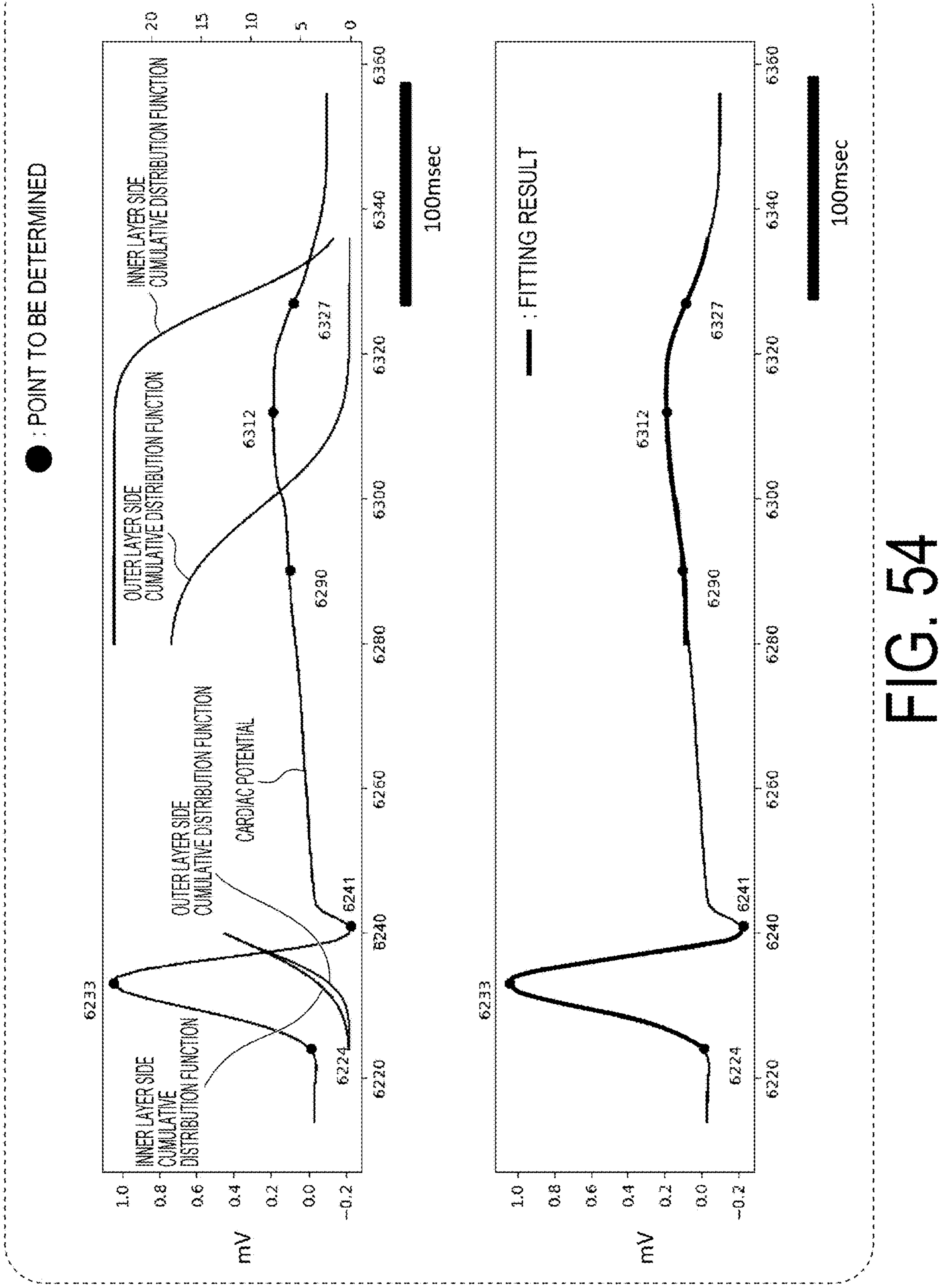
FIG. 54 is a diagram illustrating a thirty-fourth example in which an electrocardiogram is analyzed by the signal analysis device 1 in the first embodiment.
Figure 55:
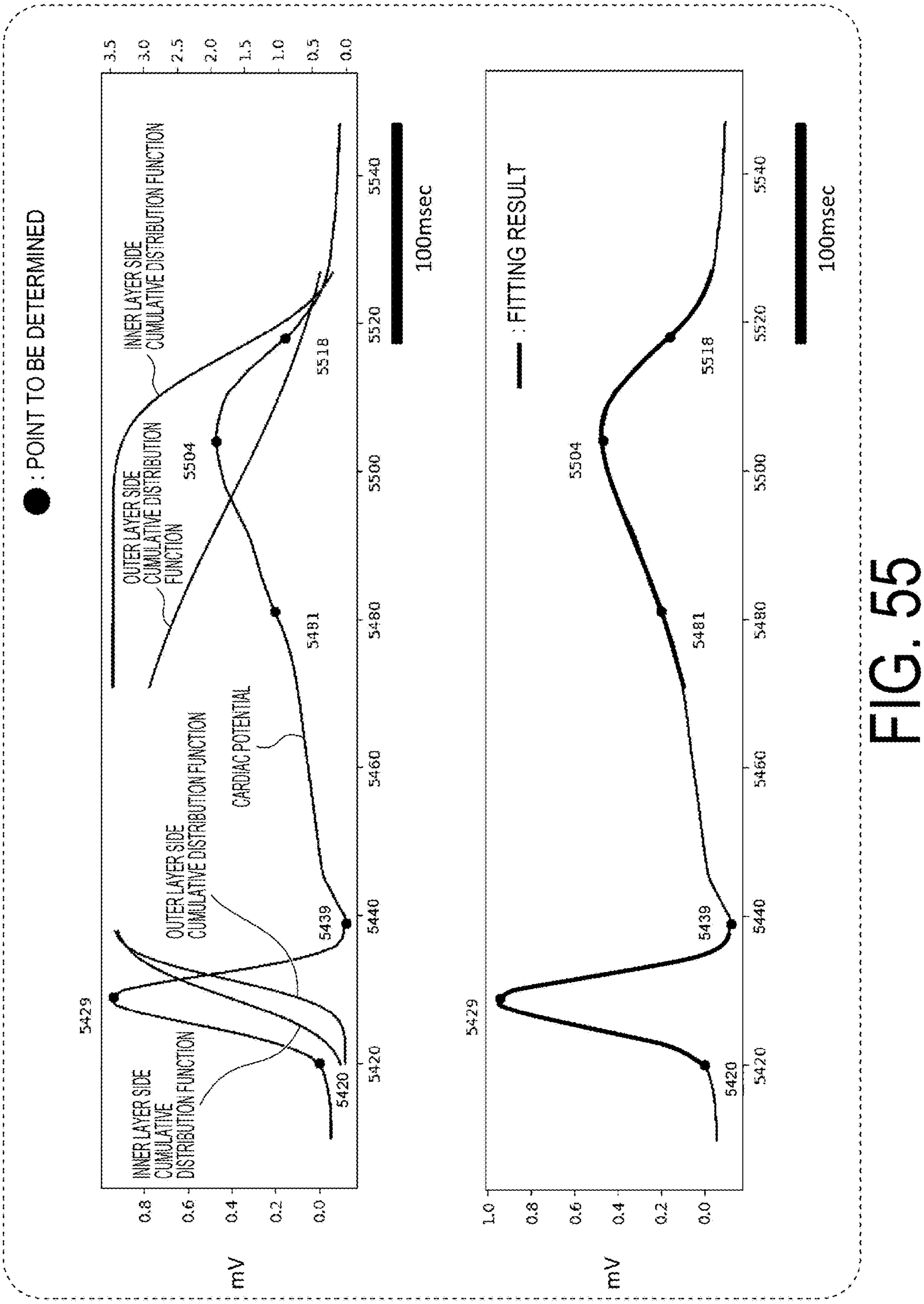
FIG. 55 is a diagram illustrating a thirty-fifth example in which an electrocardiogram is analyzed by the signal analysis device 1 in the first embodiment.
Figure 56:
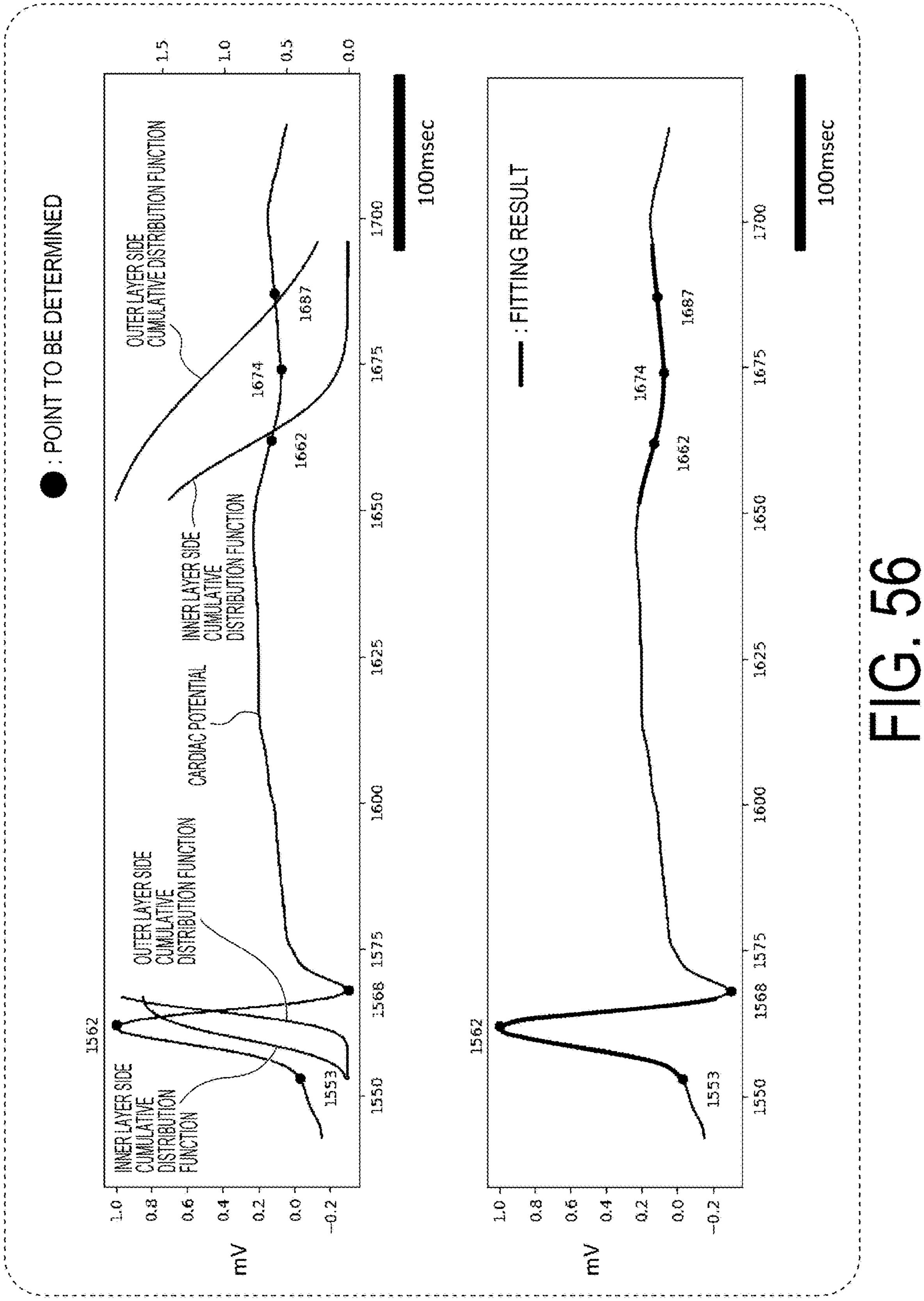
FIG. 56 is a diagram illustrating a thirty-sixth example in which an electrocardiogram is analyzed by the signal analysis device 1 in the first embodiment.
Figure 57:
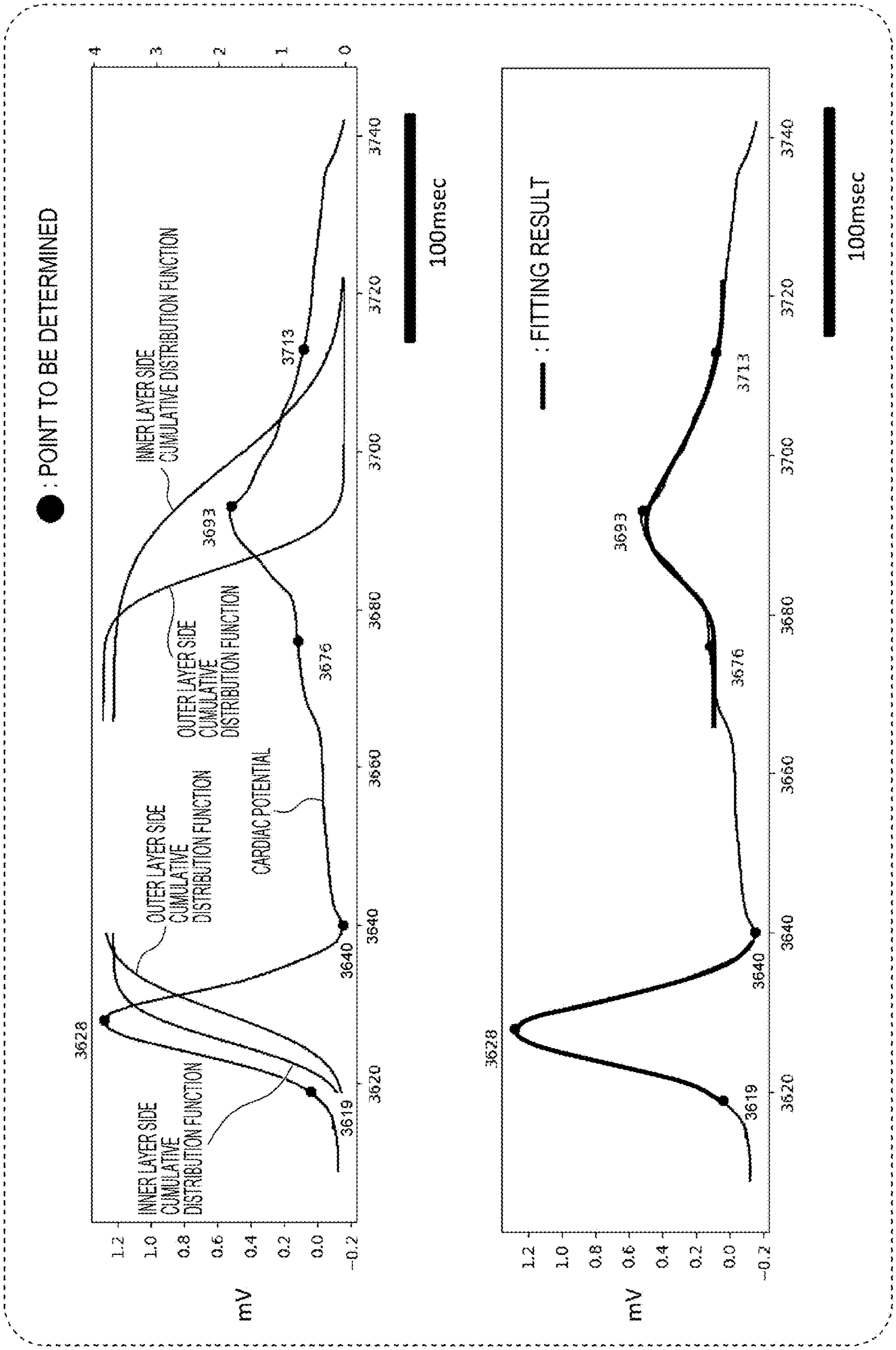
FIG. 57 is a diagram illustrating a thirty-seventh example in which an electrocardiogram is analyzed by the signal analysis device 1 in the first embodiment.
Figure 58:
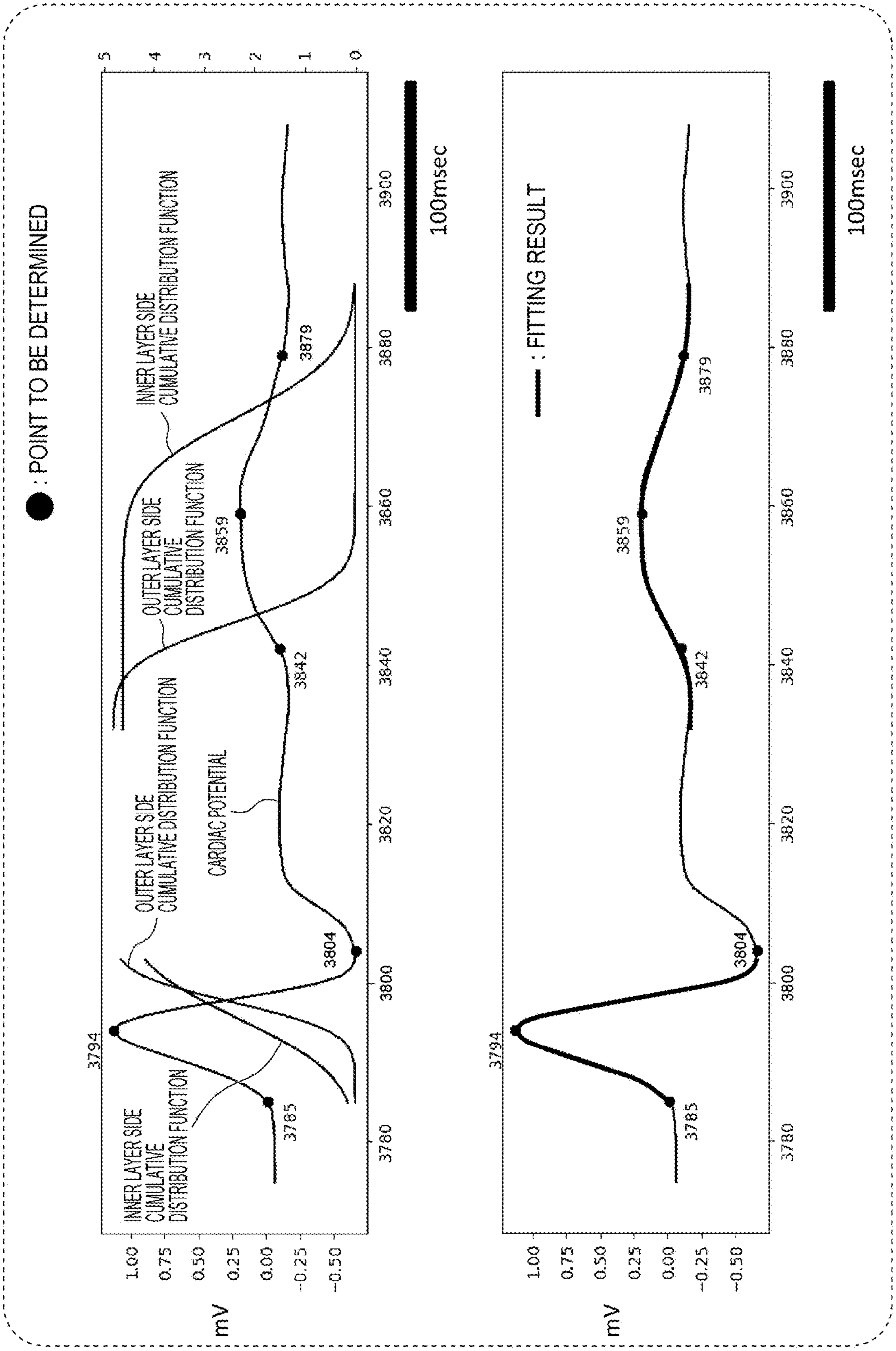
FIG. 58 is a diagram illustrating a thirty-eighth example in which an electrocardiogram is analyzed by the signal analysis device 1 in the first embodiment.
Figure 59:
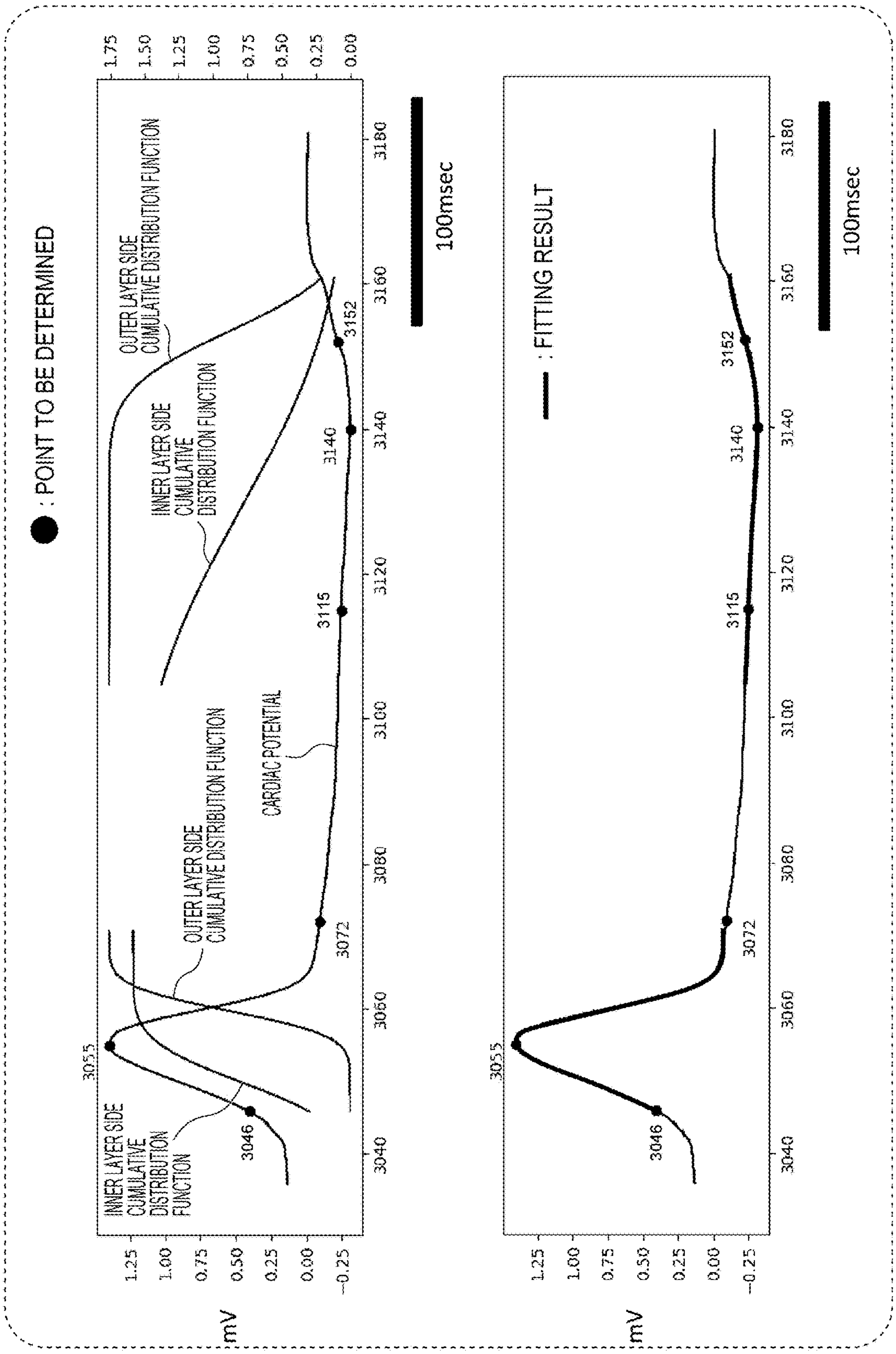
FIG. 59 is a diagram illustrating a thirty-ninth example in which an electrocardiogram is analyzed by the signal analysis device 1 in the first embodiment.

With reference to FIGS. 18 to 20, it will be described that information representing activity of a myocardium can be acquired from only an electrocardiogram by the signal analysis device 1 also for an electrocardiogram of a target heart in a depolarization period of Brugada syndrome type 1. In FIGS. 18 to 20, the vertical axis represents a potential in millivolts.

FIG. 18 is a first explanatory diagram for describing an example in which an electrocardiogram of a target heart in a depolarization period of Brugada syndrome type 1 is analyzed by the signal analysis device 1 in the first embodiment. FIG. 19 is a second explanatory diagram for the example in which the electrocardiogram of the target heart in the depolarization period of Brugada syndrome type 1 is analyzed by the signal analysis device 1 in the first embodiment. FIG. 20 is a third explanatory diagram for the example in which the electrocardiogram of the target heart in the depolarization period of Brugada syndrome type 1 is analyzed by the signal analysis device 1 in the first embodiment.

More specifically, FIG. 18 illustrates the electrocardiogram of chest second lead of Brugada syndrome. In FIG. 18, an inner frame W1 indicates a depolarization phase, and an inner frame W2 indicates a repolarization phase. The same applies to FIG. 19. That is, also in FIG. 19, the inner frame W1 represents the depolarization phase, and the inner frame W2 represents the repolarization phase.

More specifically, FIG. 19 illustrates the inner layer side cumulative distribution function and the outer layer side cumulative distribution function in the depolarization and the repolarization phase analyzed by the signal analysis device 1. In the example illustrated in FIG. 19, the repolarization phase of the inner layer side cumulative distribution function starts following the depolarization phase, indicating characteristics of early repolarization. On the other hand, in the example of FIG. 19, as for a potential amplitude of the outer layer side cumulative distribution function, a difference is observed between the depolarization phase and the repolarization phase. Furthermore, FIG. 19 illustrates a gap and anisotropy between the depolarization phase and the repolarization phase of the outer layer side cumulative distribution function. As described above, the signal analysis device 1 can express the early repolarization and the anisotropy between the depolarization and the repolarization that are characteristics of the waveform indicated by the electrocardiogram of the target heart of Brugada syndrome by averages and standard deviations of the depolarization phase and the repolarization phase of the inner layer side cumulative distribution function and the outer layer side cumulative distribution function, and a ratio of weight given to the outer layer side cumulative distribution function to weight given to the inner layer side cumulative distribution function (inner/outer layer ratio).

FIG. 20 is a comparison between an analysis result and an actual measurement value. More specifically, FIG. 20 illustrates a difference between the inner layer side cumulative distribution function and the outer layer side cumulative distribution function in the depolarization phase and the repolarization phase in FIG. 19. FIG. 20 also illustrates the actual measurement value of the electrocardiogram. Except for the tail end, the analysis result and the actual measurement value substantially correspond to each other. The tail end means a potential at a later time.

Note that, in FIGS. 18 to 20, an average $\mu$ of the inner layer side cumulative distribution function in the depolarization phase is 15, and a standard deviation $\sigma$ is 0.15. Furthermore, in FIGS. 18 to 20, an average $\mu$ of the outer layer side cumulative distribution function in the depolarization phase is 14, and a standard deviation $\sigma$ is 0.25. In FIGS. 18 to 20, an inner/outer layer ratio of the depolarization phase is 0.45. Furthermore, in FIGS. 18 to 20, an average $\mu$ of the inner layer side cumulative distribution function in the repolarization phase is 25, and a standard deviation $\sigma$ is 0.25. Furthermore, in FIGS. 18 to 20, an average $\mu$ of the outer layer side cumulative distribution function in the repolarization phase is 20, and a standard deviation $\sigma$ is 0.5.

FIGS. 21 to 59 illustrate results of analysis performed by the signal analysis device 1 using a public library of electrocardiogram data <https://physionet.org/about/database/>. FIGS. 21 to 59 illustrate an inner layer side cumulative distribution function, an outer layer side cumulative distribution function, and a fitting result obtained as a result of performing analysis on a cardiac potential by the signal analysis device 1.

Each of FIGS. 21 to 59 is a diagram illustrating an example in which an electrocardiogram is analyzed by the signal analysis device 1 in the first embodiment. Points to be determined illustrated in each diagram represent a Q point, an R point, an S point, a T start point, and a T end point of a cardiac potential in order from the left of the diagram. The points to be determined were determined by an inflection point detection and peak detection algorithm. Each diagram of FIGS. 21 to 59 illustrates the inner layer side cumulative distribution function and the outer layer side cumulative distribution function in each section obtained for the section of the depolarization phase (QRS wave) and the section of the repolarization phase (T wave). FIGS. 21 to 59 illustrate that, for various QRS waves and T waves, the signal analysis device 1 can express substantially the same shape by adjusting averages and standard deviations of the inner layer side cumulative distribution function and the outer layer side cumulative distribution function. Lower diagrams of FIGS. 21 to 59 illustrate original waveforms of electrocardiograms and fitting results. Note that each result in FIGS. 21 to 59 is a result of sampling at 300 Hz. For that reason, in the horizontal axis in each diagram of FIGS. 21 to 59, the origin represents 0 seconds and a value 1 represents 3.33 milliseconds.

The signal analysis device 1 formed as described above sets a waveform in the time section of the R wave or the T wave included in a waveform for one cycle of the cardiac cycle of the target heart as a target time waveform, and acquires, as parameters representing the characteristics of the target time waveform, a parameter specifying the first unimodal distribution or a parameter specifying the first cumulative distribution function, and a parameter specifying the second unimodal distribution or a parameter specifying the second cumulative distribution function when the target time waveform is approximated by an approximate time waveform that is a time waveform represented by a difference or a weighted difference between the first cumulative distribution function that is a cumulative distribution function of the first unimodal distribution and the second cumulative distribution function that is a cumulative distribution function of the second unimodal distribution. The first cumulative distribution function is information indicating activity of the myocardial inner layer of the target heart, and the second cumulative distribution function is information indicating activity of the myocardial outer layer of the target heart. Thus, a parameter representing a shape of the first cumulative distribution function is a parameter indicating the activity of the myocardial inner layer of the target heart (myocardial inner layer parameter), and a parameter representing a shape of the second cumulative distribution function is a parameter indicating the activity of the myocardial outer layer of the target heart (myocardial outer layer parameter). Information clearly indicating characteristics of the activity of the myocardial inner layer of the target heart and information clearly indicating characteristics of the activity of the myocardial outer layer of the target heart, such as these parameters, cannot be obtained by conventional analysis of the waveform of the electrocardiogram. Therefore, with the signal analysis device 1, useful information for grasping the state of the heart can be obtained from the waveform of the electrocardiogram.

[Acquisition of Only Some Parameters]

In a case where only the characteristics of the activity of the myocardial inner layer of the target heart are desired to be grasped, only the myocardial inner layer parameter may be acquired by the signal analysis device 1, and in a case where only the characteristics of the activity of the myocardial outer layer of the target heart are desired to be grasped, only the myocardial outer layer parameter may be acquired by the signal analysis device 1. Furthermore, only some parameters of the parameters representing the shape of the cumulative distribution function may be acquired by the signal analysis device 1 as the myocardial inner layer parameter or the myocardial outer layer parameter.

For example, the myocardial activity information parameter acquisition unit 132 of the analysis unit 130 of the signal analysis device 1 acquires, as a myocardial activity parameter that is a parameter indicating the activity of the myocardium of the target heart, at least one of, at least some of parameters specifying the first unimodal distribution, at least some of parameters specifying the first cumulative distribution function, at least some of parameters specifying the second unimodal distribution, or at least some of parameters specifying the second cumulative distribution function when the first target time waveform that is the waveform in the time section of the R wave of the target heart is approximated by a first approximate time waveform that is a time waveform represented by a difference or a weighted difference between the first cumulative distribution function that is a cumulative distribution function of the first unimodal distribution and the second cumulative distribution function that is a cumulative distribution function of the second unimodal distribution, or by a first approximate time waveform that is a time waveform represented by addition of a level value and the difference or the weighted difference between the first cumulative distribution function that is a cumulative distribution function of the first unimodal distribution and the second cumulative distribution function that is a cumulative distribution function of the second unimodal distribution.

For example, in a case where both the first unimodal distribution and the second unimodal distribution are Gaussian distributions, the myocardial activity information parameter acquisition unit 132 only needs to acquire, as a myocardial activity parameter, at least one of an average value of the first unimodal distribution, a standard deviation or variance of the first unimodal distribution, an average value of the second unimodal distribution, or a standard deviation or variance of the second unimodal distribution. Note that an average value of a Gaussian distribution is time at which the frequency value is the maximum value in a unimodal distribution, and is time at which the slope of a cumulative distribution function of the unimodal distribution is the maximum. Thus, for example, regardless of whether the first unimodal distribution and the second unimodal distribution are Gaussian distributions, the myocardial activity information parameter acquisition unit 132 only needs to acquire, as a myocardial activity parameter, at least one of time corresponding to the maximum value of the first unimodal distribution, time corresponding to the maximum slope of the first cumulative distribution function, time corresponding to the maximum value of the second unimodal distribution, or time corresponding to the maximum slope of the second cumulative distribution function.

For example, the myocardial activity information parameter acquisition unit 132 of the analysis unit 130 of the signal analysis device 1 acquires, as a myocardial activity parameter that is a parameter indicating the activity of the myocardium of the target heart, at least one of, at least some of parameters specifying the third unimodal distribution, at least some of parameters specifying the third cumulative distribution function, at least some of parameters specifying the fourth unimodal distribution, or at least some of parameters specifying the fourth cumulative distribution function when the second target inverse time waveform that is a waveform obtained by inverting the time axis of the second target time waveform that is a waveform in the time section of the T wave of the target heart is approximated by a second approximate inverse time waveform that is a waveform represented by a difference or a weighted difference between the third cumulative distribution function that is a cumulative distribution function of the third unimodal distribution and the fourth cumulative distribution function that is a cumulative distribution function of the fourth unimodal distribution, or by a second approximate inverse time waveform that is a waveform represented by addition of a level value and the difference or the weighted difference between the third cumulative distribution function that is a cumulative distribution function of the third unimodal distribution and the fourth cumulative distribution function that is a cumulative distribution function of the fourth unimodal distribution.

For example, in a case where both the third unimodal distribution and the fourth unimodal distribution are Gaussian distributions, the myocardial activity information parameter acquisition unit 132 only needs to acquire, as a myocardial activity parameter, at least one of an average value of the third unimodal distribution, a standard deviation or variance of the third unimodal distribution, an average value of the fourth unimodal distribution, or a standard deviation or variance of the fourth unimodal distribution. Furthermore, for example, regardless of whether the third unimodal distribution and the fourth unimodal distribution are Gaussian distributions, the myocardial activity information parameter acquisition unit 132 only needs to acquire, as a myocardial activity parameter, at least one of time corresponding to the maximum value of the distribution of the third unimodal distribution, time corresponding to the maximum slope of the third cumulative distribution function, time corresponding to the maximum value of the fourth unimodal distribution, or time corresponding to the maximum slope of the fourth cumulative distribution function. Note that, in a case where time is acquired as a myocardial activity parameter, the myocardial activity information parameter acquisition unit 132 acquires time (value of x in the above-described examples) instead of information representing time in the reverse direction (value of x' in the above-described examples) even in a case where approximation is performed for the waveform obtained by inverting the time axis.

For example, the myocardial activity information parameter acquisition unit 132 of the analysis unit 130 of the signal analysis device 1 sets a cumulative distribution function of the third unimodal distribution as the third cumulative distribution function, sets a cumulative distribution function of the fourth unimodal distribution as the fourth cumulative distribution function, sets a function obtained by subtracting the third cumulative distribution function from 1 as the third inverse cumulative distribution function, and sets a function obtained by subtracting the fourth cumulative distribution function from 1 as the fourth inverse cumulative distribution function, and acquires, as a myocardial activity parameter that is a parameter indicating the activity of the myocardium of the target heart, at least one of, at least some of parameters specifying the third unimodal distribution, at least some of parameters specifying the third cumulative distribution function, at least some of parameters specifying the fourth unimodal distribution, or at least some of parameters specifying the fourth cumulative distribution function when the second target time waveform that is a waveform in the time section of the T wave of the target heart is approximated by a second approximate time waveform that is a waveform obtained by a difference or a weighted difference between the third inverse cumulative distribution function and the fourth inverse cumulative distribution function, or by a second approximate time waveform that is a waveform represented by addition of a level value and the difference or the weighted difference between the third inverse cumulative distribution function and the fourth inverse cumulative distribution function.

For example, in a case where both the third unimodal distribution and the fourth unimodal distribution are Gaussian distributions, the myocardial activity information parameter acquisition unit 132 only needs to acquire, as a myocardial activity parameter, at least one of an average value of the third unimodal distribution, a standard deviation or variance of the third unimodal distribution, an average value of the fourth unimodal distribution, or a standard deviation or variance of the fourth unimodal distribution. Furthermore, for example, regardless of whether the third unimodal distribution and the fourth unimodal distribution are Gaussian distributions, the myocardial activity information parameter acquisition unit 132 only needs to acquire, as a myocardial activity parameter, at least one of the time corresponding to the maximum value of the third unimodal distribution, the time corresponding to the maximum slope of the third cumulative distribution function, the time corresponding to the maximum value of the fourth unimodal distribution, or the time corresponding to the maximum slope of the fourth cumulative distribution function.

Similarly, for example, in a case where the myocardial activity information parameter acquisition unit 132 of the analysis unit 130 of the signal analysis device 1 further approximates a residual time waveform that is a time waveform of a difference between the first target time waveform and the first approximate time waveform, or a residual time waveform that is a time waveform of a difference between the second target time waveform and the second approximate time waveform, or a residual time waveform that is a time waveform of a difference between the second target time waveform and a second approximate time waveform that is a waveform obtained by inverting the time axis of a second approximate inverse time waveform, by an approximate residual time waveform that is a time waveform represented by the fifth cumulative distribution function that is a cumulative distribution function of the fifth unimodal distribution or multiplication of the fifth cumulative distribution function by weight, at least one of, at least some of parameters specifying the fifth unimodal distribution, or at least some of parameters specifying the fifth cumulative distribution function is also acquired as a myocardial activity parameter that is a parameter indicating the activity of the myocardium of the target heart.

For example, in a case where the fifth unimodal distribution is a Gaussian distribution, the myocardial activity information parameter acquisition unit 132 only needs to acquire, as a myocardial activity parameter, at least one of an average value of the fifth unimodal distribution, or a standard deviation or variance of the fifth unimodal distribution. Furthermore, for example, regardless of whether the fifth unimodal distribution is a Gaussian distribution, the myocardial activity information parameter acquisition unit 132 only needs to acquire, as a myocardial activity parameter, at least one of time corresponding to the maximum value of the fifth unimodal distribution or time corresponding to the maximum slope of the fifth cumulative distribution function.

Furthermore, for example, in a case where the myocardial activity information parameter acquisition unit 132 of the analysis unit 130 of the signal analysis device 1 further approximates the residual time waveform by an approximate residual time waveform that is a waveform represented by a difference or a weighted difference between the fifth cumulative distribution function that is a cumulative distribution function of the fifth unimodal distribution and the sixth cumulative distribution function that is a cumulative distribution function of the sixth unimodal distribution, at least one of, at least some of the parameters specifying the fifth unimodal distribution, at least some of the parameters specifying the fifth cumulative distribution function, at least some of parameters specifying the sixth unimodal distribution, or at least some of parameters specifying the sixth cumulative distribution function is acquired as a myocardial activity parameter that is a parameter indicating the activity of the myocardium of the target heart.

For example, in a case where both the fifth unimodal distribution and the sixth unimodal distribution are Gaussian distributions, the myocardial activity information parameter acquisition unit 132 only needs to acquire, as a myocardial activity parameter, at least one of the average value of the fifth unimodal distribution, the standard deviation or variance of the fifth unimodal distribution, an average value of the sixth unimodal distribution, or a standard deviation or variance of the sixth unimodal distribution. Furthermore, for example, regardless of whether the fifth unimodal distribution and the sixth unimodal distribution are Gaussian distributions, the myocardial activity information parameter acquisition unit 132 only needs to acquire, as a myocardial activity parameter, at least one of the time corresponding to the maximum value of the fifth unimodal distribution, the time corresponding to the maximum slope of the fifth cumulative distribution function, time corresponding to the maximum value of the sixth unimodal distribution, or time corresponding to the maximum slope of the sixth cumulative distribution function.

[Acquisition of Myocardial Activity Parameter by Arithmetic Operation of Parameters Obtained by Fitting]

Characteristics of the activity of the myocardium of the target heart may clearly appear not only in the parameters obtained by the fitting described above but also in a value obtained by an arithmetic operation of the parameters obtained by the fitting. Thus, the value obtained by the arithmetic operation of the parameters obtained by the fitting may be acquired by the signal analysis device 1 as a myocardial activity parameter. The parameter obtained by the fitting is at least one of a parameter specifying a unimodal distribution or a parameter specifying a cumulative distribution function, weight, or a level value. The parameter specifying the unimodal distribution or the parameter specifying the cumulative distribution function is at least one of an average or a standard deviation (or variance) in a case where the unimodal distribution is a Gaussian distribution. Regardless of whether the unimodal distribution is a Gaussian distribution, time corresponding to the maximum value of the unimodal distribution is an example of the parameter specifying the unimodal distribution, and time corresponding to the maximum slope of the cumulative distribution function of the unimodal distribution is an example of the parameter specifying the cumulative distribution function.

For example, the myocardial activity information parameter acquisition unit 132 of the analysis unit 130 of the signal analysis device 1 may acquire a parameter indicating the activity of the myocardium of the target heart (parameter different from each parameter described above) by an arithmetic operation of the myocardial activity parameter obtained by the fitting described above for the waveform in the time section of the R wave included in the waveform for one cycle indicating the cardiac cycle of the target heart (that is, the parameter indicating the activity of the myocardium of the target heart in the time section of the R wave) and the myocardial activity parameter obtained by the fitting described above for the waveform in the time section of the T wave included in the waveform for the one cycle (that is, the parameter indicating the activity of the myocardium of the target heart in the time section of the T wave).

Furthermore, for example, the myocardial activity information parameter acquisition unit 132 of the analysis unit 130 of the signal analysis device 1 may acquire a parameter indicating the activity of the myocardium of the target heart (parameter different from each parameter described above) by an arithmetic operation of the parameter indicating the activity of the myocardial inner layer of the target heart obtained by the fitting described above for the waveform in the time section of the R wave included in the waveform for one cycle indicating the cardiac cycle of the target heart and the parameter indicating the activity of the myocardial outer layer of the target heart obtained by the fitting.

Furthermore, for example, the myocardial activity information parameter acquisition unit 132 of the analysis unit 130 of the signal analysis device 1 may acquire a parameter indicating the activity of the myocardium of the target heart (parameter different from each parameter described above) by an arithmetic operation of the parameter indicating the activity of the myocardial inner layer of the target heart obtained by the fitting described above for the waveform in the time section of the T wave included in the waveform for one cycle indicating the cardiac cycle of the target heart and the parameter indicating the activity of the myocardial outer layer of the target heart obtained by the fitting.

Hereinafter, examples will be described in which, in a case where all of the first to fourth unimodal distributions are Gaussian distributions, values obtained by an arithmetic operation of averages obtained by fitting are used as myocardial activity parameters. In a case where the first to fourth unimodal distributions are not Gaussian distributions, "average" in the following examples only needs to be read as "time at which the value is maximum in the unimodal distribution", that is, "time corresponding to the maximum value of the unimodal distribution", "time at which the slope is maximum in the cumulative distribution function", that is, "time corresponding to the maximum slope of the cumulative distribution function", or the like.

(1) Parameter Representing Time from Depolarization to Switching to Repolarization It is known that sudden death may occur due to arrhythmia in a case where time from depolarization of the inner layer or the outer layer of the myocardium to switching to repolarization of the inner layer or the outer layer of the myocardium is extremely short or extremely long. That is, shortening or prolongation of the time from depolarization of the myocardium to switching to repolarization may indicate that some pathological state may have occurred in the myocardium. Thus, the signal analysis device 1 preferably acquires the time from depolarization of the inner layer or the outer layer of the myocardium to switching to repolarization of the inner layer or the outer layer of the myocardium as a myocardial activity parameter, and specifically, preferably acquires at least one of the following four parameters (1A) to (1D) as a myocardial activity parameter.

(1A) Parameter Representing Time from Depolarization of Inner Layer of Myocardium to Switching to Repolarization of Inner Layer of Myocardium The myocardial activity information parameter acquisition unit 132 of the analysis unit 130 of the signal analysis device 1 may acquire, as a myocardial activity parameter, a difference between the average of the first unimodal distribution obtained by the fitting described above for the first target time waveform that is the waveform in the time section of the R wave included in the waveform for one cycle indicating the cardiac cycle of the target heart and the average of the third unimodal distribution obtained by the fitting described above for the second target time waveform that is the waveform in the time section of the T wave included in the waveform for the one cycle. For example, when the average of the first unimodal distribution is $\mu_a$ and the average of the third unimodal distribution is $\mu_c$ as in the example described above, the myocardial activity information parameter acquisition unit 132 may acquire $|\mu_a-\mu_c|$ as a myocardial activity parameter. Note that, in consideration that $\mu_c$ is temporally later than a, the myocardial activity information parameter acquisition unit 132 may acquire $\mu_c-\mu_a$ as a myocardial activity parameter. This myocardial activity parameter is a parameter representing time from depolarization of the inner layer of the myocardium to switching to repolarization of the inner layer of the myocardium.

(1B) Parameter Representing Time from Depolarization of Outer Layer of Myocardium to Switching to Repolarization of Outer Layer of Myocardium The myocardial activity information parameter acquisition unit 132 of the analysis unit 130 of the signal analysis device 1 may acquire, as a myocardial activity parameter, a difference between the average of the second unimodal distribution obtained by the fitting described above for the first target time waveform that is the waveform in the time section of the R wave included in the waveform for one cycle indicating the cardiac cycle of the target heart and the average of the fourth unimodal distribution obtained by the fitting described above for the second target time waveform that is the waveform in the time section of the T wave included in the waveform for the one cycle. For example, when the average of the second unimodal distribution is $\mu_b$ and the average of the fourth unimodal distribution is $\mu_d$ as in the example described above, the myocardial activity information parameter acquisition unit 132 may acquire $|\mu_b-\mu_d|$ as a myocardial activity parameter. Note that, in consideration that $\mu_d$ is temporally later than pb, the myocardial activity information parameter acquisition unit 132 may acquire $\mu_d-\mu_b$ as a myocardial activity parameter. This myocardial activity parameter is a parameter representing time from depolarization of the outer layer of the myocardium to switching to repolarization of the outer layer of the myocardium.

(1C) Parameter Representing Time from Depolarization of Outer Layer of Myocardium to Switching to Repolarization of Inner Layer of Myocardium The myocardial activity information parameter acquisition unit 132 of the analysis unit 130 of the signal analysis device 1 may acquire, as a myocardial activity parameter, a difference between the average of the second unimodal distribution obtained by the fitting described above for the first target time waveform that is the waveform in the time section of the R wave included in the waveform for one cycle indicating the cardiac cycle of the target heart and the average of the third unimodal distribution obtained by the fitting described above for the second target time waveform that is the waveform in the time section of the T wave included in the waveform for the one cycle. For example, when the average of the second unimodal distribution is $\mu_b$ and the average of the third unimodal distribution is $\mu_c$ as in the example described above, the myocardial activity information parameter acquisition unit 132 may acquire $|\mu_b-\mu_c|$ as a myocardial activity parameter. Note that, in consideration that pc is temporally later than pb, the myocardial activity information parameter acquisition unit 132 may acquire $\mu_c-\mu_b$ as a myocardial activity parameter. This myocardial activity parameter is a parameter representing time from depolarization of the outer layer of the myocardium to switching to repolarization of the inner layer of the myocardium.

(1D) Parameter Representing Time from Depolarization of Inner Layer of Myocardium to Switching to Repolarization of Outer Layer of Myocardium The myocardial activity information parameter acquisition unit 132 of the analysis unit 130 of the signal analysis device 1 may acquire, as a myocardial activity parameter, a difference between the average of the first unimodal distribution obtained by the fitting described above for the first target time waveform that is the waveform in the time section of the R wave included in the waveform for one cycle indicating the cardiac cycle of the target heart and the average of the fourth unimodal distribution obtained by the fitting described above for the second target time waveform that is the waveform in the time section of the T wave included in the waveform for the one cycle. For example, when the average of the first unimodal distribution is $\mu_a$ and the average of the fourth unimodal distribution is $\mu_a$ as in the example described above, the myocardial activity information parameter acquisition unit 132 may acquire $|\mu_a-\mu_d|$ as a myocardial activity parameter. Note that, in consideration that $\mu_a$ is temporally later than $\mu_a$, the myocardial activity information parameter acquisition unit 132 may acquire $\mu_d-\mu_a$ as a myocardial activity parameter. This myocardial activity parameter is a parameter representing time from depolarization of the inner layer of the myocardium to switching to repolarization of the outer layer of the myocardium.

(2) Parameter Representing Time Difference and Order Between Inner Layer Activity and Outer Layer Activity in Depolarization In a case where a time difference between activity of the inner layer and activity of the outer layer in depolarization is longer than normal, there is a possibility that a disorder such as delay or block occurs in conduction of excitation of the myocardium, or a place where excitation starts or the order in which excitation is transmitted are different from a normal pattern, and in particular, it is suggested that there is a disorder in a stimulation conduction system of the myocardium, ischemic state of the myocardium, and premature contraction. Thus, the signal analysis device 1 preferably acquires, as a myocardial activity parameter, a parameter representing the time difference and order between the activity of the inner layer and the activity of the outer layer in depolarization. Specifically, the myocardial activity information parameter acquisition unit 132 of the analysis unit 130 of the signal analysis device 1 may acquire, as a myocardial activity parameter, a difference between the average of the first unimodal distribution and the average of the second unimodal distribution obtained by the fitting described above for the first target time waveform that is the waveform in the time section of the R wave included in the waveform for one cycle indicating the cardiac cycle of the target heart. For example, when the average of the first unimodal distribution is $\mu_a$ and the average of the second unimodal distribution is $\mu_b$ as in the example described above, the myocardial activity information parameter acquisition unit 132 may acquire $\mu_a-\mu_b$ or $\mu_b-\mu_a$ as a myocardial activity parameter.

(3) Parameter Representing Time Difference and Order Between Inner Layer Activity and Outer Layer Activity in Repolarization In a case where a time difference between activity of the inner layer and activity of the outer layer in repolarization is prolonged or shortened, some abnormality may have occurred in the myocardium. Thus, the signal analysis device 1 preferably acquires, as a myocardial activity parameter, a parameter representing the time difference and order between the activity of the inner layer and the activity of the outer layer in repolarization. Specifically, the myocardial activity information parameter acquisition unit 132 of the analysis unit 130 of the signal analysis device 1 may acquire, as a myocardial activity parameter, a difference between the average of the third unimodal distribution and the average of the fourth unimodal distribution obtained by the fitting described above for the second target time waveform that is the waveform in the time section of the T wave included in the waveform for one cycle indicating the cardiac cycle of the target heart. For example, when the average of the third unimodal distribution is $\mu_c$ and the average of the fourth unimodal distribution is $\mu_d$ as in the example described above, the myocardial activity information parameter acquisition unit 132 may acquire $\mu_c-\mu_d$ or $\mu_d-\mu_c$ as a myocardial activity parameter.

(Correction of Myocardial Activity Parameter)

Note that a myocardial activity parameter regarding the width in the time direction among the myocardial activity parameters described above acquired by the myocardial activity information parameter acquisition unit 132 is characterized in that influence of fluctuation due to the heart rate and influence of individual differences of age, gender, and the like are recognized, similarly to a parameter regarding the width in the time direction (for example, QT interval) among conventional parameters indicating activity of the heart. For the conventional parameter regarding the width in the time direction, it is known that correction for reducing the influence of fluctuation due to the heart rate and the influence of the individual differences is performed, and a corrected value is used as a parameter for evaluating the activity of the heart. Thus, the myocardial activity parameter acquired by the myocardial activity information parameter acquisition unit 132 may also be corrected for reducing the influence of fluctuation due to the heart rate and the influence of the individual differences, and a corrected value may be used as a parameter for evaluating the activity of the myocardium. For example, for the fluctuation due to the heart rate, the myocardial activity parameter acquired by the fitting described above may be corrected by a linear or nonlinear arithmetic operation on the basis of a time interval between an R spine and an R spine adjacent to each other (Hereinafter, the interval is referred to as an "RR interval"), and a corrected value may be used as a myocardial activity parameter. Furthermore, for the individual differences, a relationship between the RR interval and the myocardial activity parameter acquired by the fitting described above may be obtained from electrocardiogram data of each individual to perform correction, and a corrected value may be used as a myocardial activity parameter. This correction may be performed by another device after the signal analysis device 1 outputs the myocardial activity parameter acquired by the fitting, or may be performed by the signal analysis device 1. In a case where the signal analysis device 1 performs correction of the myocardial activity parameter, for example, the myocardial activity information parameter acquisition unit 132 only needs to perform correction on the myocardial activity parameter acquired by the fitting described above and output a corrected value as a myocardial activity parameter. Note that, in a case where the correction is performed in the signal analysis device 1, the myocardial activity parameter acquired by the fitting described above is an intermediate parameter acquired in the device as a result, but is still a parameter representing the activity of the myocardium as in a case of being output outside the device.

Modification

Note that the electrocardiogram is preferably an electrocardiogram of lead close to a cardiac electromotive force vector. The electrocardiogram of lead close to a cardiac electromotive force vector is preferably, for example, an electrocardiogram capable of acquiring three-dimensional information on a cardiac potential such as lead II, lead V4, and lead V5. Since an amount of information increases as the number of channels of the electrocardiogram increases, it is desirable that there is a larger number of channels of the electrocardiogram. That is, the signal analysis device 1 may perform analysis with a waveform of each of the channels of the multi-channel electrocardiogram as a target, and obtain a myocardial activity parameter that is an analysis result for each of the channels.

Note that the signal analysis device 1 may be implemented by using a plurality of information processing devices communicably connected to each other via a network. In this case, the functional units included in the signal analysis device 1 may be implemented in a distributed manner in the plurality of information processing devices.

Note that the electrocardiogram acquisition unit 110 is an example of a biological information acquisition unit.

Second Embodiment

In the first embodiment, the myocardial activity parameter is obtained as useful information for grasping the state of the heart from the time-series biological information regarding the pulsation of the heart; however, whether or not the heart is normal and what kind of disease corresponds to in a case where the heart is not normal may be obtained as useful information for grasping the state of the heart from the time-series biological information regarding the pulsation of the heart, and this mode will be described as a second embodiment.

As described in the background art, even if waveforms of electrocardiograms are similar to each other, manners of the onset of a disease related to the heart may be different from each other. That is, even if learning is performed for an estimation model for obtaining an estimation result such as whether or not the heart is normal and what kind of disease corresponds to in a case where the heart is not normal with time-series biological information regarding the pulsation as an input, and the estimation result is obtained by estimation using the learned estimation model, there is a possibility that the estimation accuracy cannot be increased.

On the other hand, with the signal analysis device 1 of the first embodiment, from the time-series biological information on one channel regarding the pulsation of the heart, it is possible to obtain information clearly indicating a characteristic of the activity of the myocardium as a myocardial activity parameter. Furthermore, as described in the first embodiment, the myocardial activity parameter obtained by the signal analysis device 1 of the first embodiment is strongly related to whether or not the heart is normal and what kind of disease corresponds to in a case where the heart is not normal. In consideration of these, if a myocardial activity parameter is acquired from time-series biological information regarding the pulsation of the heart by processing similar to that performed by the signal analysis device 1 of the first embodiment, and learning is performed for an estimation model for obtaining an estimation result such as whether or not the heart is normal and what kind of disease corresponds to in a case where the heart is not normal with the acquired myocardial activity parameter as an input, and an estimation result is obtained by estimation using the learned estimation model, it can be expected that a highly accurate estimation result is obtained. An information provision system of the second embodiment performs the learning and the estimation. The doctor uses the estimation result by the information provision system of the second embodiment as a reference at the time of diagnosis, whereby it is expected that whether or not the target heart is normal and what kind of disease corresponds to in a case where the target heart is not normal can be diagnosed more accurately.

Figure 60:
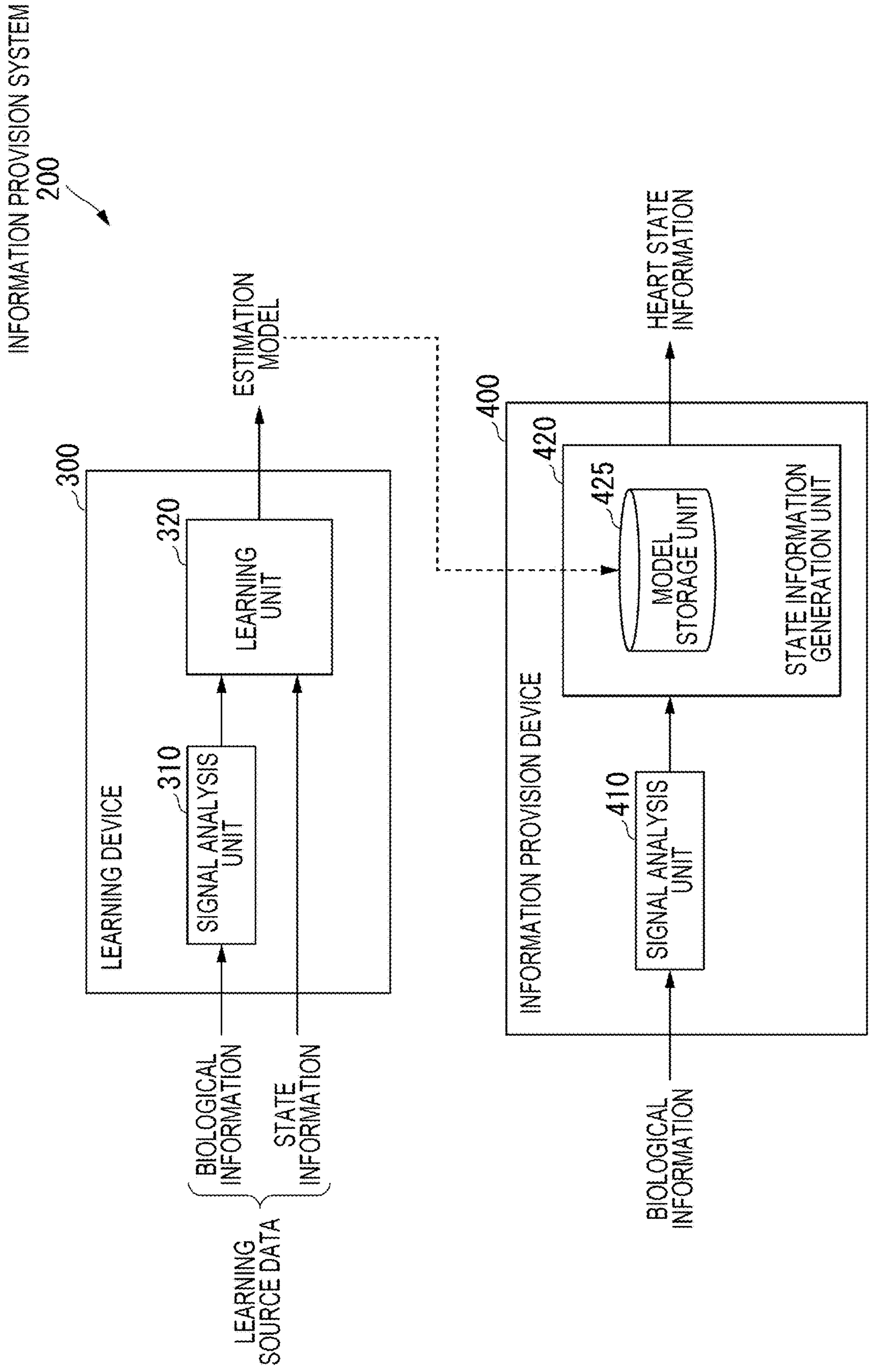
FIG. 60 is a diagram illustrating an example of a functional configuration of an information provision system 200 in a second embodiment.

As illustrated in FIG. 60, an information provision system 200 of the second embodiment includes a learning device 300 (learning apparatus) and an information provision device 400 (information providing apparatus). Hardware configurations of the information provision system 200, the learning device 300, and the information provision device 400 are similar to the hardware configuration of the signal analysis device 1 illustrated in FIG. 1, for example.

First, the learning device 300 will be described.

Figure 61:
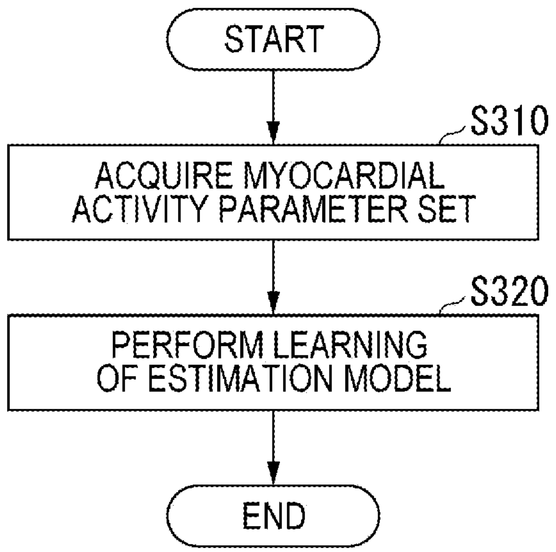
FIG. 61 is a flowchart illustrating an example of a flow of processing executed by a learning device 300 in the second embodiment.

As illustrated in FIG. 60, the learning device 300 includes a signal analysis unit 310 (signal analyzer) and a learning unit 320 (learner). The learning device 300 performs processing in step S310 and step S320 illustrated in FIG. 61.

[Learning Source Data Set and Learning Source Data]

A learning source data set is input to the learning device 300. The learning source data set includes a plurality of pieces of learning source data. Each piece of learning source data includes at least time-series biological information regarding the pulsation of a heart (hereinafter, referred to as "acquisition target heart") that is a target of acquisition of the learning source data, and heart state information that is information representing a state of the acquisition target heart. Each piece of learning source data may include information for specifying the learning source data, for example, an identification number uniquely assigned to the learning source data.

An example of the time-series biological information regarding the pulsation of the acquisition target heart is a waveform of an electrocardiogram of the acquisition target heart. The heart state information on the acquisition target heart is information uniquely specifying a diagnosis result regarding the state of the heart by the doctor who has looked at time-series biological information (for example, a waveform of an electrocardiogram) regarding the pulsation of the acquisition target heart. Specifically, the diagnosis result regarding the state of the heart by the doctor is whether or not the heart is in a normal state, which disease corresponds to in a case where the heart is not in the normal state, and the like. That is, for example, the heart state information only needs to be a specific numerical value assigned in advance to each of whether the heart is in the normal state, and which disease the heart has, such as "0" in a case where the doctor looking at the waveform of the electrocardiogram determines that the heart is in the normal state, "1" in a case where the doctor looking at the waveform of the electrocardiogram determines that the heart has Brugada syndrome, "2" in a case where the doctor looking at the waveform of the electrocardiogram determines that the heart has an ischemic heart disease, "3" in a case where the doctor looking at the waveform of the electrocardiogram determines that the heart is in an early repolarization syndrome, . . . .

Alternatively, for example, the heart state information may be a specific numerical value assigned in advance to each of whether the rhythm of the heart is in the normal state, and what kind of arrhythmia state the heart is in, such as "0" in a case where the doctor looking at the waveform of the electrocardiogram determines that the heart is in a normal sinus rhythm, "1" in a case where the doctor looking at the waveform of the electrocardiogram determines that the heart is in supraventricular premature contractions, "2" in a case where the doctor looking at the waveform of the electrocardiogram determines that the heart is in atrial fibrillation, "3" in a case where the doctor looking at the waveform of the electrocardiogram determines that the heart is in ventricular premature contractions, "4" in a case where the doctor looking at the waveform of the electrocardiogram determines that the heart is in ventricular fibrillation, . . . .

Alternatively, for example, the heart state information may be a specific numerical value assigned in advance to each of whether the blood flow state of the heart is the normal state, whether the blood flow state is an ischemic state, and where the site of the ischemic state is, such as "0" in a case where the doctor looking at the waveform of the electrocardiogram determines that the heart is in the normal coronary blood flow state, "1" in a case where the doctor looking at the waveform of the electrocardiogram determines that the heart is in the ischemic state of the myocardial inner layer, "2" in a case where the doctor looking at the waveform of the electrocardiogram determines that the heart is in the ischemic state of the myocardial inner layer and the outer layer (the state of transmural ischemia), "3" in a case where the doctor looking at the waveform of the electrocardiogram determines that the heart is in the myocardial infarction of the front wall, "4" in a case where the doctor looking at the waveform of the electrocardiogram determines that the heart is in the myocardial infarction of the lower wall, . . . .

When the number of pieces of learning source data included in the learning source data set is Y and each of integers greater than or equal to 1 and less than or equal to Y is y, the y-th learning source data includes at least time-series biological information regarding the pulsation of the acquisition target heart of the y-th learning source data, and heart state information on the acquisition target heart of the y-th learning source data. The Y pieces of learning source data included in the learning source data set may be acquired from each of acquisition target hearts of Y persons or may be acquired from acquisition target hearts of less than the Y persons. In a case where the learning source data acquired from acquisition target hearts of less than Y persons is set as the Y pieces of learning source data included in the learning source data set, a plurality of pieces of learning source data acquired from the acquisition target heart of the same person is included in the learning source data set; however, in this case, the plurality of pieces of learning source data acquired from the acquisition target hearts of the same person is preferably learning source data acquired at different times, and is preferably learning source data having different heart state information.

The time-series biological information regarding the pulsation of the heart included in each piece of learning source data may be a waveform for one cycle or waveforms for a plurality of cycles. For example, when the doctor diagnoses the state of the heart by looking at the waveform of any one cycle of waveforms of the electrocardiogram, it is sufficient that the waveform of the one cycle is included in the learning source data as time-series biological information regarding the pulsation of the heart, and information specifying one diagnosis result based on the waveform of the one cycle is included in the learning source data as the heart state information. Furthermore, for example, when the doctor diagnoses the state of the heart by looking at waveforms of a plurality of cycles among the waveforms of the electrocardiogram, it is sufficient that the waveforms of the plurality of cycles are included in the learning source data as time-series biological information regarding the pulsation of the heart, and information specifying a result of one diagnosis based on the waveforms of the plurality of cycles is included in the learning source data as the heart state information.

[Signal Analysis Unit 310]

The signal analysis unit 310 inputs the time-series biological information regarding the pulsation of the heart included in each piece of learning source data included in the learning source data set input to the learning device 300. The signal analysis unit 310 performs processing similar to that of the signal analysis device 1 of the first embodiment, thereby acquiring a set of myocardial activity parameters from time-series biological information regarding the pulsation of the heart (step S310). The myocardial activity parameter acquired by the signal analysis unit 310 is any one or more types of myocardial activity parameters described in the first embodiment, and is a myocardial activity parameter of a type selected in advance as a myocardial activity parameter used by the learning unit 320 described later. Hereinafter, a set of myocardial activity parameters acquired by the signal analysis unit 310 will be described as a "myocardial activity parameter set". Although there is a case where the myocardial activity parameter acquired by the signal analysis unit 310 is only one type for one cycle, the "set of myocardial activity parameters" and subsequent "myocardial activity parameter set" and "each myocardial activity parameter included in the myocardial activity parameter set" only needs to be appropriately read as "myocardial activity parameter". The myocardial activity parameter set acquired by the signal analysis unit 310 is output from the signal analysis unit 310 and input to the learning unit 320.

In a case where the time-series biological information regarding the pulsation of the heart included in each piece of learning source data is a waveform for one cycle, the signal analysis unit 310 acquires, as the myocardial activity parameter set, a set of one or more types of myocardial activity parameters described above from the waveform for the one cycle. In a case where the time-series biological information regarding the pulsation of the heart included in each piece of learning source data is waveforms for a plurality of cycles, the signal analysis unit 310 obtains a set of one or more types of myocardial activity parameters described above from the waveform of each cycle, and acquires a set of myocardial activity parameters for the plurality of cycles as the myocardial activity parameter set.

[Learning Unit 320]

The learning unit 320 inputs the myocardial activity parameter set obtained by the signal analysis unit 310 from the time-series biological information regarding the pulsation of the acquisition target heart included in each piece of learning source data included in the learning source data set input to the learning device 300, and the heart state information included in each piece of learning source data included in the learning source data set input to the learning device 300. The learning unit 320 uses a set of the myocardial activity parameter set and the heart state information based on the same learning source data as learning data. That is, in each piece of learning data, the myocardial activity parameter set and the heart state information are based on the time-series biological information regarding the pulsation of the same acquisition target heart. In other words, myocardial activity parameter sets are myocardial activity parameter sets corresponding to respective pieces of heart state information, and the pieces of heart state information are pieces of heart state information corresponding to the respective myocardial activity parameter sets.

When a set of all pieces of learning data used by the learning unit 320 is referred to as a learning data set, the learning data set used by the learning unit 320 includes a plurality of (Y) pieces of learning data. The y-th learning data includes at least a myocardial activity parameter set obtained by the signal analysis unit 310 from time-series biological information regarding the pulsation of the acquisition target heart included in the y-th learning source data, and heart state information that is information representing the state of the acquisition target heart of the y-th learning source data.

Using the learning data set, more specifically, using a set of a myocardial activity parameter set included in each piece of learning data included in the learning data set and the heart state information corresponding to the myocardial activity parameter set, the learning unit 320 performs learning of an estimation model that obtains heart state information corresponding to a myocardial activity parameter set with the myocardial activity parameter set as an input to obtain a learned estimation model (step S320). The learned estimation model obtained by the learning unit 320 is output from the learning unit 320 to be an output of the learning device 300. It is sufficient that a known learning technique is used for learning of the estimation model, and the number of pieces of learning data is a sufficient number of pieces for performing learning of the estimation model. That is, the number of pieces of learning source data only needs to be the same as the number of pieces of learning data.

[First Example of Learning Device 300]

An outline of each piece of data and operation of the learning device 300 will be described using a case where the time-series biological information regarding the pulsation of the heart included in each piece of learning source data is a waveform for one cycle as a first example.

When time-series biological information regarding the pulsation of the heart is Wave(y) and heart state information is Info(y) that are included in the y-th learning source data, the y-th learning source data is [Wave(y), Info(y)]. That is, the learning source data set is [[Wave(1), Info(1)], [Wave(2), Info(2)], . . . , [Wave(Y), Info(Y)]].

The signal analysis unit 310 obtains a myocardial activity parameter set Para(y) from the time-series biological information Wave(y) regarding the pulsation of the heart for each y of 1, . . . , and Y. Each myocardial activity parameter set Para(y) is a set of one or more types of myocardial activity parameters acquired by processing similar to that performed by the signal analysis device 1 of the first embodiment from the time-series biological information Wave(y) regarding the pulsation of the heart, and thus includes one or a plurality of elements.

Since the learning unit 320 uses a set of the myocardial activity parameter set and the heart state information based on the same learning source data as the learning data, the y-th learning data is [Para(y), Info(y)]. That is, the learning data set is [[Para(1), Info(1)], [Para(2), Info(2)], . . . , [Para(Y), Info(Y)]]. Using [Para(1), Info(1)], [Para(2), Info(2)], . . . , and [Para(Y), Info(Y)], the learning unit 320 performs learning of an estimation model that obtains heart state information corresponding to a myocardial activity parameter set with the myocardial activity parameter set as an input to obtain a learned estimation model.

[Second Example of Learning Device 300]

An outline of each piece of data and operation of the learning device 300 will be described using a case where the time-series biological information regarding the pulsation of the heart included in each piece of learning source data is waveforms for a plurality of cycles as a second example. In the second example, it is set that the time-series biological information regarding the pulsation of the heart included in each piece of learning source data is waveforms for Z cycles, and each of cycle indexes 1, . . . , and Z is z. That is, Z is an integer greater than or equal to 2, and z is an integer greater than or equal to 1 and less than or equal to Z.

When a waveform of each cycle included in the time-series biological information regarding the pulsation of the heart included in the y-th learning source data is Wave(y, z), and the heart state information included in the y-th learning source data is Info(y), the y-th learning source data is [Wave(y, 1), Wave(y, 2), . . . , Wave(y, Z), Info(y)].

The signal analysis unit 310 obtains one or more types of myocardial activity parameters Para(y, z) from each Wave(y, z) for each y of 1, . . . , and Y and each z of 1, . . . , and Z, thereby obtaining a myocardial activity parameter set [Para(y, 1), Para(y, 2), . . . , Para(y, Z)] of each y of 1, . . . , and Y. Each myocardial activity parameter Para(y, z) is one or more types of myocardial activity parameters acquired by processing similar to that performed by the signal analysis device 1 of the first embodiment from the waveform Wave(y, z) of each cycle included in the time-series biological information regarding the pulsation of the heart, and thus includes one or a plurality of elements.

Since the learning unit 320 uses a set of the myocardial activity parameter set and the heart state information based on the same learning source data as the learning data, an example of the y-th learning data is [Para(y, 1), Para(y, 2), . . . , Para(y, Z), Info(y)]. That is, the learning data set is [[Para(1, 1), Para(1, 2), . . . , Para(1, Z), Info(1)], [Para(2, 1), Para(2, 2), . . . , Para(2, Z), Info(2)], . . . [Para(Y, 1), Para(Y, 2), . . . . Para(Y, Z), Info(Y)]]. Using [Para(1, 1), Para(1, 2), . . . , Para(1, Z), Info(1)], [Para(2, 1), Para(2, 2), . . . , Para(2, Z), Info(2)], . . . , [Para(Y, 1), Para(Y, 2), Para(Y, Z), Info(Y)], the learning unit 320 performs learning of an estimation model that obtains heart state information corresponding to a myocardial activity parameter set with the myocardial activity parameter set as an input to obtain and output a learned estimation model.

Next, the information provision device 400 will be described.

Figure 62:
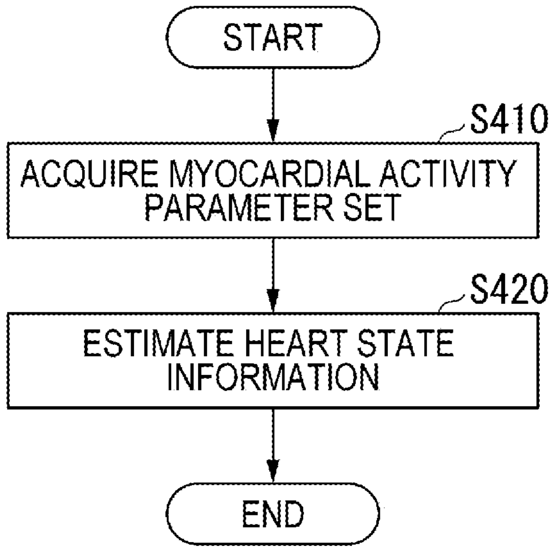
FIG. 62 is a flowchart illustrating an example of a flow of processing executed by an information provision device 400 in the second embodiment.

Time-series biological information regarding the pulsation of a heart to be a target of information provision (hereinafter, referred to as an "information provision target heart") is input to the information provision device 400. The information provision device 400 acquires a myocardial activity parameter from the time-series biological information regarding the pulsation of the information provision target heart, and uses the learned estimation model, with the acquired myocardial activity parameter as an input, to obtain and output heart state information that is information representing the state of the heart corresponding to the myocardial activity parameter. As illustrated in FIG. 60, the information provision device 400 includes a signal analysis unit 410 and a state information generation unit 420 (state information generator). The information provision device 400 performs processing in step S410 and step S420 illustrated in FIG. 62.

[Signal Analysis Unit 410]

The time-series biological information regarding the pulsation of the information provision target heart input to the information provision device 400 is input to the signal analysis unit 410. The signal analysis unit 410 performs processing similar to that of the signal analysis unit 310 of the learning device 300, that is, performs processing similar to that of the signal analysis device 1 of the first embodiment, thereby acquiring the myocardial activity parameter set from the time-series biological information regarding the pulsation of the information provision target heart (step S410). The myocardial activity parameter set acquired by the signal analysis unit 410 is output from the signal analysis unit 410 and input to the state information generation unit 420. The myocardial activity parameter set acquired by the signal analysis unit 410 is a set of any one or more types of myocardial activity parameters described in the first embodiment. The one or more types of myocardial activity parameters are myocardial activity parameters of types selected in advance as myocardial activity parameters used by the state information generation unit 420 to be described later, and are myocardial activity parameters of types used by the learning unit 320 of the second embodiment for learning of the estimation model.

In a case where the time-series biological information regarding the pulsation of the input information provision target heart is a waveform for one cycle, the signal analysis unit 410 acquires, as a myocardial activity parameter set, a set of one or more types of myocardial activity parameters described above from the waveform for one cycle. In a case where the time-series biological information regarding the pulsation of the input information provision target heart is waveforms for a plurality of cycles, the signal analysis unit 410 obtains a set of one or more types of myocardial activity parameters described above from the waveform of each cycle, and acquires, as a myocardial activity parameter set, a set of one or more types of myocardial activity parameters for the plurality of cycles.

[State Information Generation Unit 420]

As illustrated in FIG. 60, the state information generation unit 420 includes a model storage unit 425. The learned estimation model output from the learning device 300 of the second embodiment is stored in advance in the model storage unit 425. The learned estimation model stored in advance in the model storage unit 425 is an estimation model that obtains heart state information that is information representing the state of the heart corresponding to a myocardial activity parameter set with the myocardial activity parameter set as an input.

The myocardial activity parameter set of the information provision target heart output by the signal analysis unit 410 is input to the state information generation unit 420. The state information generation unit 420 uses the learned estimation model stored in advance in the model storage unit 425 to obtain heart state information that is information representing the state of the information provision target heart with the myocardial activity parameter set of the information provision target heart as an input (step S420). The heart state information obtained by the state information generation unit 420 is output from the state information generation unit 420 to be an output of the information provision device 400.

[First Example of Information Provision Device 400]

An outline of each piece of data and operation of the information provision device 400 will be described using a case where the time-series biological information regarding the pulsation of the information provision target heart input to the information provision device 400 is a waveform for one cycle as a first example.

When the time-series biological information regarding the pulsation of the information provision target heart input to the information provision device 400 is WAVE, the signal analysis unit 410 obtains a myocardial activity parameter set PARA from the time-series biological information WAVE regarding the pulsation of the information provision target heart. The myocardial activity parameter set PARA is a set of one or more types of myocardial activity parameters acquired by processing similar to that performed by the signal analysis device 1 of the first embodiment from the time-series biological information WAVE regarding the pulsation of the information provision target heart, and thus includes one or a plurality of elements.

The state information generation unit 420 uses the learned estimation model stored in advance in the model storage unit 425 to obtain one piece of heart state information INFO corresponding to the myocardial activity parameter set PARA from the myocardial activity parameter set PARA.

[Second Example of Information Provision Device 400]

An outline of each piece of data and operation of the information provision device 400 will be described using a case where the time-series biological information regarding the pulsation of the information provision target heart input to the information provision device 400 is waveforms for a plurality of cycles as a second example. In the second example, it is set that the time-series biological information regarding the pulsation of the information provision target heart is a waveform for Z cycles, and each of the cycle indexes 1, . . . , and Z is z. That is, Z is an integer greater than or equal to 2, and z is an integer greater than or equal to 1 and less than or equal to Z.

When the waveform of each cycle included in the time-series biological information regarding the pulsation of the information provision target heart input to the information provision device 400 is WAVE(z), the signal analysis unit 410 obtains one or more types of myocardial activity parameters PARA(z) from each WAVE(z) for each z of 1, . . . , and Z, thereby obtaining a myocardial activity parameter set [Para(1), Para(2), . . . , Para(Z)]. The myocardial activity parameter PARA(z) is one or more types of myocardial activity parameters acquired by processing similar to that performed by the signal analysis device 1 of the first embodiment from the waveform WAVE(z) of each cycle included in the time-series biological information regarding the pulsation of the information provision target heart, and thus includes one or a plurality of elements.

The state information generation unit 420 uses the learned estimation model stored in advance in the model storage unit 425 to obtain one piece of heart state information INFO corresponding to the myocardial activity parameter set [Para (1), Para(2), . . . , Para(Z)] from the myocardial activity parameter set [Para(1), Para(2), Para(Z)].

The heart state information obtained by the state information generation unit 420 is an estimation result by the information provision device 400 regarding the state of the information provision target heart. That is, for example, the heart state information obtained by the state information generation unit 420 represents an estimation result regarding whether the information provision target heart is in the normal state, or which disease the heart has, as a specific numerical value assigned in advance, such as “0” corresponding to that the information provision target heart is in the normal state, “1” corresponding to that the information provision target heart has Brugada syndrome, “2” corresponding to that the information provision target heart has ischemic heart disease, “3” corresponding to that the information provision target heart has an early repolarization syndrome, Alternatively, for example, the heart state information obtained by the state information generation unit 420 represents an estimation result regarding whether the rhythm of the information provision target heart is in the normal state, or what kind of arrhythmia state the heart is in, as a specific numerical value assigned in advance, such as “0” corresponding to that the information provision target heart is in a normal sinus rhythm, “1” corresponding to that the information provision target heart is in supraventricular premature contractions, “2” corresponding to that the information provision target heart is in atrial fibrillation, “3” corresponding to that the information provision target heart is in ventricular premature contraction, “4” corresponding to that the information provision target heart is in ventricular fibrillation, Alternatively, for example, the heart state information obtained by the state information generation unit 420 represents an estimation result regarding whether the blood flow state of the information provision target heart is the normal state, whether the blood flow state is an ischemic state, or where the site of the ischemic state is, as a specific numerical value assigned in advance, such as “0” corresponding to that the information provision target heart is in the normal coronary blood flow state, “1” corresponding to that the information provision target heart is in the ischemic state of the myocardial inner layer, “2” corresponding to that the information provision target heart is in the ischemic state of the myocardial inner layer and the outer layer (the state of transmural ischemia), “3” corresponding to that the information provision target heart is in the myocardial infarction of the front wall, “4” corresponding to that the information provision target heart is in the myocardial infarction of the lower wall,

Third Embodiment

In the second embodiment, learning of the estimation model and estimation of the heart state information are performed after obtaining the myocardial activity parameter set from the time-series biological information regarding the pulsation of the heart, but learning of the estimation model and estimation of the heart state information may be performed using the myocardial activity parameter set obtained in advance. This mode will be described as a third embodiment, focusing on differences from the second embodiment.

Figure 63:
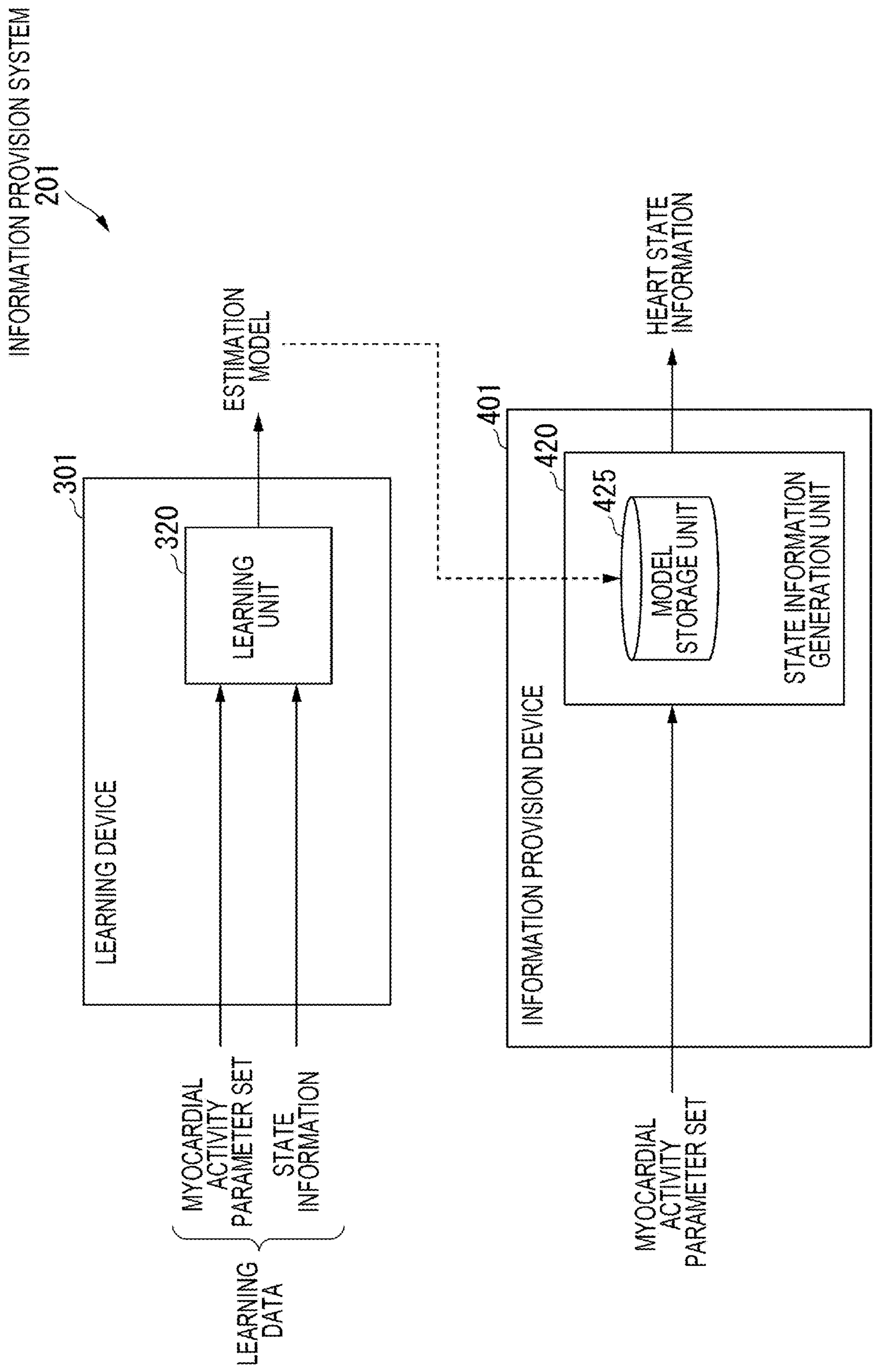
FIG. 63 is a diagram illustrating an example of a functional configuration of an information provision system 201 in a third embodiment.

As illustrated in FIG. 63, an information provision system 201 of the third embodiment includes a learning device 301 and an information provision device 401. Hardware configurations of the information provision system 201, the learning device 301, and the information provision device 401 are similar to the hardware configuration of the signal analysis device 1 illustrated in FIG. 1, for example.

First, the learning device 301 will be described.

[[Learning Device 301]]

Figure 64:
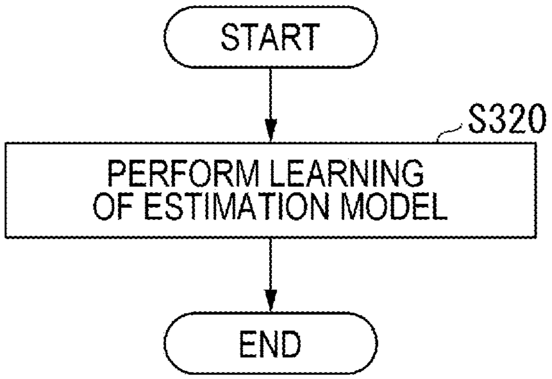
FIG. 64 is a flowchart illustrating an example of a flow of processing executed by a learning device 301 in the third embodiment.

As illustrated in FIG. 63, the learning device 301 includes the learning unit 320. The learning device 301 performs processing in step S320 illustrated in FIG. 64.

[Learning Data Set and Learning Data]

A learning data set is input to the learning device 300. The learning data set includes a plurality of pieces of learning data. Each piece of learning data includes at least a myocardial activity parameter set of an acquisition target heart that is a heart targeted for acquisition of the learning data and heart state information that is information representing a state of the acquisition target heart. Each piece of learning data may include information for specifying the learning data, for example, an identification number uniquely assigned to the learning data.

When the number of pieces of learning data included in the learning data set is Y and each of integers greater than or equal to 1 and less than or equal to Y is y, the Y-th learning data includes at least a myocardial activity parameter set of the acquisition target heart of the y-th learning data and heart state information that is information representing a state of the acquisition target heart of the y-th learning data.

The myocardial activity parameter set of the acquisition target heart is a myocardial activity parameter set obtained from time-series biological information regarding the pulsation of the acquisition target heart by processing similar to that performed by the signal analysis unit 310 of the learning device 300 of the second embodiment, that is, by processing similar to that performed by the signal analysis device 1 of the first embodiment. The heart state information on the acquisition target heart is the same as the heart state information on the acquisition target heart of the second embodiment.

[Learning Unit 320]

The learning data set input to the learning device 301 is input to the learning unit 320. That is, the learning unit 320 inputs the myocardial activity parameter set included in each piece of learning data included in the learning data set input to the learning device 301, and the heart state information included in each piece of learning data included in the learning data set input to the learning device 301. The learning unit 320 uses a set of the myocardial activity parameter set and the heart state information included in the same learning data as the learning data. That is, in each piece of learning data, the myocardial activity parameter set and the heart state information are based on the time-series biological information regarding the pulsation of the same heart. In other words, the myocardial activity parameter set is a myocardial activity parameter set corresponding to the heart state information, and the heart state information is heart state information corresponding to the myocardial activity parameter set.

Similarly to the learning unit 320 of the second embodiment, using the learning data set, more specifically, using a set of the myocardial activity parameter set included in each piece of learning data included in the learning data set and the heart state information corresponding to the myocardial activity parameter set, the learning unit 320 performs learning of the estimation model that obtains the heart state information corresponding to the myocardial activity parameter set with the myocardial activity parameter set as an input to obtain the learned estimation model (step S320). The learned estimation model obtained by the learning unit 320 is output from the learning unit 320 to be an output of the learning device 300. It is sufficient that a known learning technique is used for learning of the estimation model, and the number of pieces of learning data is a sufficient number of pieces for performing learning of the estimation model. A specific example of the learning unit 320 is as described in the second embodiment.

Next, the information provision device 401 will be described.

[[Information Provision Device 401]]

Figure 65:
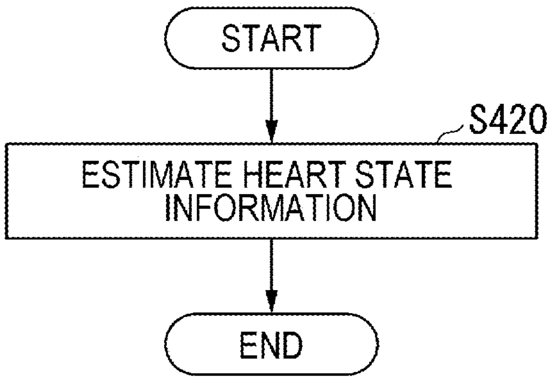
FIG. 65 is a flowchart illustrating an example of a flow of processing executed by an information provision device 401 in the third embodiment.

A myocardial activity parameter set of an information provision target heart that is a heart to be a target of information provision is input to the information provision device 401. The myocardial activity parameter set of the information provision target heart is a myocardial activity parameter set obtained from time-series biological information regarding the pulsation of the information provision target heart by processing similar to that performed by the signal analysis unit 410 of the information provision device 400 of the second embodiment, that is, by processing similar to that performed by the signal analysis device 1 of the first embodiment. The information provision device 401 uses the learned estimation model to obtain heart state information that is information representing the state of the heart corresponding to the myocardial activity parameter set from the input myocardial activity parameter set, and output the heart state information. As illustrated in FIG. 63, the information provision device 401 includes the state information generation unit 420. The information provision device 401 performs processing in step S420 illustrated in FIG. 65.

[State Information Generation Unit 420]

As illustrated in FIG. 63, the state information generation unit 420 includes the model storage unit 425. The learned estimation model output by the learning device 301 of the third embodiment is stored in advance in the model storage unit 425. The learned estimation model stored in advance in the model storage unit 425 is an estimation model that obtains heart state information that is information representing the state of the heart corresponding to a myocardial activity parameter set with the myocardial activity parameter set as an input.

The myocardial activity parameter set of the information provision target heart input to the information provision device 401 is input to the state information generation unit 420. The state information generation unit 420 uses the learned estimation model stored in advance in the model storage unit 425 to obtain heart state information that is information representing the state of the information provision target heart with the myocardial activity parameter set of the information provision target heart as an input (step S420). The heart state information obtained by the state information generation unit 420 is output from the state information generation unit 420 to be an output of the information provision device 401. A specific example of the state information generation unit 420 is as described in the second embodiment. The heart state information obtained by the state information generation unit 420 is similar to the heart state information obtained by the state information generation unit 420 of the second embodiment, and is an estimation result by the information provision device 401 regarding the state representing the state of the information provision target heart, and a specific example is as described in the second embodiment.

Modifications of Second Embodiment and Third Embodiment

Figure 66:
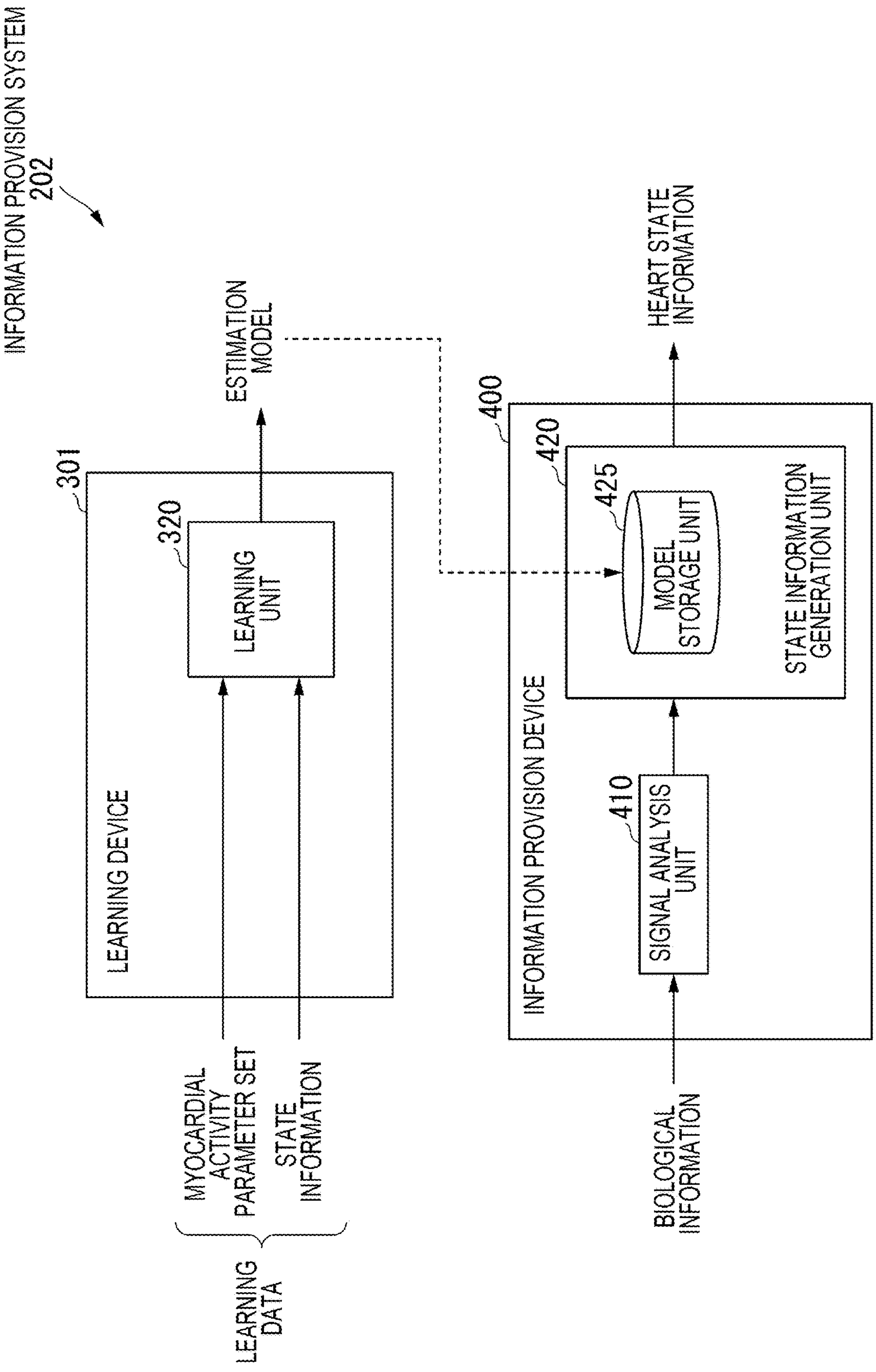
FIG. 66 is a diagram illustrating an example of a functional configuration of an information provision system 202 in a modification of the second embodiment and the third embodiment.
Figure 67:
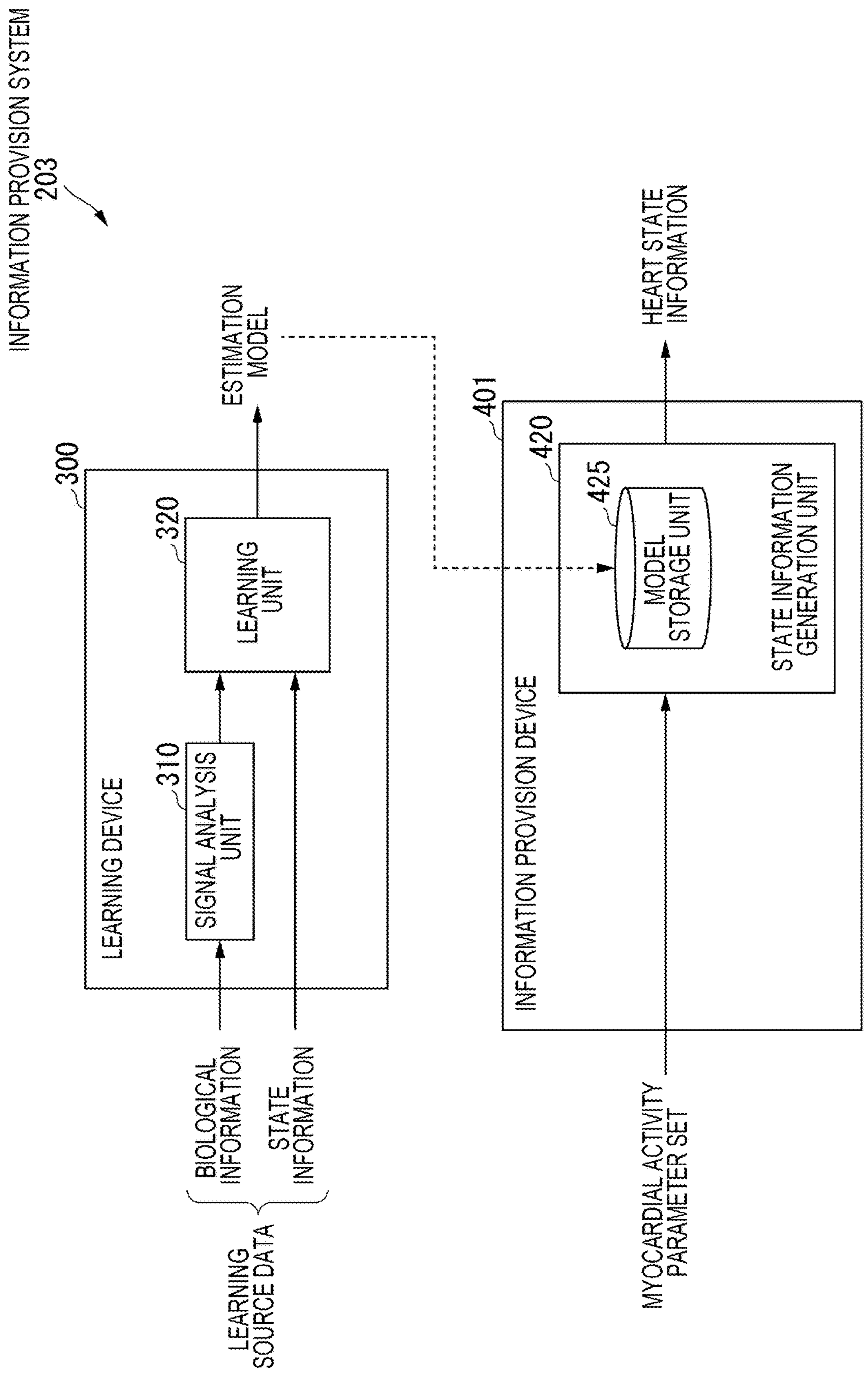
FIG. 67 is a diagram illustrating an example of a functional configuration of an information provision system 203 in the modification of the second embodiment and the third embodiment.

As can be seen from the description in the third embodiment, the estimation model obtained by the learning device 300 of the second embodiment and the estimation model obtained by the learning device 301 of the third embodiment are equivalent to each other. Thus, the learned estimation model output by the learning device 301 of the third embodiment may be stored in advance in the model storage unit 425 of the information provision device 400 of the second embodiment, or the learned estimation model output by the learning device 300 of the learning device of the second embodiment may be stored in advance in the model storage unit 425 of the information provision device 401 of the third embodiment. That is, the information provision system may be configured as an information provision system 202 including the learning device 301 of the third embodiment and the information provision device 400 of the second embodiment as illustrated in FIG. 66, or may be configured as an information provision system 203 including the learning device 300 of the second embodiment and the information provision device 401 of the third embodiment as illustrated in FIG. 67. Hardware configurations of the information provision system 202, the information provision system 203, the learning device 300, the learning device 301, the information provision device 400, and the information provision device 401 are similar to the hardware configuration of the signal analysis device 1 illustrated in FIG. 1, for example.

Summary of Second and Third Embodiments and Modifications Thereof

[Learning Device]

Both the learning device 300 of the second embodiment and the learning device 301 of the third embodiment set that a learning data set includes Y pieces of learning data (Y is a plural number), and each of the Y pieces of learning data includes a myocardial activity parameter set of a heart that is a target of the y-th learning data, and heart state information representing a state of the heart that is the target of the y-th learning data, where each of integers greater than or equal to 1 and less than or equal to Y is y, and include the learning unit 320 that performs learning of an estimation model that obtains heart state information that is information representing a state of a heart corresponding to a myocardial activity parameter set with the myocardial activity parameter set as an input, by using the learning data set. Then, the learning device 300 of the second embodiment further includes the signal analysis unit 310 that obtains a myocardial activity parameter set, with time-series biological information regarding pulsation of the heart that is the target of each y-th learning data as an input. However, the myocardial activity parameter set of the heart that is the target of the y-th learning data in the learning device 300 of the second embodiment and the learning device 301 of the third embodiment includes predetermined types of myocardial activity parameters of one or more types among a plurality of types of myocardial activity parameters included in a first group to be described later, a plurality of types of myocardial activity parameters included in a second group to be described later, a plurality of types of myocardial activity parameters included in a third group to be described later, and one or more types of myocardial activity parameters included in a fourth group to be described later, in each cycle of the time-series biological information regarding the pulsation of the heart that is the target of each y-th learning data.

[Information Provision Device]

Both the information provision device 400 of the second embodiment and the information provision device 401 of the third embodiment include the state information generation unit 420 that stores in advance an estimation model that obtains heart state information that is information representing a state of a heart corresponding to a myocardial activity parameter set with the myocardial activity parameter set as an input, and obtains heart state information that is information representing a state of an information provision target heart with a myocardial activity parameter set of the information provision target heart as an input, by using the estimation model. Then, the information provision device 400 of the second embodiment further includes the signal analysis unit 410 that obtains a myocardial activity parameter set, with time-series biological information regarding the pulsation of the information provision target heart as an input. However, the myocardial activity parameter set of the information provision target heart in the information provision device 400 of the second embodiment and the information provision device 401 of the third embodiment includes predetermined types of myocardial activity parameters of one or more types among the plurality of types of myocardial activity parameters included in the first group to be described later, the plurality of types of myocardial activity parameters included in the second group to be described later, the plurality of types of myocardial activity parameters included in the third group to be described later, and one or more types of myocardial activity parameters included in the fourth group to be described later, in each cycle of the time-series biological information regarding the pulsation of the information provision target heart.

[Plurality of Types of Myocardial Activity Parameters Included in First Group]

The plurality of types of myocardial activity parameters included in the first group is a parameter specifying a first unimodal distribution, a parameter specifying a first cumulative distribution function, a parameter specifying a second unimodal distribution, a parameter specifying a second cumulative distribution function, weight of the first cumulative distribution function, weight of the second cumulative distribution function, a ratio between the weight of the first cumulative distribution function and the weight of the second cumulative distribution function, and a first level value when a first target time waveform is approximated by a first approximate time waveform that is a time waveform represented by a difference or a weighted difference between the first cumulative distribution function that is a cumulative distribution function of the first unimodal distribution and the second cumulative distribution function that is a cumulative distribution function of the second unimodal distribution, or a first approximate time waveform that is a time waveform represented by addition of the first level value and the difference or the weighted difference between the first cumulative distribution function that is a cumulative distribution function of the first unimodal distribution and the second cumulative distribution function that is a cumulative distribution function of the second unimodal distribution when a waveform in a time section of an R wave included in a waveform for one cycle of time-series biological information regarding pulsation of a heart is the first target time waveform.

[Plurality of Types of Myocardial Activity Parameters Included in Second Group]

The plurality of types of myocardial activity parameters included in the second group is a parameter specifying a third unimodal distribution, a parameter specifying a third cumulative distribution function, a parameter specifying a fourth unimodal distribution, a parameter specifying a fourth cumulative distribution function, weight of the third cumulative distribution function, weight of the fourth cumulative distribution function, a ratio between the weight of the third cumulative distribution function and the weight of the fourth cumulative distribution function, and a second level value when a second target inverse time waveform is approximated by a second approximate inverse time waveform that is a waveform represented by a difference or a weighted difference between the third cumulative distribution function that is a cumulative distribution function of the third unimodal distribution and the fourth cumulative distribution function that is a cumulative distribution function of the fourth unimodal distribution, or a second approximate inverse time waveform represented by addition of the second level value and the difference or the weighted difference between the third cumulative distribution function that is a cumulative distribution function of the third unimodal distribution and the fourth cumulative distribution function that is a cumulative distribution function of the fourth unimodal distribution when a waveform in a time section of a T wave included in a waveform for one cycle of the time-series biological information regarding the pulsation of the heart is a second target time waveform, and a waveform obtained by inverting the time axis of the second target time waveform is the second target inverse time waveform.

Alternatively, the plurality of types of myocardial activity parameters included in the second group is a parameter specifying the third unimodal distribution, a parameter specifying the third cumulative distribution function, a parameter specifying the fourth unimodal distribution, a parameter specifying the fourth cumulative distribution function, weight of a third inverse cumulative distribution function, weight of a fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function when a waveform in the time section of the T wave included in a waveform for one cycle of the time-series biological information regarding the pulsation of the heart is the second target time waveform, a cumulative distribution function of the third unimodal distribution is the third cumulative distribution function, a cumulative distribution function of the fourth unimodal distribution is the fourth cumulative distribution function, a function obtained by subtracting the third cumulative distribution function from 1 is the third inverse cumulative distribution function, and a function obtained by subtracting the fourth cumulative distribution function from 1 is the fourth inverse cumulative distribution function.

[Plurality of Types of Myocardial Activity Parameters Included in Third Group]

The plurality of types of myocardial activity parameters included in the third group is a parameter specifying a fifth unimodal distribution, a parameter specifying a fifth cumulative distribution function, and weight of the fifth cumulative distribution function when a residual time waveform is approximated by an approximate residual time waveform that is a time waveform represented by the fifth cumulative distribution function that is a cumulative distribution function of the fifth unimodal distribution or by multiplication of the fifth cumulative distribution function by weight, with any one of a time waveform of a difference between the first target time waveform and the first approximate time waveform, a time waveform of a difference between the second target time waveform and the second approximate time waveform, and a time waveform obtained by inverting the time axis of a waveform of a difference between the second target inverse time waveform and the second approximate inverse time waveform as the residual time waveform.

Alternatively, the plurality of types of myocardial activity parameters included in the third group is a parameter specifying the fifth unimodal distribution, a parameter specifying the fifth cumulative distribution function, a parameter specifying a sixth unimodal distribution, a parameter specifying a sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function that is a cumulative distribution function of the fifth unimodal distribution and the sixth cumulative distribution function that is a cumulative distribution function of the sixth unimodal distribution, with at least one of the time waveform of the difference between the first target time waveform and the first approximate time waveform, the time waveform of the difference between the second target time waveform and the second approximate time waveform, or the time waveform obtained by inverting the time axis of the waveform of the difference between the second target inverse time waveform and the second approximate inverse time waveform as the residual time waveform.

[One or more types of myocardial activity parameters included in Fourth Group]

The one or more types of myocardial activity parameters included in the fourth group are myocardial activity parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group.

Note that, all or some of the functions of the signal analysis device 1 and/or the information provision systems 200, 201, 202, and 203, and/or the learning devices 300 and 301, and/or the information provision devices 400 and 401 may be implemented by using hardware such as an application specific integrated circuit (ASIC), a programmable logic device (PLD), or a field programmable gate array (FPGA). The program may be recorded on a computer-readable recording medium. The computer-readable recording medium is, for example, a portable medium such as a flexible disk, a magneto-optical disk, a ROM, or a CD-ROM or a storage device such as a hard disk built in a computer system. The program may be transmitted via an electrical communication line.

Although the embodiments of the present invention have been described in detail with reference to the drawings, specific configurations are not limited to the embodiments and include design and the like within the gist of the present invention.

REFERENCE SIGNS LIST

1 Signal analysis device
11 Control unit
12 Input unit
13 Communication unit
14 Storage unit
15 Output unit
91 Processor
92 Memory
110 Electrocardiogram acquisition unit
120 Fitting information acquisition unit
130 Analysis unit
131 Fitting unit
132 Myocardial activity information parameter acquisition unit
140 Recording unit
200, 201, 202, 203 Information provision system
300, 301 Learning device
310 Signal analysis unit
320 Learning unit
400, 401 information provision device
410 Signal analysis unit
420 State information generation unit
425 Model storage unit

The invention claimed is:

1. A learning device comprising a learner that:

sets a waveform in a time section of an R wave included in a waveform for one cycle indicating a cardiac cycle of a heart as a first target time waveform;

sets a waveform in a time section of a T wave included in the waveform as a second target time waveform;

sets a waveform obtained by inverting a time axis of the second target time waveform as a second target inverse time waveform;

sets a cumulative distribution function of a first unimodal distribution as a first cumulative distribution function, and sets a cumulative distribution function of a second unimodal distribution as a second cumulative distribution function;

sets, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function;

sets a cumulative distribution function of a third unimodal distribution as a third cumulative distribution function, sets a cumulative distribution function of a fourth unimodal distribution as a fourth cumulative distribution function, sets a function obtained by subtracting the third cumulative distribution function from 1 as a third inverse cumulative distribution function, and sets a function obtained by subtracting the fourth cumulative distribution function from 1 as a fourth inverse cumulative distribution function;

sets, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function;

sets, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, sets a cumulative distribution function of a fifth unimodal distribution as a fifth cumulative distribution function, and sets a cumulative distribution function of a sixth unimodal distribution as a sixth cumulative distribution function;

sets, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function;

sets, as one or more types of myocardial activity parameters included in the fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group;

sets, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and performs learning of an estimation model that obtains heart state information that is information representing a state of a heart corresponding to a myocardial activity parameter with the myocardial activity parameter set as an input, by using a learning data set, wherein the learning data set includes Y pieces of learning data (Y is a plural number), and each of the Y pieces of learning data includes a myocardial activity parameter set of a heart that is a target of a y-th learning data, and heart state information that is information representing a state of the heart that is the target of the y-th learning data, where each of integers greater than or equal to 1 and less than or equal to Y is y.

2. The learning device according to claim 1, further comprising a signal analyzer that obtains the myocardial activity parameter set from each of waveforms indicating one or more cardiac cycles of hearts that are targets of the Y pieces of learning data.

3. The learning device according to claim 1, wherein each of the unimodal distributions is a Gaussian distribution.

4. An information provision device comprising a state information generator that:

sets a waveform in a time section of an R wave included in a waveform for one cycle indicating a cardiac cycle of a heart as a first target time waveform;

sets a waveform in a time section of a T wave included in the waveform as a second target time waveform;

sets a waveform obtained by inverting a time axis of the second target time waveform as a second target inverse time waveform;

sets a cumulative distribution function of a first unimodal distribution as a first cumulative distribution function, and sets a cumulative distribution function of a second unimodal distribution as a second cumulative distribution function;

sets, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function;

sets a cumulative distribution function of a third unimodal distribution as a third cumulative distribution function, sets a cumulative distribution function of a fourth unimodal distribution as a fourth cumulative distribution function, sets a function obtained by subtracting the third cumulative distribution function from 1 as a third inverse cumulative distribution function, and sets a function obtained by subtracting the fourth cumulative distribution function from 1 as a fourth inverse cumulative distribution function;

sets, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function;

sets, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, sets a cumulative distribution function of a fifth unimodal distribution as a fifth cumulative distribution function, and sets a cumulative distribution function of a sixth unimodal distribution as a sixth cumulative distribution function;

sets, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function;

sets, as one or more types of myocardial activity parameters included in a fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group;

sets, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and obtains heart state information on an information provision target heart with the myocardial activity parameter set of the information provision target heart that is a heart to be a target of information provision as an input, by using an estimation model, wherein the estimation model that obtains heart state information that is information representing a state of a heart corresponding to the myocardial activity parameter set with the myocardial activity parameter set as an input is stored in advance.

5. The information provision device according to claim 4, further comprising a signal analyzer that obtains the myocardial activity parameter set from a waveform indicating one or more cardiac cycles of the information provision target heart.

6. The information provision device according to claim 4, wherein each of the unimodal distributions is a Gaussian distribution.

7. A learning method executed by a learning device, the learning method comprising a learning step of:

setting a waveform in a time section of an R wave included in a waveform for one cycle indicating a cardiac cycle of a heart as a first target time waveform;

setting a waveform in a time section of a T wave included in the waveform as a second target time waveform;

setting a waveform obtained by inverting a time axis of the second target time waveform as a second target inverse time waveform;

setting a cumulative distribution function of a first unimodal distribution as a first cumulative distribution function, and setting a cumulative distribution function of a second unimodal distribution as a second cumulative distribution function;

setting, as a plurality of types of myocardial activity parameters included in a first group, a parameter specifying the first unimodal distribution, a parameter specifying the first cumulative distribution function, a parameter specifying the second unimodal distribution, a parameter specifying the second cumulative distribution function, weight of the first cumulative distribution function, weight of the second cumulative distribution function, a ratio between the weight of the first cumulative distribution function and the weight of the second cumulative distribution function, and a first level value when the first target time waveform is approximated by a first approximate time waveform that is a time waveform represented by a difference or a weighted difference between the first cumulative distribution function and the second cumulative distribution function, or a first approximate time waveform that is a time waveform represented by addition of the first level value and the difference or the weighted difference between the first cumulative distribution function and the second cumulative distribution function;

setting a cumulative distribution function of a third unimodal distribution as a third cumulative distribution function, setting a cumulative distribution function of a fourth unimodal distribution as a fourth cumulative distribution function, setting a function obtained by subtracting the third cumulative distribution function from 1 as a third inverse cumulative distribution function, and setting a function obtained by subtracting the fourth cumulative distribution function from 1 as a fourth inverse cumulative distribution function;

setting, as a plurality of types of myocardial activity parameters included in a second group, a parameter specifying the third unimodal distribution, a parameter specifying the third cumulative distribution function, a parameter specifying the fourth unimodal distribution, a parameter specifying the fourth cumulative distribution function, weight of the third cumulative distribution function, weight of the fourth cumulative distribution function, a ratio between the weight of the third cumulative distribution function and the weight of the fourth cumulative distribution function, and a second level value when the second target inverse time waveform is approximated by a second approximate inverse time waveform that is a waveform represented by a difference or a weighted difference between the third cumulative distribution function and the fourth cumulative distribution function, or a second approximate inverse time waveform that is a waveform represented by addition of the second level value and the difference or the weighted difference between the third cumulative distribution function and the fourth cumulative distribution function, or a parameter specifying the third unimodal distribution, a parameter specifying the third cumulative distribution function, a parameter specifying the fourth unimodal distribution, a parameter specifying the fourth cumulative distribution function, weight of the third inverse cumulative distribution function, weight of the fourth inverse cumulative distribution function, a ratio between the weight of the third inverse cumulative distribution function and the weight of the fourth inverse cumulative distribution function, and a second level value when the second target time waveform is approximated by a second approximate time waveform that is a time waveform represented by a difference or a weighted difference between the third inverse cumulative distribution function and the fourth inverse cumulative distribution function, or a second approximate time waveform that is a time waveform represented by addition of the second level value and the difference or the weighted difference between the third inverse cumulative distribution function and the fourth inverse cumulative distribution function;

setting, as a residual time waveform, any one of a time waveform of a difference between the first target time waveform and the first approximate time waveform, a time waveform of a difference between the second target time waveform and the second approximate time waveform, and a time waveform obtained by inverting a time axis of a waveform of a difference between the second target inverse time waveform and the second approximate inverse time waveform, setting a cumulative distribution function of a fifth unimodal distribution as a fifth cumulative distribution function, and setting a cumulative distribution function of a sixth unimodal distribution as a sixth cumulative distribution function;

setting, as a plurality of types of myocardial activity parameters included in a third group, a parameter specifying the fifth unimodal distribution, a parameter specifying the fifth cumulative distribution function, and weight of the fifth cumulative distribution function when the residual time waveform is approximated by an approximate residual time waveform that is a time waveform represented by multiplication of the fifth cumulative distribution function or the fifth cumulative distribution function by weight, or a parameter specifying the fifth unimodal distribution, a parameter specifying the fifth cumulative distribution function, a parameter specifying the sixth unimodal distribution, a parameter specifying the sixth cumulative distribution function, weight of the fifth cumulative distribution function, weight of the sixth cumulative distribution function, and a ratio between the weight of the fifth cumulative distribution function and the weight of the sixth cumulative distribution function when the residual time waveform is approximated by an approximate residual time waveform that is a time waveform represented by a difference or a weighted difference between the fifth cumulative distribution function and the sixth cumulative distribution function;

setting, as one or more types of myocardial activity parameters included in a fourth group, parameters obtained by an arithmetic operation of a plurality of types of myocardial activity parameters among a plurality of types of myocardial activity parameters included in the first group, a plurality of types of myocardial activity parameters included in the second group, and a plurality of types of myocardial activity parameters included in the third group;

setting, as a myocardial activity parameter set, a set of predetermined one or more types of myocardial activity parameters among a plurality of types of myocardial activity parameters included in the first group, a plurality of types of myocardial activity parameters included in the second group, a plurality of types of myocardial activity parameters included in the third group, and one or more types of myocardial activity parameters included in the fourth group, obtained from one or more cycles of waveforms indicating the cardiac cycle of the heart; and performing learning of an estimation model that obtains heart state information that is information representing a state of a heart corresponding to a myocardial activity parameter with the myocardial activity parameter set as an input, by using a learning data set, wherein the learning data set includes Y pieces of learning data (Y is a plural number), and each of the Y pieces of learning data includes a myocardial activity parameter set of a heart that is a target of a y-th learning data, and heart state information that is information representing a state of the heart that is the target of the y-th learning data, where each of integers greater than or equal to 1 and less than or equal to Y is y.

* * * * *